(12) United States Patent
Dockal et al.

(10) Patent No.: US 8,632,991 B2
(45) Date of Patent: Jan. 21, 2014

(54) METHODS AND COMPOSITIONS FOR TREATING BLEEDING DISORDERS

(75) Inventors: Michael Dockal, Vienna (AT); Hartmut Ehrlich, Vienna (AT); Friedrich Scheiflinger, Vienna (AT)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 330 days.

(21) Appl. No.: 13/006,396

(22) Filed: Jan. 13, 2011

(65) Prior Publication Data

US 2011/0172156 A1 Jul. 14, 2011

Related U.S. Application Data

(60) Provisional application No. 61/335,964, filed on Jan. 14, 2010.

(51) Int. Cl.
| | |
|---|---|
| *A61K 51/00* | (2006.01) |
| *G01N 33/86* | (2006.01) |
| *A61K 49/00* | (2006.01) |
| *C12Q 1/56* | (2006.01) |

(52) U.S. Cl.
USPC ........ 435/13; 436/69; 436/119; 436/117; 436/178; 436/811; 424/1.73; 424/9.2; 524/23; 524/25; 524/54; 524/56; 524/834

(58) Field of Classification Search
USPC ......... 435/7.1, 13; 436/16, 17, 34, 69, 119, 436/177, 178; 424/1.73, 9.2; 524/23, 25, 524/54, 56, 834
See application file for complete search history.

(56) References Cited

U.S. PATENT DOCUMENTS

| | | | |
|---|---|---|---|
| 7,829,549 B2* | 11/2010 | Johnson | 514/54 |
| 2003/0203845 A1 | 10/2003 | Knudsen et al. | |
| 2005/0282771 A1 | 12/2005 | Johnson | |
| 2005/0282775 A1 | 12/2005 | Kennedy | |
| 2007/0218076 A1 | 9/2007 | Michailovna | |
| 2008/0107678 A1* | 5/2008 | Johnson | 424/195.17 |
| 2009/0098185 A1 | 4/2009 | Johnson | |

FOREIGN PATENT DOCUMENTS

| | | |
|---|---|---|
| EP | 0251134 | 1/1988 |
| JP | 7215990 | 8/1995 |
| JP | 2003171262 | 6/2003 |
| WO | 9918961 | 4/1999 |
| WO | 2004029095 | 4/2004 |

(Continued)

OTHER PUBLICATIONS

Life Extension (Optimized Fucoidan with Maritech 926, Catalog No. 01513 (1995-2013).*

(Continued)

*Primary Examiner* — Gail R Gabel
(74) *Attorney, Agent, or Firm* — Bozicevic, Field & Francis LLP; Bret E. Field; Khin K. Chin

(57) ABSTRACT

Aspects of the invention include methods for enhancing blood coagulation in a subject. In practicing methods according to certain embodiments, an amount of a non-anticoagulant sulfated polysaccharide (NASP) is administered to a subject to enhance blood coagulation in the subject. Also provided are methods for preparing a NASP composition having blood coagulation enhancing activity. Compositions and kits for practicing methods of the invention are also described.

13 Claims, 17 Drawing Sheets

Calibrated Automated Thrombagraphy (CAT): Evaluation of Compounds

L/FVF-01091
Fucus v.

(56) References Cited

FOREIGN PATENT DOCUMENTS

| WO | WO 2005/117912 A1 | 12/2005 |
|---|---|---|
| WO | 2007127298 | 11/2007 |
| WO | 2008090631 | 7/2008 |
| WO | 2008103234 | 8/2008 |

OTHER PUBLICATIONS

Prasad et al., "Efficacy and safety of a new class hemostatic drug candidate, AV513, in dogs with hemophilia A" Blood 111 (2): 672-678 (2008).
Bates, et al., "The New Heparins," Coron. Artery Dis. 2(2-3):65-74 (1998).
Bishop, et al., "Recombinant Biologics for Treatment of Bleeding Disorders," Nat. Rev. Drug Discov. 2.(8):684-94 (2004).
Bourin, et al., "Glycosaminoglycans and The Regulation of Blood Coagulation," Biochem J. 289(Pt 2):313-30 (1993).
Broze, "The Role of Tissue Factor Pathway Inhibitor in a Revised Coagulation Cascade," Semin. Haematol. 29(3): 159-69 (1992).
Broze, "The Rediscovery and Isolation OfTFPI," 1. T'hromb. Haemost.l(8): 1671-5 (2003).
Brummel Ziedens, et al., "Factor Viia Replacement Therapy in Factor VII Deficiency," J. T'hromb. Haemost. 6(10): 1735-44 (2Q04).
Carcao, et al., "Prophylactic Factor Replacement in Hemophilia," Blood Rev.II(2): I 01-13 (2004).
Church, et al., "Antithrombin Activity of Fucoidan. The Interaction OfFucoidan With Heparin Cofactor II, Antithrombin III, and Thrombin," J. Bioi. Chem. 264(6):3618-23 (1989).
Goodman-Gilman, "The Pharmacological Basis of Therapeutics" editors Joel G. Hardman and Lee E. Limbard; published by The McGraw-Hill Companies Inc., (2001) pp. 54-56.
Davie, et al., "The Coagulation Cascade: Initiation, Maintenance, and Regulation," Biochemistry 30(43): 10363-70 (1991).
Erhardtsen, et al., "Blocking OfTissue Factor Pathway Inhibitor (TFPI) Shortens The Bleeding Time in Rabbits With Antibody Induced Haemophilia A," Blood Coagul. Fibrinolysis 2(5):388-94 (1995).
Fryer, et al., "Selective O-Desulfation Produces Nonanticoagulant Heparin That Retains Pharmacological Activity in the Lung," J Pharmacol £xp Ther. m(I):208-19 (1997).
Giedrojc, et al., "Comparative Study on the In Vitro and In Vivo Activities of Heparinoids Derivative Investigated on The Animal Model," J. Cardiovasc. Pharmacol. 34(3):340-5 (1999).
Granert, et al., "Effects of Polysaccharide Fucoidin on Cerebrospinal Fluid Interleukin-I and Tumor Necrosis Factor Alpha in Pneumococcal Meningitis in The Rabbit," Irifect. Immun. 67(5):2071-4 (1999).
Hirsh, et al., "New Anticoagulants," Blood W(2):453-63 (2005).
Johnson, et al., "Novel Anticoagulants Based on Inhibition of the Factor ViialTissue Factor Pathway," Coron. Artery Dis. 2(2-3):83-7 (1998).
Kleesiek, et al., "The 536C→T Transition in The Human Tissue Factor Pathway Inhibitor (TFPJ) Gene is Statistically Associated With a Higher Risk for Venous Thrombosis," Thromb. Haemost. 82(1):1-5 (1999).
Official Action in U.S. Appl. No. 12/316,632, Mail Date Jun. 25, 2009, 11 pages.
Lee, "Von Willebrand Disease, Hemophilia A and B, and Other Factor Deficiencies," Int. Anesthesiol. Clin. 42(3):59-76 (2004).
Liu, et al., "Improved coagulation in bleeding disorders by Non-Anticoagulant Sulfated Polysaccharides (NASP)," Thrombosis and Haemostasis 95:68-76 (2006).
Luyt, et al. "Low-Molecular-Weight Fucoidan Promotes Therapeutic Revascularization in a Rat Model of Critical Hindlimb Ischemia," J. Pharmacol. Exp. Ther. 305(1):24-30 (2003).
MacGregor, et al., "Metabolism of Sodium Pentosan Polysulphate in Man Measured'by a New Competitive Binding Assay for Sulphated Polysaccharides—Comparison With Effects Upon Anticoagulant Activity, LipolysisAnd Platelet Alpha-Granule Proteins," Thromb. Haemost. 53(3):4II-4 (1985).
Mann, "Thrombin: Can't Live Without It; Probably Die From It," Chest 124(3 Suppl):IS-3S (2003).
Mann, "Thrombin Formation," Chest 124(3 Suppl):4S-10S (2003).
McAuliffe, et al. Chem.Indus. Magazine 2:170-4 (1997).
McCaffrey et al. Biochem. Biophys. Res. Commun. 184(2):773-81 (1992).
Millet, et al. "Antithrombotic and Anticoagulant Activities of a Low Molecular Weight Fucoidan by the Subcutaneous Route;" Thromb. Haemost. 81:391-5 (1999).
Nordfang, et al. "Inhibition of Extrinsic Pathway Inhibitor Shortens the Coagulation Time of Normal Plasma and of Hemophilia Plasma," Thromb. Haemost. 66(4):464-67 (1991).
Novotny, et al. "Purification and Properties of Heparin-Releasable Lipoprotein-Associated Coagulation Inhibitor," Blood 78(2):394-400 (1991).
Orgueira, et al. "Modular Synthesis of Heparin Oligosaccharides," Chem. Eur. J. 2(1):140-69 (2003).
Rapaport, et al., "The Tissue Factor Pathway: How It Has Become a 'Prima Ballerina'," Thromb. Haemost 74(1):7-17 (\995).
Roberts, et al., "Current Concepts of Hemostasis: Implications for Therapy," Anesthesiology 100(3):722-30 (2004).
Sinay, "Sugars Slide Into Heparin Activity," Nature 398(6726):377-S (1999).
Toida ei al. Trends in Glyoeseienee and Glyeoteehnology 15(81):29-46 (2003).
van't Veer C et al., "Regulation of Tissue Factor Initiated Thrombin Generation by the Stoichiometric Inhibitors Tissue Factor Pa THWA Y Inhibitor, Antithrombin-III, and Heparin Cofactor-II ", Journal of Biological Chemistry, American Society of Biolochemical Biologists, Birmingham, US, 272(7):4367-4377 (1997).
Vicente, et al., "Unbalanced Effects of 1-23 Dermation Sulfates With Different Sulfation Patterns on Coagulation, Thrombosis and Bleeding," Thromb Haenos 86(5): 121 5-1220 (2001).
Wang, et al., "N-Desulfated Non-Anticoagulant Heparin Inhibits Leukocyte Adhesion and Transmigration In Vitro and Attenuates Acute Peritonitis and Ischemia and Reperfusion Injury In Vivo," Inflamm. Res. 51(9):435-43 (2002).
Welsch, et al., "Effect of Lipoprotein-Associated Coagulation Inhibitor (LACI) on Thromboplastin~Induced Coagulation OfNormal and Hemophiliac Plasmas," Thromb. Res. 64(2):213-22 (1991).
Westrick, et al., "Deficiency of Tissue Factor Pathway Inhibitor Promotes Atherosclerosis and Thrombosis in Mice," Circulation 103(25):3044-6 (200 I).
Williams, et al., "Comparative Effects of Heparin and the Sulfatoid GMI474 on Coagulation parameters in Plasma and Blood From Various Species," Gen. Pharmacol. 30(3):337-41 (1998).
Li et al., "Fucoidan: structure and bioactivity" Molecules (2008) vol. 13, No. 8 pp. 1671-1695 XP002574600.
Prasad et al., "Efficacy and safety of a new-class hemostatic drug candidate, AV513, in dogs with homphilia A" Blood, vol. 111, No. 2 (2008) pp. 672-679 XP002574599.
Li et al, "Toxicological Evaluation of Ducoidian Extracted from Laiminara Japonica in Wistar Rats" Foo Chem Toxicol 43: 421-426 (2005).
Mourao, "Use of Slfated Fucans as Anticoagulant and Antithombotic Agents: Future Perspectives" Curr Pharma Des 10: 967-981 (2004).
Irhimeh et al., "Pilot clinical study to evaluate the anticoagulant activity of fucoidan", Blood Coagulation and Fibrinolysis, vol. 20, No. 7, pp. 607-610 (2009).
Kim et al., "A 4-week repeated oral dose toxicity study of fucoidan from the Sporophyll of *Undaria pinnatifida* in Sprague-Dawley rats", Toxicology, vol. 267, No. 1-3, pp. 154-158 (2010).

\* cited by examiner

Activated Partial Thromboplastin Time (aPTT) Assay

METHODS AND COMPOSITIONS FOR TREATING BLEEDING DISORDERS

CROSS-REFERENCE TO RELATED APPLICATION

Pursuant to 35 U.S.C. §119(e), this application claims priority to U.S. Provisional Patent Application Ser. No. 61/335,964, filed on Jan. 14, 2010, the disclosure of which is herein incorporated by reference.

INTRODUCTION

Bleeding is one of the most serious and significant manifestations of disease, and may occur from a local site or be systemic. Localized bleeding may be associated with lesions and may be further complicated by a defective haemostatic mechanism. Blood clotting is inadequate in bleeding disorders, which may be caused by congenital coagulation disorders, acquired coagulation disorders, or hemorrhagic conditions induced by trauma. Congenital or acquired deficiencies of any of the coagulation factors may be associated with a hemorrhagic tendency. Some congenital coagulation disorders include hemophilia, a recessive X-linked disorder involving a deficiency of coagulation factor VIII (hemophilia A) or factor IX (hemophilia B) and von Willebrands disease, a rare bleeding disorder involving a severe deficiency of von Willebrands factor. Acquired coagulation disorders may arise in individuals without a previous history of bleeding as a result of a disease process. For example, acquired coagulation disorders may be caused by inhibitors or autoimmunity against blood coagulation factors, such as factor VIII, von Willebrand factor, factors IX, V, XI, XII and XIII; or by hemostatic disorders such as caused by liver disease, which may be associated with decreased synthesis of coagulation factors.

SUMMARY

Aspects of the invention include methods for enhancing blood coagulation in a subject. In practicing methods according to certain embodiments, an amount of a non-anticoagulant sulfated polysaccharide (NASP) is administered to a subject to enhance blood coagulation in the subject. Also provided are methods for preparing a NASP composition having blood coagulation enhancing activity. Compositions and kits for practicing methods of the invention are also described.

In certain embodiments, the present invention provides a method for enhancing blood coagulation by administering a composition having an amount of a NASP to a subject, where the NASP has a sulfur content of 8% or more by weight. In some instances, the NASP is a fucoidan. For example, in these embodiments, the fucoidan may be Fucoidan GFS 5508005, *Undaria pinnatifida*, depyrogenated; Fucoidan GFS 5508004, *Undaria pinnatifida*; Fucoidan GFS 5508003, *Undaria pinnatifida*; Fucoidan 5307002, *Fucus vesiculosus*, max. MW peak 126.7 kD; Fucoidan VG49, *Fucus vesiculosus*, hydrolyzed sample of 5307002 of lower MW, max. MW peak 22.5 kD; Fucoidan 5308004, *Fucus vesiculosus*; Fucoidan 5308005, *Fucus vesiculosus*; Fucoidan L/FVF1091, *Fucus vesiculosus*; Fucoidan VG201096A, *Fucus vesiculosus*; Fucoidan VG201096B, *Fucus vesiculosus*; Fucoidan VG57, *Undaria pinnatifida*, high charge (high sulphation, deacetylated); Fucoidan VG50, *Ascophyllum nodosum*, max. MW peak 149.7 kD; and combinations thereof.

In some instances, methods of invention further include administering a blood coagulation factor to the subject in conjunction with a NASP having a sulfur content of 8% or more. In these instances, the blood coagulation factor may include but are not limited to factor Xa, factor IXa, factor XIa, factor XIIa, VIIIa, prekallekrein, and high-molecular weight kininogen, tissue factor, factor VIIa, factor Va, factor Xa, factor II, factor V, factor VII, factor VIII, factor IX, factor X, factor XI, factor XII, factor XIII, von Willebrands factor, and combinations thereof. For example, in some embodiments, methods of the invention include administering to a subject an amount of a NASP having a sulfur content of 8% or more and factor VIII. In another embodiment, methods include administering to a subject an amount of a NASP having a sulfur content of 8% or more and factor IX.

In certain embodiments, aspects of the invention also provide methods for preparing a NASP having blood coagulation enhancing activity by extracting a NASP from a biological source and increasing the sulfur content of the extracted NASP. For example, in some instances, the sulfur content of the NASP may be increased in a manner sufficient to produce a NASP having a sulfur content of 10% sulfur or more by weight. In other instances, the sulfur content of the NASP may be increased in a manner sufficient to produce a NASP having a sulfur content of 15% sulfur or more by weight.

In certain embodiments, the present invention provides a method for enhancing blood coagulation by administering an amount of a NASP to a subject, where the NASP has 40% or more fucose saccharide residues. In some instances, the NASP is a fucoidan. For example, in these embodiments, the fucoidan may be Fucoidan GFS 5508005, *Undaria pinnatifida*, depyrogenated; Fucoidan GFS 5508004, *Undaria pinnatifida*; Fucoidan VG 23, *E. Maxima*; Fucoidan L/FVF1093, *Fucus vesiculosus*, Fucoidan L/FVF1092, *Fucus vesiculosus*; and combinations thereof.

In certain embodiments, methods of invention further include administering a blood coagulation factor to the subject in combination with a NASP having 40% or more fucose saccharide residues. In these instances, the blood coagulation factor may include but are not limited to factor Xa, factor IXa, factor XIa, factor XIIa, VIIIa, prekallekrein, and high-molecular weight kininogen, tissue factor, factor VIIa, factor Va, factor Xa, factor II, factor V, factor VII, factor VIII, factor IX, factor X, factor XI, factor XII, factor XIII, von Willebrands factor, and combinations thereof. For example, in one embodiment, methods of the invention include administering to a subject an amount of a NASP having 40% or more fucose saccharide residues and factor VIII. In another embodiments, methods include administering to a subject an amount of a NASP having 40% or more fucose saccharide residues and factor IX.

In certain embodiments, the present invention provides a method for enhancing blood coagulation by administering to a subject an amount of one or more of Fucoidan 5307002, *Fucus vesiculosus*, max. MW peak 126.7 kD; Fucoidan VG49, *Fucus vesiculosus*, hydrolyzed sample of 5307002 of lower MW, max. MW peak 22.5 kD; Fucoidan VG57, *Undaria pinnatifida*, high charge (high sulphation, deacetylated); Fucoidan GFS (5508005), *Undaria pinnatifida*, depyrogenated; Fucoidan GFS (L/FVF-01091), *Fucus vesiculosus*, depyrogenated, max. MW peak 125 kD; Fucoidan GFS (L/FVF-01092), *Fucus vesiculosus*, depyrogenated, max. MW peak 260 kD; Fucoidan GFS (L/FVF-01093), *Fucus vesiculosus*, hydrolyzed depyrogenated, max. MW peak 36 kD; Maritech® *Ecklonia radiata* extract; Maritech® *Eckло-* nia maxima extract; Maritech® Macrocystis pyrifera extract; Maritech® Immune trial Fucoidan Blend; and combinations thereof.

In certain embodiments, methods of the invention include enhancing blood coagulation by administering to a subject an amount of Fucoidan GFS (L/FVF-01091), *Fucus vesiculosus*, depyrogenated, max. MW peak 125 kD to the subject to enhance blood coagulation.

In some instances, methods of invention may further include administering a blood coagulation factor to the subject in conjunction with one of the fucoidans noted above. In these instances, the blood coagulation factor may include but are not limited to factor Xa, factor IXa, factor XIa, factor XIIa, VIIIa, prekallekrein, and high-molecular weight kininogen, tissue factor, factor VIIa, factor Va, factor Xa, factor II, factor V, factor VII, factor VIII, factor IX, factor X, factor XI, factor XII, factor XIII, von Willebrands factor, and combinations thereof. For example, in some embodiments, methods of the invention include administering to a subject an amount of Fucoidan GFS (L/FVF-01091), *Fucus vesiculosus*, depyrogenated, max. MW peak 125 kD and factor VIII. In another embodiment, methods include administering to a subject an amount of Fucoidan GFS (L/FVF-01091), *Fucus vesiculosus*, depyrogenated, max. MW peak 125 kD and factor IX.

In certain embodiments, compositions of the invention decreases blood clotting time when tested in the dPT assay. In additional embodiments, the compositions of interest display procoagulant activity as determined using calibrated automated thrombography (CAT) in Factor VIII and/or Factor IX deficient plasma.

RELEVANT DEFINITIONS

Figure 1:
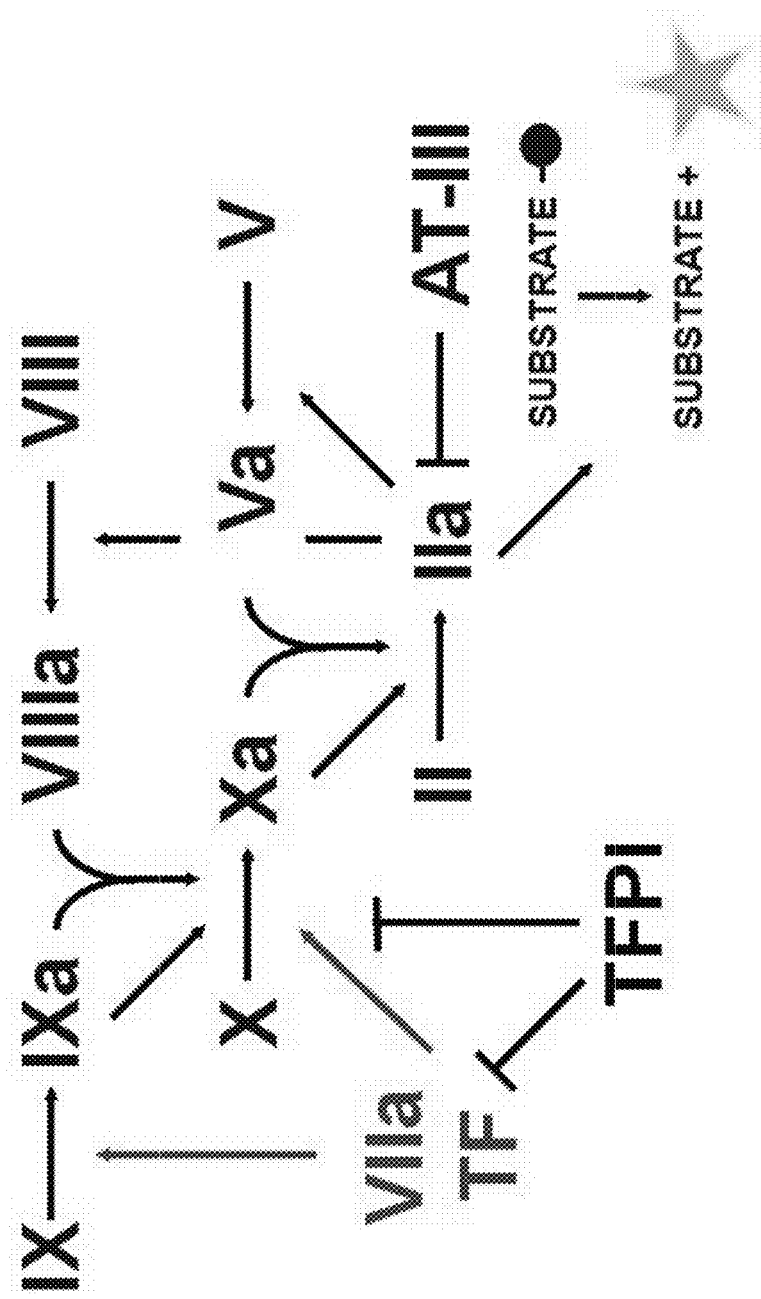
FIG. 1 shows the mechanism of thrombin generation as as measured using calibrated automated thrombography (CAT) in FVIII-inhibited plasma.

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to a "NASP" may include a mixture of two or more NASPs, as desired.

An "NASP" as used herein refers to sulfated polysaccharide (SP) extracted from a biological source that exhibit non-anticoagulant and anticoagulant activity in any of the various clotting assays described herein. One measure of activity is to compare the clotting time demonstrated by a NASP with the anticoagulant activity displayed by heparin. For example, NASPs of interest exhibit anticoagulant activity in the dilute prothrombin time (dPT) or activated partial thromboplastin time (aPTT) clotting assay that is no more than one-third, such as less than one-tenth, the molar anticoagulant activity of unfractionated heparin (MW range 8,000 to 30,000; mean 18,000 daltons). As such, NASPs of interest demonstrate a 2-fold or more lower anticoagulant activity as compared to heparin, such as a 5-fold or more lower anticoagulant activity as compared to heparin, such as a 10-fold or more lower anticoagulant activate as compared to heparin, such as a 25-fold or more lower anticoagulant activity as compared to heparin, such as a 50-fold or more lower anticoagulant activity as compared to heparin, including a 100-fold or more lower anticoagulant activity as compared to heparin, by employing methods and compositions as provided herein.

NASPs of interest may range in molecular weight from 10 daltons to 1,000,000 daltons, such as for example, from 100 daltons to 900,000 daltons, such as from 500 daltons to 500,000 daltons, such as from 1000 daltons to 250,000 daltons, including 5000 daltons to 150,000 daltons. Fucoidans may range in average molecular weight from about 10 daltons to about 500,000 daltons, such as from about 100 daltons to about 300,000 daltons, such as from 1000 daltons to 250,000 daltons, including 1000 daltons to 150,000 daltons.

NASPs may be used in the methods of the invention for improving hemostasis, in treating bleeding disorders, such as those associated with deficiencies of coagulation factors or for reversing the effects of anticoagulants. The ability of NASPs to promote clotting and reduce bleeding may be determined using various in vitro clotting assays (e.g., TFPI-dPT, thrombin generation and thromboelastography (TEG) assays) and in vivo bleeding models (e.g. tail snip, transverse cut, whole blood clotting time, or cuticle bleeding time determination in hemophilic mice or dogs). See, e.g., PDR Staff. Physicians' Desk Reference. 2004, Anderson et al. (1976) Thromb. Res. 9:575-580; Nordfang et al. (1991) Thromb Haemost. 66:464-467; Welsch et al. (1991) Thrombosis Research 64:213-222; Broze et al. (2001) Thromb Haemost 85:747-748; Scallan et al. (2003) Blood. 102:2031-2037; Pijnappels et al. (1986) Thromb. Haemost. 55:70-73; and Giles et al. (1982) Blood 60:727-730, and the examples herein.

A "procoagulant" is used herein in its conventional sense to refer to any factor or reagent capable of initiating or accelerating clot formation. A procoagulant of the invention includes but is not limited to any activator of the intrinsic or extrinsic coagulation pathways, such as a clotting factor selected from the group consisting of factor Xa, factor IXa, factor XIa, factor XIIa, and VIIIa, prekallekrein, high-molecular weight kininogen, tissue factor, factor VIIa, and factor Va, as well as other reagents that promote clotting include kallikrein, APTT initiator (i.e., a reagent containing a phospholipid and a contact activator), Russel's viper venom (RVV time), and thromboplastin (for dPT). In some embodiments, contact activators may be employed as procoagulant reagents. For example, contact activators may include micronized silica particles, ellagic acid, sulfatides, kaolin or the like. Procoagulants may be from a crude natural extract, a blood or plasma sample, isolated and substantially purified, synthetic, or recombinant. Procoagulants may include naturally occurring clotting factors or fragments, variants or covalently modified derivatives thereof that retain biological activity (i.e., promote clotting).

The term "polysaccharide," as used herein, refers to a polymer containing two or more covalently linked saccharide residues. Saccharide residues may be linked for example by glycosidic, ester, amide, or oxime linking moieties. The average molecular weight of polysaccharides may vary widely, such as for example ranging from 100 to 1,000,000 daltons and more, such as 100 to 500,000 daltons and more, such as 1000 to 250,000 daltons and more, such as 1000 to 100,000 daltons and more, such as 10,000 to 50,000 daltons and more. Polysaccharides may be straight chained (i.e., linear) or branched or may contain discrete regions of linear and branched portions. Polysaccharides may also be fragments of polysaccharides generated by degradation (e.g., hydrolysis) of larger polysaccharides. Degradation can be achieved by any convenient protocol including treatment of polysaccharides with acid, base, heat, oxidants or enzymes to yield fragmented polysaccharides. Polysaccharides may be chemically altered and may be modified, including but not limited to, sulfation, polysulfation, esterification, and methylation.

Molecular weight, as discussed herein, can be expressed as either a number average molecular weight or a weight average molecular weight. Unless otherwise indicated, all references to molecular weight herein refer to the weight average molecular weight. Both molecular weight determinations, number average and weight average, can be measured using for example, gel permeation chromatography or other liquid chromatography techniques.

The term "derived from" is used herein to identify the original source of a molecule but is not meant to limit the method by which the molecule is made which can be, for example, by chemical synthesis or recombinant methodologies.

The terms "variant," "analog" and "mutein" refer to biologically active derivatives of a reference molecule, that retain desired activity, such as clotting activity in the treatment of a bleeding disorder. The terms "variant" and "analog" in reference to a polypeptide (e.g., clotting factor) refer to compounds having a native polypeptide sequence and structure with one or more amino acid additions, substitutions (generally conservative in nature) and/or deletions, relative to the native molecule, so long as the modifications do not destroy biological activity and which are "substantially homologous" to the reference molecule as defined below. The amino acid sequences of such analogs will have a high degree of sequence homology to the reference sequence, e.g., amino acid sequence homology of 50% or more, such as 60% or more, such as 70% or more, such as 80% or more, such as 90% or more, such as 95% or more, including 99% or more when the two sequences are aligned. In some instances, analogs will include the same number of amino acids but will include substitutions. The term "mutein" further includes polypeptides having one or more amino acid-like molecules including but not limited to compounds contain only amino and/or imino molecules, polypeptides containing one or more analogs of an amino acid (including, for example, synthetic non-naturally occurring amino acids, etc.), polypeptides with substituted linkages, as well as other modifications known in the art, both naturally occurring and non-naturally occurring (e.g., synthetic), cyclized, branched molecules and the like. The term also includes molecules comprising one or more N-substituted glycine residues (a "peptoid") and other synthetic amino acids or peptides. (See, e.g., U.S. Pat. Nos. 5,831,005; 5,877,278; and 5,977,301; Nguyen et al., Chem. Biol. (2000) 7:463-473; and Simon et al., Proc. Natl. Acad. Sci. USA (1992) 89:9367-9371 for descriptions of peptoids). In embodiments of the invention, analogs and muteins have at least the same clotting activity as the native molecule.

As discussed above, analogs may include substitutions that are conservative, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are in some instances classified as aromatic amino acids. For example, an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions, or even up to about 15-25 conservative or non-conservative amino acid substitutions, or any integer between 5-25, so long as the desired function of the molecule remains intact.

By "derivative" is meant any suitable modification of the reference molecule of interest or of an analog thereof, such as sulfation, acetylation, glycosylation, phosphorylation, polymer conjugation (such as with polyethylene glycol), or other addition of foreign moieties, so long as the desired biological activity (e.g., clotting activity, inhibition of TFPI activity) of the reference molecule is retained. For example, polysaccharides may be derivatized with one or more organic or inorganic groups. Examples include but are not limited to polysaccharides substituted in at least one hydroxyl group with another moiety (e.g., a sulfate, carboxyl, phosphate, amino, nitrile, halo, silyl, amido, acyl, aliphatic, aromatic, or a saccharide group), or where a ring oxygen has been replaced by sulfur, nitrogen, a methylene group, etc. Polysaccharides may be chemically altered, for example, to improve procoagulant function. Such modifications may include, but are not limited to, sulfation, polysulfation, esterification, and methylation.

By "fragment" is meant a molecule containing a part of the intact full-length sequence and structure. In some instances, a fragment of a polysaccharide may be generated by degradation (e.g., hydrolysis) of a larger polysaccharide. Active fragments of a polysaccharides of the invention may include about 2-20 saccharide units of the full-length polysaccharide, such as about 5-10 saccharide units of the full-length molecule, and including any integer between 2 saccharide units and the full-length molecule, so long as the fragment retains biological activity, such as for example, clotting activity or the ability to inhibit TFPI activity. A fragment of a polypeptide can include a C-terminal deletion, an N-terminal deletion, or an internal deletion of the native polypeptide. Active fragments of a particular protein may include, in some embodiments, about 5-10 contiguous amino acid residues of the full-length molecule or more, such as about 15-25 contiguous amino acid residues of the full-length molecule or more, such as about 20-50 contiguous amino acid residues of the full-length molecule or more, and including any integer between 5 amino acids and the full-length sequence, so long as the fragment in question retains biological activity, such as for example, clotting activity.

By "substantially purified" is meant the isolation of a substance (e.g., non-anticoagulant sulfated polysaccharide) such that the substance includes the majority of the sample in which it resides. For example, a sample that is substantially purified contains 50% or more of the substance of interest, such as 60% or more of the substance of interest, such as 75% or more of the substance of interest, such as 90% or more of the substance of interest, such as 95% or more of the substance of interest, including 99% or more of the substance of interest. Any convenient protocol may be employed for purifying polysaccharides, polynucleotides, and polypeptides of interest and include, but are not limited to ultrafiltration, selective precipitation, crystallization, ion-exchange chromatography, affinity chromatography and sedimentation according to density.

By "isolated" is meant, when referring to a polysaccharide or polypeptide, that the indicated molecule is separate and discrete from the whole organism with which the molecule is found in nature or is present in the substantial absence of other biological macro-molecules of the same type.

By "homology" is meant the percent identity between two polypeptide moieties. As referred to herein, two polypeptide sequences are "substantially homologous" to each other when the sequences exhibit about 50% or more sequence identity, such as 60% or more sequence identity, such as 75% or more sequence identity, such as 85% or more sequence identity, such as 90% or more sequence identity, such as 95% or more sequence identity, including 99% or more sequence identity. In some embodiments, substantially homologous polypeptides include sequences having complete identity to a specified sequence.

By "identity" is meant an exact subunit to subunit correspondence of two polymeric sequences. For example, an identical polypeptide is one that has an exact amino acid-to-amino acid correspondence to another polypeptide or an identical polynucleotide is one that has an exact nucleotide-to-nucleotide correspondence to another polynucleotide. Percent identity can be determined by a direct comparison of the sequence information between two molecules (the reference sequence and a sequence with unknown % identity to the reference sequence) by aligning the sequences, counting the exact number of matches between the two aligned sequences, dividing by the length of the reference sequence, and multiplying the result by 100. Any convenient protocol may be employed to determine percent identity between two polymeric sequences, such as for example, ALIGN, Dayhoff, M. O. in *Atlas of Protein Sequence and Structure* M. O. Dayhoff ed., 5 Suppl. 3:353-358, National biomedical Research Foundation, Washington, D.C., which adapts the local homology algorithm of Smith and Waterman *Advances in Appl. Math.* 2:482-489, 1981 for peptide analysis.

By "subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are of interest.

The term "patient," is used in its conventional sense to refer to a living organism suffering from or prone to a condition that can be prevented or treated by administration of a NASP of the invention, and includes both humans and non-human animals.

By "biological sample" is meant a sample of tissue or fluid isolated from a subject, including but not limited to, for example, blood, plasma, serum, fecal matter, urine, bone marrow, bile, spinal fluid, lymph fluid, samples of the skin, external secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components.

By "therapeutically effective dose or amount" is meant an amount that, when administered as described herein, brings about the desired therapeutic response, such as for example, reduced bleeding or shorter clotting times.

By "bleeding disorder" is meant any disorder associated with excessive bleeding, such as a congenital coagulation disorder, an acquired coagulation disorder, administration of an anticoagulant, or a trauma induced hemorrhagic condition. As discussed below, bleeding disorders may include, but are not limited to, hemophilia A, hemophilia B, von Willebrand disease, idiopathic thrombocytopenia, a deficiency of one or more contact factors, such as Factor XI, Factor XII, prekallikrein, and high molecular weight kininogen (HMWK), a deficiency of one or more factors associated with clinically significant bleeding, such as Factor V, Factor VII, Factor VIII, Factor IX, Factor X, Factor XIII, Factor II (hypoprothrombinemia), and von Willebrands factor, a vitamin K deficiency, a disorder of fibrinogen, including afibrinogenemia, hypofibrinogenemia, and dysfibrinogenemia, an alpha$_2$-antiplasmin deficiency, and excessive bleeding such as caused by liver disease, renal disease, thrombocytopenia, platelet dysfunction, hematomas, internal hemorrhage, hemarthroses, surgery, trauma, hypothermia, menstruation, and pregnancy.

DETAILED DESCRIPTION

Aspects of the invention include methods for enhancing blood coagulation in a subject. In practicing methods according to certain embodiments, an amount of a non-anticoagulant sulfated polysaccharide (NASP) is administered to a subject to enhance blood coagulation in the subject. Also provided are methods for preparing a NASP composition having blood coagulation enhancing activity. Compositions and kits for practicing methods of the invention are also described.

Before the invention is described in greater detail, it is to be understood that the invention is not limited to particular embodiments described herein as such embodiments may vary. It is also to be understood that the terminology used herein is for the purpose of describing particular embodiments only, and the terminology is not intended to be limiting. The scope of the invention will be limited only by the appended claims Unless defined otherwise, all technical and scientific terms used herein have the same meaning as commonly understood by one of ordinary skill in the art to which this invention belongs. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number. All publications, patents, and patent applications cited in this specification are incorporated herein by reference to the same extent as if each individual publication, patent, or patent application were specifically and individually indicated to be incorporated by reference. Furthermore, each cited publication, patent, or patent application is incorporated herein by reference to disclose and describe the subject matter in connection with which the publications are cited. The citation of any publication is for its disclosure prior to the filing date and should not be construed as an admission that the invention described herein is not entitled to antedate such publication by virtue of prior invention. Further, the dates of publication provided might be different from the actual publication dates, which may need to be independently confirmed.

It is noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of skill in the art upon reading this disclosure, each of the individual embodiments described and illustrated herein has discrete components and features which may be readily separated from or combined with the features of any of the other several embodiments without departing from the scope or spirit of the invention. Any recited method may be carried out in the order of events recited or in any other order that is logically possible. Although any methods and materials similar or equivalent to those described herein may also be used in the practice or testing of the invention, representative illustrative methods and materials are now described.

In further describing the subject invention, methods for enhancing blood coagulation in a subject are described first in greater detail. Next, methods for preparing a NASP composition having blood coagulation enhancing activity are reviewed. Compositions and kits for practicing methods of the subject invention are also described.

Methods for Enhancing Blood Coagulation in a Subject

As summarized above, aspects of the invention include methods for enhancing blood coagulation by administering a composition having an amount of a NASP to a subject. The term "enhancing blood coagulation" is used in its conventional sense to refer to accelerating the initiation (i.e., reducing the amount time for coagulation to begin) of blood coagulation as well as the overall rate of blood coagulation of the subject (i.e., reducing the amount of time for blood coagulation to be complete). In some embodiments, methods of the invention accelerate the initiation of blood coagulation. For example, methods of the invention may reduce the amount of time required for the blood to begin coagulating by 5% or more, such as by 10% or more, such as by 25% or more, such as by 50% or more, such as by 75% or more, such as by 90% or more, such as 95% or more, as compared to a suitable control. In other embodiments, methods of the invention increase the rate of blood coagulation. For example, methods of the invention may increase the rate of blood coagulation by 2% or more, such as by 5% or more, such as by 10% or more, such as by 25% or more, such as by 50% or more, such as by 75% or more, such as by 100% or more, such as by 200% or more, including by 500% or more, as compared to a suitable control.

In embodiments of the invention, methods for enhancing blood coagulation in a subject are provided. By "subject" is meant the person or organism receiving the blood coagulation enhancement. As such, subjects of the invention may include but are not limited to humans and other primates, such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like.

In some embodiments, the subject methods may be employed to treat bleeding disorders, such as a chronic or acute bleeding disorder, a congenital coagulation disorder caused by a blood factor deficiency, an acquired coagulation disorder and administration of an anticoagulant. For example, bleeding disorders may include, but are not limited to hemophilia A, hemophilia B, von Willebrand disease, idiopathic thrombocytopenia, a deficiency of one or more contact factors, such as Factor XI, Factor XII, prekallikrein, and high molecular weight kininogen (HMWK), a deficiency of one or more factors associated with clinically significant bleeding, such as Factor V, Factor VII, Factor VIII, Factor IX, Factor X, Factor XIII, Factor II (hypoprothrombinemia), and von Willebrands factor, a vitamin K deficiency, a disorder of fibrinogen, including afibrinogenemia, hypofibrinogenemia, and dysfibrinogenemia, an alpha$_2$-antiplasmin deficiency, and excessive bleeding such as caused by liver disease, renal disease, thrombocytopenia, platelet dysfunction, hematomas, internal hemorrhage, hemarthroses, surgery, trauma, hypothermia, menstruation, and pregnancy.

In other embodiments, the subject methods may be employed to enhance blood coagulation in order to reverse the effects of an anticoagulant in a subject. For example, the subject may have been treated with an anticoagulant including, but not limited to, heparin, a coumarin derivative, such as warfarin or dicumarol, TFPI, AT III, lupus anticoagulant, nematode anticoagulant peptide (NAPc2), active-site blocked factor VIIa (factor VIIai), factor IXa inhibitors, factor Xa inhibitors, including fondaparinux, idraparinux, DX-9065a, and razaxaban (DPC906), inhibitors of factors Va and VIIIa, including activated protein C (APC) and soluble thrombomodulin, thrombin inhibitors, including hirudin, bivalirudin, argatroban, and ximelagatran. In certain embodiments, the anticoagulant in the subject may be an antibody that binds a clotting factor, including but not limited to, an antibody that binds to Factor V, Factor VII, Factor VIII, Factor IX, Factor X, Factor XIII, Factor II, Factor XI, Factor XII, von Willebrands factor, prekallikrein, or high molecular weight kininogen (HMWK).

Aspects of the invention include administering to a subject a composition having an amount of a NASP to enhance blood coagulation. In certain embodiments, methods of the invention include administering to a subject a composition containing an amount of a NASP having a sulfur content that is 8% or more sulfur by weight. For example, the NASP may have a sulfur content that is 10% or more sulfur by weight, such as 15% or more sulfur by weight, such as 20% or more sulfur by weight, including 25% or more sulfur by weight. In other embodiments, NASPs of interest may contain an amount of sulfur that varies, for example ranging from 5 to 25% sulfur by weight, such as 5 to 20% sulfur by weight, such as 5 to 15% sulfur by weight, including 10 to 15% sulfur by weight. Any convenient protocol can be employed to determine the sulfur content of NASPs of interest. Methods for determining the sulfur content may include but is not limited to ion chromatography, gas chromatography, mass spectrometry, inductively coupled plasma, atomic absorption, inductively coupled plasma mass spectrometry, inductively coupled plasma atomic emission spectrometry, flame atomic absorption spectrometry, graphite furnace atomic absorption spectrometry, acidimetric titration, or any combination thereof.

In embodiments of the invention, the sulfur content of NASPs may be present in the form of sulfate. The term "sulfate" is used in it conventional sense refers to the oxyanion of sulfur, $SO_4^{2-}$, however, any oxyanion of sulfur having a central sulfur atom bonded to at least one oxygen atom may be employed, such as sulfite, persulfate, hyposulfate or thiosulfate. The overall amount of sulfate present in the NASP may vary. In certain embodiments, the overall amount of sulfate present in NASPs of the invention is 20% or more sulfate by weight, such as 25% or more sulfate by weight, such as 35% or more sulfate by weight, including 50% or more sulfate by weight. In other embodiments, the overall amount of sulfate in NASPs ranges, for example from 5 to 50% sulfate by weight, such as 5 to 40% sulfate by weight, such as 5 to 30% sulfate by weight, such as 5 to 25% sulfate by weight, such as 10% to 25 sulfate by weight, such as 10 to 20% sulfate by weight, including 10 to 15% sulfate by weight. Any convenient protocol can be employed to determine the amount of sulfation of the NASPs, such as those described above for determining sulfur content. For example, methods for determining the amount of sulfation may include but is not limited to mass spectrometry, inductively coupled plasma, ion chromatography, gas chromatography, atomic absorption, graphite furnace atomic absorption spectrometry, inductively coupled plasma mass spectrometry, inductively coupled plasma atomic emission spectrometry, flame atomic absorption spectrometry, acidimetric titration, or any combination thereof.

Each polysaccharide residue of NASPs of interest may have a degree of sulfation that varies. By "degree of sulfation" is meant the number of sulfate groups bonded to each saccharide residue on the NASP polysaccharide backbone. In some embodiments, each polysaccharide residue (e.g., fucose, galactose, rhamnose, arabinose, glucose, mannose, xylose as described in detail below) may contain one (i.e., monosulfated) or more (i.e., polysulfated) sulfate moieties. For example, in some instances the saccharide residue may be sulfated at the 4-position of the saccharide residue. In other instances, the saccharide residue is sulfated at the 3-position. In certain instances, the saccharide residue is sulfated at both the 4-position and at the 3-position. Each residue may have identical degrees of sulfation (e.g., all saccharide residues being monosulfated) or may have varying degrees of sulfation (e.g., some saccharide residues having identical sulfation and some saccharide residues having different sulfation). For example, 10% or more of the saccharide residues of NASPs of the invention may be monosulfated, such as 15% or more of the saccharide residues, such as 25% or more of the saccharide residues, such as 50% or more of the saccharide residues, such as 75% or more of the saccharide residues, such as 90% or more of the saccharide residues, such as 95% or more of the saccharide residues, including 99% or more of the saccharide residues of NASPs of the invention may be monosulfated. On the other hand, in some embodiments 10% or more of the saccharide residues of NASPs of the invention are polysulfated, such as 15% or more of the saccharide residues, such as 25% or more of the saccharide residues, such as 50% or more of the saccharide residues, such as 75% or more of the saccharide residues, such as 90% or more of the saccharide residues, such as 95% or more of the saccharide residues, including 99% or more of the saccharide residues of NASPs of the invention may be polysulfated. Where both monosulfated and polysulfated saccharide residues are present, the ratio of monosulfated residues to polysulfated residues in NASPs of the invention may vary, and in some instances may range between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the molar ratio of monosulfated residues to polysulfated residues (i.e., monosulfated saccharide residues:polysulfated saccharide residues) in NASPs of interest may range between 1:1 and 1:10; 1:5 and 1:25; 1:10 and 1:50; 1:25 and 1:100; 1:50 and 1:500; or 1:100 and 1:1000. In some embodiments, the ratio of polysulfated residues to monosulfated residues (i.e., polysulfated saccharide residues:monosulfated saccharide residues) in the NASPs ranges between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the ratio of polysulfated saccharide residues to monosulfated residues in NASPs of interest may range between 1:1 and 1:10; 1:5 and 1:25; 1:10 and 1:50; 1:25 and 1:100; 1:50 and 1:500; or 1:100 and 1:1000. Any convenient protocol can be employed to determine the sulfation of the NASPs, such as described above. For example, methods for determining the degree of sulfation of saccharide residues may include but is not limited to mass spectrometry, NMR spectroscopy, IR spectroscopy, or any combination thereof.

In some embodiments, saccharide residues of NASPs of interest may be sulfated at the 4-position. In other embodiments, the saccharide residues are sulfated at the 3-position. In certain embodiments, the saccharide residues are sulfated at the 4-position and at the 3-position. For example, 10% or more of the saccharide residues of NASPs of the invention may be sulfated at the 4-position, such as 15% or more of the saccharide residues, such as 25% or more of the saccharide residues, such as 50% or more of the saccharide residues, such as 75% or more of the saccharide residues, such as 90% or more of the saccharide residues, such as 95% or more of the saccharide residues, including 99% or more of the saccharide residues of NASPs of the invention may be sulfated at the 4-position. In other embodiments 10% or more of the saccharide residues of NASPs of the invention are sulfated at the 3-position, such as 15% or more of the saccharide residues, such as 25% or more of the saccharide residues, such as 50% or more of the saccharide residues, such as 75% or more of the saccharide residues, such as 90% or more of the saccharide residues, such as 95% or more of the saccharide residues, including 99% or more of the saccharide residues of NASPs of the invention are sulfated at the 3-position. In certain embodiments 10% or more of the saccharide residues of NASPs of the invention are sulfated at both the 3-position and the 4-position, such as 15% or more of the saccharide residues, such as 25% or more of the saccharide residues, such as 50% or more of the saccharide residues, such as 75% or more of the saccharide residues, such as 90% or more of the saccharide residues, such as 95% or more of the saccharide residues, including 99% or more of the saccharide residues of NASPs of the invention are sulfated at both the 3-position and the 4-position. Where both saccharide residues sulfated at the 4-position and saccharide residues sulfated at the 3-position are present, the ratio of saccharide residues sulfated at the 4-position to saccharide residues sulfated at the 3-position may vary, and in some instances may range between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the molar ratio of saccharide residues sulfated at the 4-position to saccharide residues sulfated at the 3-position in NASPs of interest may range between 1:1 and 1:10; 1:5 and 1:25; 1:10 and 1:50; 1:25 and 1:100; 1:50 and 1:500; or 1:100 and 1:1000. In some embodiments, the ratio of saccharide residues sulfated at the 3-position to saccharide residues sulfated at the 4-position in the NASPs ranges between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the ratio of saccharide residues sulfated at the 3-position to saccharide residues sulfated at the 4-position in NASPs of interest may range between 1:1 and 1:10; 1:5 and 1:25; 1:10 and 1:50; 1:25 and 1:100; 1:50 and 1:500; or 1:100 and 1:1000. Any convenient protocol can be employed to determine the type of sulfated saccharide residues of the NASPs, such as described above. For example, methods for determining the degree of sulfation of saccharide residues may include but is not limited to mass spectrometry, NMR spectroscopy, IR spectroscopy, or any combination thereof.

In certain embodiments, NASPs of the invention may be extracted from a biological source. By "biological source" is meant a naturally-occurring organism or part of an organism. For example, NASPs of interest may be extracted from plants, animals, fungi or bacteria. In particular, NASPs of interest may be extracted from edible seaweeds, brown algae, echinoderms (e.g., sea urchins, sea cucumbers) and the like. Any convenient protocol can be employed for extracting the NASP from the biological source. For instance, the NASP can be extracted from the biological source by acid-base extraction, enzymatic degradation, selective precipitation, filtration, among other procedures. Methods for extracting and isolating NASPs from biological sources such as edible seaweeds and brown algae are described in detail in co-pending U.S. patent application Ser. No. 12/449,712, filed Feb. 25, 2010, the disclosure of which is herein incorporated by reference, in its entirety.

In some instances NASPs extracted from a biological source are fucoidans having a sulfur content of 8% sulfur or more by weight. For example, fucoidans of interest may include but are not limited to Fucoidan GFS 5508005, *Undaria pinnatifida*, depyrogenated; Fucoidan GFS 5508004, *Undaria pinnatifida*; Fucoidan GFS 5508003, *Undaria pinnatifida*; Fucoidan 5307002, *Fucus vesiculosus*, max. MW peak 126.7 kD; Fucoidan VG49, *Fucus vesiculosus*, hydrolyzed sample of 5307002 of lower MW, max. MW peak 22.5 kD; Fucoidan 5308004, *Fucus vesiculosus*; Fucoidan 5308005, *Fucus vesiculosus*; Fucoidan L/FVF1091, *Fucus vesiculosus*; Fucoidan VG201096A, *Fucus vesiculosus*; Fucoidan VG201096B, *Fucus vesiculosus*; Fucoidan VG57, *Undaria pinnatifida*, high charge (high sulphation, deacetylated); Fucoidan VG50, *Ascophyllum nodosum*, max. MW peak 149.7 kD; and any combinations thereof.

In certain embodiments, aspects of the invention include enhancing blood coagulation in a subject by administering to the subject, a composition that contains an amount of a NASP having a sulfur content that is 8% or more sulfur by weight in combination with a blood coagulation factor. For example, the subject may be administered an amount of a composition containing a NASP having a sulfur content that is 8% or more sulfur by weight and one or more blood coagulation factors which include, but are not limited to factor XI, factor XII, prekallikrein, high molecular weight kininogen (HMWK), factor V, factor VII, factor VIII, factor IX, factor X, factor XIII, factor II, factor VIIa, and von Willebrands factor, factor Xa, factor IXa, factor XIa, factor XIIa, and VIIIa, prekallekrein, and high-molecular weight kininogen, tissue factor, factor VIIa, factor Va, and factor Xa.

Where a composition that contains a NASP having a sulfur content that is 8% sulfur or more by weight and a blood coagulation factor is administered to the subject, the mass ratio of the composition that contains a NASP having a sulfur content that is 8% sulfur or more by weight to the blood coagulation factor ranges between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the mass ratio of the composition that contains a NASP having a sulfur content that is 8% sulfur or more by weight to the blood coagulation factor may range between 1:1 and 1:10; 1:5 and 1:25; 1:10 and 1:50; 1:25 and 1:100; 1:50 and 1:500; or 1:100 and 1:1000. In some embodiments, the mass ratio of the blood coagulation factor to the composition that contains a NASP having a sulfur content that is 8% sulfur or more by weight ranges between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the mass ratio of the blood coagulation factor to the composition that contains a NASP having a sulfur content that is 8% sulfur or more by weight may range between 1:1 and 1:10; 1:5 and 1:25; 1:10 and 1:50; 1:25 and 1:100; 1:50 and 1:500; or 1:100 and 1:1000.

The blood coagulation factor and the composition that contains a NASP having a sulfur content that is 8% sulfur or more by weight may be administered to the subject in any order. In some instances, the composition that contains a NASP having a sulfur content that is 8% sulfur or more by weight is administered prior to administering the blood coagulation factor. In other instances, the composition that contains a NASP having a sulfur content that is 8% sulfur or more by weight is administered in conjunction with administering the blood coagulation factor. In yet other instances, the composition that contains a NASP having a sulfur content that is 8% sulfur or more by weight is administered after administering the blood coagulation factor. Where the composition that contains a NASP having a sulfur content that is 8% sulfur or more by weight is administered in conjunction with the blood coagulation factor, the composition that contains a NASP having a sulfur content that is 8% sulfur or more by weight may be mixed with the blood coagulation factor before administering the composition to the subject. Any convenient mixing protocol may be used, such as a by dry shaking, solution or suspension mixing, industrial mixing protocols and the like.

In some embodiments, methods of the invention also include extracting a NASP from a biological source and increasing the sulfur content of the extracted NASP. As described above, any convenient protocol can be employed for extracting the NASP from the biological source. For example, the NASP can be extracted from the biological source by acid-base extraction, enzymatic degradation, selective precipitation, filtration, among other procedures. Methods for extracting and isolating NASPs from biological sources such as edible seaweeds and brown algae is described in detail in co-pending U.S. patent application Ser. No. 12/449,712, filed Feb. 25, 2010, the disclosure of which is herein incorporated by reference, in its entirety.

In some embodiments, the NASP extracted from the biological source may have a natural sulfur content that is 8% or more sulfur by weight. For example, the NASP extracted from the biological source may have a natural sulfur content that is 10% or more sulfur by weight, such as 15% or more sulfur by weight, such as 20% or more sulfur by weight, including 25% or more sulfur by weight. In other embodiments, the NASP extracted from the biological source may have a sulfur content that is less than 8% sulfur by weight, such as less than 5% sulfur by weight, such as less than 2% sulfur by weight, such as less than 1% sulfur by weight, including less than 0.5% sulfur by weight.

In certain embodiments, the NASP extracted from the biological source is chemically sulfated in a manner sufficient to obtain a NASP having a sulfur content of 8% sulfur or more by weight. For example the NASP extracted from the biological source may be chemically sulfated in a manner to obtain a NASP having 10% sulfur or more by weight, such as 15% sulfur or more by weight, such as 20% sulfur or more by weight, including 25% sulfur or more by weight. As such, methods of the invention increase the sulfur content of the NASP extracted from the biological source. For example, the sulfur content of NASPs extracted from a biological source may be increased by 0.5% sulfur by weight or more, such as 1% sulfur by weight or more, such as 2% or more sulfur by weight, such as 5% or more sulfur by weight, such as 10% or more sulfur by weight, such as 15% or more sulfur by weight, such as 20% or more sulfur by weight, including 25% or more sulfur by weight. In these embodiments, the resulting NASPs may have 1.5-fold more sulfur by weight than the NASP extracted from the biological source, such as 2-fold more sulfur by weight, such as 5-fold more sulfur by weight, such as 10-fold more sulfur by weight, such as 25-fold more sulfur by weight, including 100-fold more sulfur by weight that the NASP extracted from the biological source.

Any convenient protocol can be used to chemically sulfate the NASP extracted from the biological source, so long as the sulfur content of the resulting NASP is 8% sulfur or more by weight and the increased sulfur content is the result of new sulfate moieties covalently bonded to the NASP structure. In these embodiments, any free hydroxyl group located on the saccharide backbone of the extracted NASP can be modified by sulfation to produce a mono- or poly- (e.g., di-substituted) sulfated saccharide. For example, one or more free hydroxyl groups along the saccharide backbone may be sulfated by bonding one or more sulfate anions to the free hydroxyl groups along the saccharide backbone. In other instances, sulfur trioxide complexes with pyridine, triethylamine, or with stannous complexes may be employed (see for example, methods for sulfating hydroxyl groups in Calvo-Asin, J. A., et al., *J. Chem. Soc, Perkin Trans* 1, 1997, 1079).

As discussed above, aspects of the invention include administering to a subject a composition having an amount of a NASP to enhance blood coagulation. In certain embodiments, methods of the invention include administering to a subject a composition having an amount of a NASP that contains 40% or more fucose saccharide residues. The saccharide content of NASPs of interest may vary. In some instances, the saccharide content of NASPs of interest may include, but is not limited to fucose residues, xylose residues, galactose residues, glucose residues, mannose residues, rhamnose residues, arabinose residues and uronic acid. In some embodiments, NASPs of interest are composed of two or more of fucose residues, xylose residues, galactose residues, glucose residues, mannose residues, rhamnose residues, arabinose residues and uronic acid. The amount of each saccharide residue in NASPs of interest may vary. For example, 40% or more of the saccharide residues of NASPs of the invention may be fucose saccharide residues, such as 45% or more of the saccharide residues, such as 50% or more of the saccharide residues, such as 65% or more of the saccharide residues, such as 75% or more of the saccharide residues, such as 90% or more of the saccharide residues, such as 95% or more of the saccharide residues, including 99% or more of the saccharide residues of NASPs of the invention may be fucose saccharide residues. In other instances, 1% or more of the saccharide residues of NASPs of the invention may be galactose saccharide residues, such as 5% or more of the saccharide residues, such as 10% or more of the saccharide residues, such as 15% or more of the saccharide residues, such as 20% or more of the saccharide residues, including 25% or more of the saccharide residues of NASPs of the invention may be galactose saccharide residues. In yet other instances, 1% or more of the saccharide residues of NASPs of the invention may be uronic acid saccharide residues, such as 5% or more of the saccharide residues, such as 10% or more of the saccharide residues, such as 15% or more of the saccharide residues, such as 20% or more of the saccharide residues, including 25% or more of the saccharide residues of NASPs of the invention may be uronic acid saccharide residues. Any convenient protocol can be employed to determine the saccharide content of NASPs of interest. Methods for determining the saccharide content may include but is not limited to ion chromatography, gas chromatography, mass spectrometry, nuclear magnetic resonance spectroscopy, or any combination thereof.

In embodiments of the invention, NASPs of interest may be a linear (i.e., unbranched) polysaccharide or may be a branched polysaccharide. In certain instances, NASPs may have portions of its structure that is linear and other parts of its structure that is branched. By "linear polysaccharide" is meant a polysaccharide or part of a polysaccharide that contains only α-1,4 glycosidic bonds, or α-1,3 glycosidic bonds, or alternating α-1,3/α-1,4 glycosidic bonds. By "branched polysaccharide" is meant a polysaccharide or part of a polysaccharide that contains two or more glycosidic bonds to other saccharide residues, where one of the glycosidic bonds is an α-1,4-glycosidic bond or α-1,3 glycosidic bonds, or alternating α-1,3/α-1,4 glycosidic bonds, and the other is an α-1,6-glycosidic bond. The amount of branching in NASPs of interest may vary.

Aspects of the invention include enhancing blood coagulation in a subject by administering to the subject, a composition having an amount of a NASP that contains 40% or more fucose saccharide residues. In these embodiments, NASPs of interest may contain 45% or more fucose saccharide residues, such as 50% or more fucose saccharide residues, such as 60% or more fucose saccharide residues, such as 75% or more fucose saccharide residues, such as 85% or more fucose saccharide residues, such as 90% or more fucose saccharide residues, including 95% or more fucose saccharide residues. In other embodiments, NASPs administered to the subject may contain an amount of fucose saccharides residues that ranges, for example from 40 to 99% fucose saccharide residues, such as 40 to 90% fucose saccharide residues, such as 45 to 85% fucose saccharide residues, such as 50 to 80% fucose saccharide residues, such as 50% to 75% fucose saccharide residues, including 50 to 60% fucose saccharide residues.

In certain embodiments, NASPs of interest may contain 40% or more sulfated esters of fucose saccharide residues, such as 50% or more sulfated esters of fucose saccharide residues, such as 60% or more sulfated esters of fucose saccharide residues, such as 75% or more sulfated esters of fucose saccharide residues, such as 85% or more sulfated esters of fucose saccharide residues, such as 90% or more sulfated esters of fucose saccharide residues, including 95% or more sulfated esters of fucose saccharide residues. As described in detail above, sulfated esters of fuose saccharide residues may vary in the amount of sulfation, regioselectivity of sulfation as well as degree of sulfation. For example, sulfated esters of fucose saccharide residues may, in some instances, be monosulfated. In other instances, sulfated esters of fucose saccharide residues may be polysulfated. Likewise, in certain instances, sulfated esters of fucose saccharide residues may be sulfated that the 4-position. On the other hand, sulfated esters of fucose saccharide residues may be sulfated at the 3-position.

In certain embodiments, NASPs of interest contain 40% or more fucose saccharide residues and 20% or more galactose saccharide residues, such as 45% or more fucose saccharide residues and 20% or more galactose residues, such as 50% or more fucose saccharide residues and 20% or more galactose residues, such as 60% or more fucose saccharide residues and 20% or more galactose residues, such as 70% or more fucose saccharide residues and 20% or more galactose residues. In other embodiments, NASPs of interest contain 40% or more fucose saccharide residues and 25% or more galactose saccharide residues, such as 40% or more fucose saccharide residues and 30% or more galactose saccharide residues, and including 40% or more fucose saccharide residues and 40% or more galactose saccharides residues.

As described above, NASPs of the invention may be extracted from a biological source. In some instances NASPs extracted from a biological source may be fucoidans that contain 40% or more fucose saccharide residues. In certain embodiments, fucoidans of interest may include but are not limited to Fucoidan GFS 5508005, *Undaria pinnatifida*, depyrogenated; Fucoidan GFS 5508004, *Undaria pinnatifida*; Fucoidan VG 23, *E. Maxima*; Fucoidan L/FVF1093, *Fucus vesiculosus*, Fucoidan L/FVF1092, *Fucus vesiculosus*; and any combinations thereof.

In certain embodiments, aspects of the invention include enhancing blood coagulation in a subject by administering to the subject, a composition having an amount of a NASP that contains 40% or more fucose saccharide residues in combination with a blood coagulation factor. For example, the subject may be administered an amount of a composition containing a NASP that contains 40% or more fucose saccharide residues and one or more blood coagulation factors which include, but are not limited to factor XI, factor XII, prekallikrein, high molecular weight kininogen (HMWK), factor V, factor VII, factor VIII, factor IX, factor X, factor XIII, factor II, factor VIIa, and von Willebrands factor, factor Xa, factor IXa, factor XIa, factor XIIa, and VIIIa, prekallekrein, and high-molecular weight kininogen, tissue factor, factor VIIa, factor Va, and factor Xa.

Where a composition having a NASP that contains 40% or more fucose saccharide residues and a blood coagulation factor are administered to the subject, the mass ratio of the composition having a NASP that contains 40% or more fucose saccharide residues to blood coagulation factor may vary, and in some instances may range between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the mass ratio of the composition having a NASP that contains 40% or more fucose saccharide residues to blood coagulation factor may range between 1:1 and 1:10; 1:5 and 1:25; 1:10 and 1:50; 1:25 and 1:100; 1:50 and 1:500; or 1:100 and 1:1000. In some embodiments, the mass ratio of the blood coagulation factor to the composition having a NASP that contains 40% or more fucose saccharide residues ranges between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the mass ratio of the blood coagulation factor to the composition having a NASP that contains 40% or more fucose saccharide residues may range between 1:1 and 1:10; 1:5 and 1:25; 1:10 and 1:50; 1:25 and 1:100; 1:50 and 1:500; or 1:100 and 1:1000.

The composition having a NASP that contains 40% or more fucose saccharide residues and the blood coagulation factor may be administered to the subject in any order. In some instances, the composition having a NASP that contains 40% or more fucose saccharide residues is administered prior to administering the blood coagulation factor (i.e., sequentially, on the same day, on different days, etc.). In other instances, the composition having a NASP that contains 40% or more fucose saccharide residues is administered in conjunction with administering the blood coagulation factor. In yet other instances, the composition having a NASP that contains 40% or more fucose saccharide residues is administered after administering the blood coagulation factor (i.e., sequentially, on the same day, on different days, etc.). Where the composition having a NASP that contains 40% or more fucose saccharide residues is administered in conjunction with the blood coagulation factor, the composition having a NASP that contains 40% or more fucose saccharide residues may be mixed with the blood coagulation factor before administering the composition to the subject. Any convenient mixing protocol may be used, such as a by dry shaking, solution or suspension mixing, industrial mixing protocols and the like.

Aspects of the invention also include a method of enhancing blood coagulation in a subject by administering a composition having an amount of a fucoidan, where the fucoidan is extracted from a biological source. In certain embodiments, methods of the invention include administering a composition having an amount of a fucoidan selected from the group consisting of the compounds from Table 1. In these embodiments, fucoidans of interest may include, but are not limited to Fucoidan 5307002, *Fucus vesiculosus*, max. MW peak 126.7 kD; Fucoidan VG49, *Fucus vesiculosus*, hydrolyzed sample of 5307002 of lower MW, max. MW peak 22.5 kD; Fucoidan VG57, *Undaria pinnatifida*, high charge (high sulphation, deacetylated); Fucoidan GFS (5508005), *Undaria pinnatifida*, depyrogenated; Fucoidan GFS (L/FVF-01091), *Fucus vesiculosus*, depyrogenated, max. MW peak 125 kD; Fucoidan GFS (L/FVF-01092), *Fucus vesiculosus*, depyrogenated, max. MW peak 260 kD; Fucoidan GFS (L/FVF-01093), *Fucus vesiculosus*, hydrolyzed depyrogenated, max. MW peak 36 kD; Maritech® *Ecklonia radiata* extract; Maritech® *Ecklonia maxima* extract; Maritech® *Macrocystis pyrifera* extract; Maritech® Immune trial Fucoidan Blend; and combinations thereof.

In these embodiments, aspects of the invention may also include administering the composition having an amount of a fucoidan in combination with a blood coagulation factor. For example, the subject may be administered an amount of a composition containing a fucoidan and one or more blood coagulation factors which include, but are not limited to factor XI, factor XII, prekallikrein, high molecular weight kininogen (HMWK), factor V, factor VII, factor VIII, factor IX, factor X, factor XIII, factor II, factor VIIa, and von Willebrands factor, factor Xa, factor IXa, factor XIa, factor XIIa, and VIIIa, prekallekrein, and high-molecular weight kininogen, tissue factor, factor VIIa, factor Va, and factor Xa.

Where a composition having an amount of a fucoidan and blood coagulation factor are both administered to the subject, the mass ratio of the composition having an amount of a fucoidan to blood coagulation factor may vary, and in some instances may range between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the mass ratio of the composition having an amount of a fucoidan to blood coagulation factor may range between 1:1 and 1:10; 1:5 and 1:25; 1:10 and 1:50; 1:25 and 1:100; 1:50 and 1:500; or 1:100 and 1:1000. In some embodiments, the mass ratio of the blood coagulation factor to the composition having an amount of a fucoidan ranges between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the mass ratio of the blood coagulation factor to the composition having an amount of a fucoidan may range between 1:1 and 1:10; 1:5 and 1:25; 1:10 and 1:50; 1:25 and 1:100; 1:50 and 1:500; or 1:100 and 1:1000.

The composition having an amount of a fucoidan and the blood coagulation factor may be administered to the subject in any order. In some instances, the composition having an amount of a fucoidan is administered prior to administering the blood coagulation factor (i.e., sequentially, on the same day, on different days, etc.). In other instances, the composition having an amount of a fucoidan is administered in conjunction with administering the blood coagulation factor. In yet other instances, the composition having an amount of a fucoidan is administered after administering the blood coagulation factor (i.e., sequentially, on the same day, on different days, etc.). Where the composition having an amount of a fucoidan is administered in conjunction with the blood coagulation factor, the composition having an amount of a fucoidan may be mixed with the blood coagulation factor before administering the composition to the subject. Any convenient mixing protocol may be used, such as a by dry shaking, solution or suspension mixing, industrial mixing protocols and the like.

In certain embodiments of the invention, methods and compositions for treating bleeding disorders using NASPs as procoagulants are provided. NASPs as disclosed herein can be administered alone (i.e., as single agents), or in combination with one another, or with other hemostatic agents. As desired, NASPs of interest may be employed in the treatment of a subject that has been diagnosed as having a bleeding disorder, including congenital coagulation disorders, acquired coagulation disorders, administration of an anticoagulant, and trauma induced hemorrhagic conditions.

In some instances, a subject may be diagnosed as having a blood clotting disorders that includes, but is not limited to hemophilia A, hemophilia B, von Willebrand disease, idiopathic thrombocytopenia, a deficiency of one or more contact factors, such as Factor XI, Factor XII, prekallikrein, and high molecular weight kininogen (HMWK), a deficiency of one or more factors associated with clinically significant bleeding, such as Factor V, Factor VII, Factor VIII, Factor IX, Factor X, Factor XIII, Factor II (hypoprothrombinemia), and von Willebrands factor, a vitamin K deficiency, a disorder of fibrinogen, including afibrinogenemia, hypofibrinogenemia, and dysfibrinogenemia, an alpha$_2$-antiplasmin deficiency, and excessive bleeding such as caused by liver disease, renal disease, thrombocytopenia, platelet dysfunction, hematomas, internal hemorrhage, hemarthroses, surgery, trauma, hypothermia, menstruation, and pregnancy.

In other instances, a subject may be diagnosed as having a blood clotting disorder that includes a congenital coagulation disorder or an acquired coagulation disorder caused by a blood factor deficiency. For example, the blood factor deficiency may be caused by deficiencies of one or more factors, including but not limited to, factor V, factor VII, factor VIII, factor IX, factor XI, factor XII, factor XIII, and von Willebrand factor.

In yet other instances, a subject may be diagnosed as having a blood clotting disorder resulting from the administration of an anticoagulant to the subject. For example, the anticoagulant may include but is not limited to, heparin, a coumarin derivative, such as warfarin or dicumarol, tissue factor pathway inhibitor (TFPI), antithrombin III, lupus anticoagulant, nematode anticoagulant peptide (NAPc2), active-site blocked factor VIIa (factor VIIai), factor IXa inhibitors, factor Xa inhibitors, including fondaparinux, idraparinux, DX-9065a, and razaxaban (DPC906), inhibitors of factors Va and VIIIa, including activated protein C (APC) and soluble thrombomodulin, thrombin inhibitors, including hirudin, bivalirudin, argatroban, and ximelagatran. In certain embodiments, the anticoagulant may be an antibody that binds a clotting factor, including but not limited to, an antibody that binds to Factor V, Factor VII, Factor VIII, Factor IX, Factor X, Factor XIII, Factor II, Factor XI, Factor XII, von Willebrands factor, prekallikrein, or high molecular weight kininogen (HMWK).

In practicing methods of the invention, protocols for enhancing blood coagulation in a subject may vary, such as for example by age, weight, severity of the blood clotting disorder, the general health of the subject, as well as the particular composition and concentration of the NASPs being administered.

In embodiments of the invention, the concentration of NASPs achieved in a subject following administration may vary, in some instances, ranging from 0.01 nM to 500 nM. NASPs of interest are procoagulant at their optimal concentration. By "optimal concentration" is meant the concentration in which NASPs exhibit the highest amount of procoagulant activity. Since many of the NASPs also demonstrated anticoagulant activity at much higher concentrations than the optimal concentration, NASPs of the invention show non-anticoagulant behavior in the range of its optimal concentration. As such, depending on the potency of the NASP as well as the desired effect, the optimal concentration of NASPs provided by methods of the invention may range, from 0.01 nM to 500 nM, such as 0.1 nM to 250 nM, such as 0.1 nM to 100 nM, such as 0.1 nM to 75 nM, such as 0.1 nM to 50 nM, such as 0.1 nM to 25 nM, such as 0.1 nM to 10 nM, and including 0.1 nM to 1 nM. Optimal concentrations and activity level as determined by calibrated automated thrombography (CAT) assay of NASPs of interest are summarized in Tables 2-4 below.

Therefore, the dosage of compositions containing NASPs of interest may vary, ranging from about 0.01 mg/kg to 500 mg/kg per day, such as from 0.01 mg/kg to 400 mg/kg per day, such as 0.01 mg/kg to 200 mg/kg per day, such as 0.1 mg/kg to 100 mg/kg per day, such as 0.01 mg/kg to 10 mg/kg per day, such as 0.01 mg/kg to 2 mg/kg per day, including 0.02 mg/kg to 2 mg/kg per day. In other embodiments, the dosage may range from 0.01 to 100 mg/kg four times per day (QID), such as 0.01 to 50 mg/kg QID, such as 0.01 mg/kg to 10 mg/kg QID, such as 0.01 mg/kg to 2 mg/kg QID, such as 0.01 to 0.2 mg/kg QID. In other embodiments, the dosage may range from 0.01 mg/kg to 50 mg/kg three times per day (TID), such as 0.01 mg/kg to 10 mg/kg TID, such as 0.01 mg/kg to 2 mg/kg TID, and including as 0.01 mg/kg to 0.2 mg/kg TID. In yet other embodiments, the dosage may range from 0.01 mg/kg to 100 mg/kg two times per day (BID), such as 0.01 mg/kg to 10 mg/kg BID, such as 0.01 mg/kg to 2 mg/kg BID, including 0.01 mg/kg to 0.2 mg/kg BID. The amount of compound administered will depend on the potency and concentration of the specific NASP, the magnitude or procoagulant effect desired, as well as the route of administration.

As discussed above, compositions containing a NASP as provided by methods of the invention may be administered in combination with other NASPs or other therapeutic agents, such as hemostatic agents, blood factors, or other medications according to a dosing schedule relying on the judgment of the clinician and needs of the subject. As such, dosing schedules may include, but is not limited to administration five times per day, four times per day, three times per day, twice per day, once per day, three times per week, twice per week, once per week, twice per month, once per month, and any combination thereof.

In some embodiments, the bleeding disorder may be a chronic condition (e.g., a congenital or acquired coagulation factor deficiency) requiring the subject methods and compositions in multiple doses over an extended period. Alternatively, methods and compositions of the invention may be administered to treat an acute condition (e.g., bleeding caused by surgery or trauma, or factor inhibitor/autoimmune episodes in subjects receiving coagulation replacement therapy) in single or multiple doses for a relatively short period, for example one to two weeks.

In practicing embodiments of the invention, one or more therapeutically effective cycles of treatment will be administered to a subject. By "therapeutically effective cycle of treatment" is meant a cycle of treatment that when administered, brings about the desired therapeutic response with respect to treatment. For example, one or more therapeutically effective cycles of treatment may increase the rate of blood clotting as determined by blood clotting assays (e.g., CAT, aPTT, described in detail below) by 1% or more, such as 5% or more, such as 10% or more, such as 15% or more, such as 20% or more, such as 30% or more, such as 40% or more, such as 50% or more, such as 75% or more, such as 90% or more, such as 95% or more, including increasing the rate of blood clot formation by 99% or more. In other instances, one or more therapeutically effective cycles of treatment may increase the rate of blood clot formation by 1.5-fold or more, such as 2-fold or more, such as 5-fold or more, such as 10-fold or more, such as 50-fold or more, including increasing the rate of blood clot formation by 100-fold or more. In some embodiments, subjects treated by methods of the invention exhibit a positive therapeutic response. By "positive therapeutic response" is meant that the subject exhibits an improvement in one or more symptoms of a bleeding disorder. For example, a subject exhibiting a positive therapeutic response to methods provided by the invention may include but is not limited to responses such as shortened blood clotting times, reduced bleeding, reduced need for factor replacement therapy or a combination thereof. In certain embodiments, more than one therapeutically effective cycle of treatment is administered.

As reviewed above, in practicing methods according to certain embodiments, a composition having an amount of a NASP is administered to a subject to enhance blood coagulation in the subject. Any convenient mode of administration may be employed. Modes of administration may include, but are not limited to oral administration, injection (e.g., subcutaneously, intravenously or intramuscularly), intravenous infusion, pulmonary application, rectal application, transdermal application, transmucosal application, intrathecal application, pericardial application, intra-arterial application, intracerebral application, intraocular application, intraperitoneal application or local (i.e., direct) application. As discussed in greater detail below, pharmaceutical compositions of the invention may be in the form of a liquid solution or suspension, syrup, cream, ointment, tablet, capsule, powder, gel, matrix, suppository, or any combination thereof. Where a composition having an amount of a NASP is administered in combination with a blood coagulation factor, as discussed in detail above, the mode of administration of each component may be the same or different. For example, in some instances, the composition having an amount of a NASP may be locally applied (e.g., as a cream), whereas the blood coagulation factor may be administered orally. In other instances, both the composition having an amount of a NASP and the blood coagulation factor are locally applied. In certain embodiments, a composition having an amount of a NASP may be used for localized administration, such as for example, for the treatment of bleeding as a result of a lesion, injury, or surgery. In some instances, a NASP may be administered by injection at the site of bleeding or in the form of a solid, liquid, or ointment, or applied by an adhesive tape.

In certain embodiments, methods of the invention provide for administering a composition having an amount of a NASP prophylactically, such as for example before planned surgery. The composition may be applied prophylactically as desired, such as one hour or more prior to a planned procedure, such as 10 hours prior to a planned procedure, such as 24 hours prior to a planned procedure, and including one week prior to a planned procedure. In some instances, the composition administered prior to or during a planned procedure may be a sustained-release formulation (e.g., transdermal patch, miniature implantable pumps, sustained release caplets or tablets), as described in greater detail below.

In certain embodiments, compositions of the invention can be administered prior to, concurrent with, or subsequent to other agents for treating related or unrelated conditions. If provided at the same time as other agents, compositions of the invention can be provided in the same or in a different composition. Thus, NASPs of interest and other agents can be presented to the individual by way of concurrent therapy. By "concurrent therapy" is intended administration to a subject such that the therapeutic effect of the combination of the substances is caused in the subject undergoing therapy. For example, concurrent therapy may be achieved by administering compositions of the invention and a pharmaceutical composition having at least one other agent, such as a hemostatic agent or coagulation factor (e.g. FVIII or FIX), which in combination comprise a therapeutically effective dose, according to a particular dosing regimen. Similarly, one or more NASPs and therapeutic agents can be administered in at least one therapeutic dose. Administration of the separate pharmaceutical compositions can be performed simultaneously or at different times (i.e., sequentially, in either order, on the same day, or on different days), so long as the therapeutic effect of the combination of these substances is caused in the subject undergoing therapy.

Compositions

Aspects of the invention also include compositions for enhancing blood coagulation in a subject. In embodiments of the invention, compositions include a combination of a NASP and a blood coagulation factor. NASPs for use in the methods of the invention are sulfated polysaccharides that demonstrate procoagulant activity. The non-anticoagulant properties of potential NASPs may be determined using any of the clotting assays described herein, including calibrated automated thrombography (CAT) in Factor VIII and/or Factor IX deficient plasma, dilute prothrombin time (dPT) or activated partial thromboplastin time (aPTT) clotting assays. One measure of noncoagulant activity is to compare the NASP in question with the known anticoagulant heparin. For example, NASPs may exhibit one-third or less, such as one-tenth or less of the anticoagulant activity (measured by statistically significant increase in clotting time) of unfractionated heparin (MW range 8,000 to 30,000; mean 18,000 Daltons). Thus, a NASP can demonstrate at least a two-fold lower anticoagulant activity as compared to heparin, such as a two- to five-fold or lower anticoagulant activity as compared to heparin, and including a two- to 10-fold or lower anticoagulant activity as compared to heparin, using any of the various clotting assays detailed herein.

In some embodiments, compositions of the invention include a NASP having a sulfur content of 8% sulfur or more by weight and a blood coagulation factor. In certain embodiment, the composition has a NASP that has a sulfur content that is 10% sulfur or more by weight, such as 15% sulfur or more by weight, such as 20% sulfur or more by weight, including 25% sulfur or more by weight. In other embodiments, compositions of the invention have NASPs that contain an amount of sulfur that varies, for example ranging from 5 to 25% sulfur by weight, such as 5% to 20% sulfur by weight, such as 5 to 20% sulfur by weight, including 5 to 15% sulfur by weight.

As discussed above, the sulfur content of the NASPs may be present in the form of sulfate. The overall amount of sulfate present in the NASPs may vary. In certain embodiments, the overall amount of sulfate present in NASPs of the invention is 20% sulfate or more by weight, such as 25% sulfate or more by weight, such as 35% sulfate or more by weight, including 50% sulfate or more by weight. In other embodiments, the overall amount of sulfate in the NASPs ranges, for example from 5 to 50% sulfate by weight, such as 5 to 40% sulfate by weight, such as 5 to 30% sulfate by weight, such as 5 to 25% sulfate by weight, such as 10% to 25 sulfate by weight, such as 10 to 20% sulfate by weight, including 10 to 15% sulfate by weight.

Each polysaccharide residue in NASPs of the invention may have varying degrees of sulfation. As discussed above, by "degree of sulfation" is meant the number of sulfate groups bonded to each saccharide residue on the NASP polysaccharide backbone. In some embodiments, each polysaccharide residue (e.g., fucose, galactose, glucose, mannose, xylose as described in detail below) may contain one (i.e., monosulfated) or more (polysulfated) sulfate moieties. For example, in some instances the saccharide residue may be sulfated at the 4-position of the saccharide residue. In other instances the saccharide residue is sulfated at the 3-position. In other instances the saccharide residue is sulfated at the 2-position. In other instances, the saccharide residue is sulfated at the 6-position. In certain instances, the saccharide residue may be sulfated at one or more of the 6-position, the 4-position, the 3-position and the 2-position and any combinations thereof. For example, the saccharide residue may be sulfated at the 4-position and at the 3-position, or at the 4-position and at the 2-position, or at the 3-position and the 2-position, or at the 6-position, 3-position and the 2-position, etc. Each residue may have identical degrees of sulfation (e.g., all saccharide residues being monosulfated) or may have varying degrees of sulfation (e.g., some saccharide residues having identical sulfation and some saccharide residues having different sulfation). For example, 10% or more of the saccharide residues of NASPs of the invention may be monosulfated, such as 15% or more of the saccharide residues, such as 25% or more of the saccharide residues, such as 50% or more of the saccharide residues, such as 75% or more of the saccharide residues, such as 90% or more of the saccharide residues, such as 95% or more of the saccharide residues, including 99% or more of the saccharide residues of NASPs of the invention may be monosulfated. On the other hand, in some embodiments 10% or more of the saccharide residues of NASPs of the invention are polysulfated, such as 15% or more of the saccharide residues, such as 25% or more of the saccharide residues, such as 50% or more of the saccharide residues, such as 75% or more of the saccharide residues, such as 90% or more of the saccharide residues, such as 95% or more of the saccharide residues, including 99% or more of the saccharide residues of NASPs of the invention may be polysulfated. Where both monosulfated and polysulfated saccharide residues are present, the ratio of monosulfated residues to polysulfated residues in NASPs of the invention may vary, and in some instances may range between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the molar ratio of monosulfated residues to polysulfated residues (i.e., monosulfated saccharide residues:polysulfated saccharide residues) in NASPs of interest may range between 1:1 and 1:10; 1:5 and 1:25; 1:10 and 1:50; 1:25 and 1:100; 1:50 and 1:500; or 1:100 and 1:1000. In some embodiments, the ratio of polysulfated residues to monosulfated residues (i.e., polysulfated saccharide residues:monosulfated saccharide residues) in the NASPs ranges between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the ratio of polysulfated saccharide residues to monosulfated residues in NASPs of interest may range between 1:1 and 1:10; 1:5 and 1:25; 1:10 and 1:50; 1:25 and 1:100; 1:50 and 1:500; or 1:100 and 1:1000.

In some embodiments, saccharide residues of NASPs of interest may be sulfated at the 4-position. In other embodiments, the saccharide residues are sulfated at the 3-position. In certain embodiments, the saccharide residues are sulfated at the 4-position and at the 3-position. In other instances the saccharide residue is sulfated at the 2-position. In other instances, the saccharide residue is sulfated at the 6-position. In certain instances, the saccharide residue may be sulfated one or more of the 6-position, the 4-position, the 3-position and the 2-position and any combinations thereof. For example, 10% or more of the saccharide residues of NASPs of the invention may be sulfated at only one of the 6-position, 4-position, 3-position or at the 2-position such as 15% or more of the saccharide residues, such as 25% or more of the saccharide residues, such as 50% or more of the saccharide residues, such as 75% or more of the saccharide residues, such as 90% or more of the saccharide residues, such as 95% or more of the saccharide residues, including 99% or more of the saccharide residues of NASPs of the invention may be sulfated at only one of the 6-position, 4-position, 3-position or at the 2-position. In other embodiments 10% or more of the saccharide residues of NASPs of the invention are sulfated at more than one of the 6-position, 4-position, 3-position and at the 2-position, such as 15% or more of the saccharide residues, such as 25% or more of the saccharide residues, such as 50% or more of the saccharide residues, such as 75% or more of the saccharide residues, such as 90% or more of the saccharide residues, such as 95% or more of the saccharide residues, including 99% or more of the saccharide residues of NASPs of the invention are sulfated at more than one of the 6-position, 4-position, 3-position or at the 2-position. In certain embodiments 10% or more of the saccharide residues of NASPs of the invention are sulfated at both the 3-position and the 4-position, such as 15% or more of the saccharide residues, such as 25% or more of the saccharide residues, such as 50% or more of the saccharide residues, such as 75% or more of the saccharide residues, such as 90% or more of the saccharide residues, such as 95% or more of the saccharide residues, including 99% or more of the saccharide residues of NASPs of the invention are sulfated at both the 3-position and the 4-position. Where both saccharide residues sulfated at the 4-position and saccharide residues sulfated at the 3-position are present, the ratio of saccharide residues sulfated at the 4-position to saccharide residues sulfated at the 3-position may vary, and in some instances may range between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the molar ratio of saccharide residues sulfated at the 4-position to saccharide residues sulfated at the 3-position in NASPs of interest may range between 1:1 and 1:10; 1:5 and 1:25; 1:10 and 1:50; 1:25 and 1:100; 1:50 and 1:500; or 1:100 and 1:1000. In some embodiments, the ratio of saccharide residues sulfated at the 3-position to saccharide residues sulfated at the 4-position in the NASPs ranges between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the ratio of saccharide residues sulfated at the 3-position to saccharide residues sulfated at the 4-position in NASPs of interest may range between 1:1 and 1:10; 1:5 and 1:25; 1:10 and 1:50; 1:25 and 1:100; 1:50 and 1:500; or 1:100 and 1:1000. Any convenient protocol can be employed to determine the type of sulfated saccharide residues of the NASPs, such as described above.

As described in detail above, NASPs of the invention may be extracted from a biological source. In some instances NASPs of interest are fucoidans having a sulfur content of 8% sulfur or more by weight. In certain embodiments, fucoidans having a sulfur content of 8% sulfur or more by weight include, but are not limited to, Fucoidan GFS 5508005, *Undaria pinnatifida*, depyrogenated; Fucoidan GFS 5508004, *Undaria pinnatifida*; Fucoidan GFS 5508003, *Undaria pinnatifida*; Fucoidan 5307002, *Fucus vesiculosus*, max. MW peak 126.7 kD; Fucoidan VG49, *Fucus vesiculosus*, hydrolyzed sample of 5307002 of lower MW, max. MW peak 22.5 kD; Fucoidan 5308004, *Fucus vesiculosus*; Fucoidan 5308005, *Fucus vesiculosus*; Fucoidan L/FVF1091, *Fucus vesiculosus*; Fucoidan VG201096A, *Fucus vesiculosus*; Fucoidan VG201096B, *Fucus vesiculosus*; Fucoidan VG57, *Undaria pinnatifida*, high charge (high sulphation, deacetylated); Fucoidan VG50, *Ascophyllum nodosum*, max. MW peak 149.7 kD; and any combinations thereof.

In addition, compositions of the invention also include one or more blood coagulation factors. For example, compositions of the invention may include an amount of one or more NASPs in combination with one or more blood coagulation factors. Blood coagulation factors of interest include, but are not limited to factor XI, factor XII, prekallikrein, high molecular weight kininogen (HMWK), factor V, factor VII, factor VIII, factor IX, factor X, factor XIII, factor II, factor VIIa, and von Willebrands factor, factor Xa, factor IXa, factor XIa, factor XIIa, and VIIIa, prekallekrein, and high-molecular weight kininogen, tissue factor, factor VIIa, factor Va, and factor Xa.

The amount (i.e., mass) of each of the NASP and blood coagulation factor in compositions of the invention may vary, ranging from 0.001 mg to 1000 mg, such as 0.01 mg to 500 mg, such as 0.1 mg to 250 mg, such as 0.5 mg to 100 mg, such as 1 mg to 50 mg, including 1 mg to 10 mg. As such, in compositions of the invention, the mass ratio of the NASP having a sulfur content that is 8% sulfur or more by weight to blood coagulation factor may vary, and in some instances may range between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the mass ratio of the NASP having a sulfur content that is 8% sulfur or more by weight to blood coagulation factor may range between 1:1 and 1:10; 1:5 and 1:25; 1:10 and 1:50; 1:25 and 1:100; 1:50 and 1:500; or 1:100 and 1:1000. In some embodiments, the mass ratio of the blood coagulation factor to the NASP having a sulfur content that is 8% sulfur or more by weight ranges between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the mass ratio of the blood coagulation factor to the composition that contains a NASP having a sulfur content that is 8% sulfur or more by weight may range between 1:1 and 1:10; 1:5 and 1:25; 1:10 and 1:50; 1:25 and 1:100; 1:50 and 1:500; or 1:100 and 1:1000.

In other embodiments, compositions of the invention include a NASP having 40% or more fucose saccharide residues and a blood coagulation factor. As described above, the saccharide content of NASPs may vary. In some instances, the saccharide content of NASPs of interest may include, but is not limited to fucose residues, xylose residues, galactose residues, glucose residues, mannose residues, rhamnose residues, arabinose residues and uronic acid. In some embodiments, NASPs of interest are composed of two or more of fucose residues, xylose residues, galactose residues, glucose residues, mannose residues, rhamnose residues, arabinose residues and uronic acid. The amount of each saccharide residue in NASPs of interest may vary. For example, 40% or more of the saccharide residues of NASPs of the invention may be fucose saccharide residues, such as 45% or more of the saccharide residues, such as 50% or more of the saccharide residues, such as 55% or more of the saccharide residues, such as 65% or more of the saccharide residues, such as 75% or more of the saccharide residues, such as 90% or more of the saccharide residues, including 99% or more of the saccharide residues of NASPs of the invention may be fucose saccharide residues. In other instances, 1% or more of the saccharide residues of NASPs of the invention may be galactose saccharide residues, such as 5% or more of the saccharide residues, such as 10% or more of the saccharide residues, such as 15% or more of the saccharide residues, such as 20% or more of the saccharide residues, including 25% or more of the saccharide residues of NASPs of the invention may be galactose saccharide residues. In yet other instances, 1% or more of the saccharide residues of NASPs of the invention may be uronic acid saccharide residues, such as 5% or more of the saccharide residues, such as 10% or more of the saccharide residues, such as 15% or more of the saccharide residues, such as 20% or more of the saccharide residues, including 25% or more of the saccharide residues of NASPs of the invention may be uronic acid saccharide residues.

In embodiments of the invention, NASPs of interest may be a linear (i.e., unbranched) polysaccharide or may be a branched polysaccharide. In certain instances, NASPs may have portions of its structure that is linear and other parts of its structure that is branched. As discussed above, a linear polysaccharide is a polysaccharide or part of a polysaccharide that contains only α-1,4 glycosidic bonds or α-1,3 glycosidic bonds, or alternating α-1,3/α-1,4 glycosidic bonds and a branched polysaccharide is a polysaccharide or part of a polysaccharide that contains two or more glycosidic bonds to other saccharide residues, where one of the glycosidic bonds is an α-1,4-glycosidic bond or α-1,3 glycosidic bonds, or alternating α-1,3/α-1,4 glycosidic bonds and the other is an α-1,6-glycosidic bond. The amount of branching in the structure of NASPs of interest may vary.

In some embodiments, compositions of the invention include a NASP that contains 40% or more fucose saccharide residues. For example, NASPs of interest may contain 45% or more fucose saccharide residues, such as 50% or more fucose saccharide residues, such as 60% or more fucose saccharide residues, such as 75% or more fucose saccharide residues, such as 85% or more fucose saccharide residues, such as 90% or more fucose saccharide residues, including 95% or more fucose saccharide residues. In certain embodiments, NASPs of interest may contain 40% or more sulfated esters of fucose saccharide residues, such as 50% or more sulfated esters of fucose saccharide residues, such as 60% or more sulfated esters of fucose saccharide residues, such as 75% or more sulfated esters of fucose saccharide residues, such as 85% or more sulfated esters of fucose saccharide residues, such as 90% or more sulfated esters of fucose saccharide residues, including 95% or more sulfated esters of fucose saccharide residues. As described in detail above, sulfated esters of fuose saccharide residues may vary in the amount of sulfation, regioselectivity of sulfation as well as degree of sulfation. For example, sulfated esters of fucose saccharide residues may, in some instances, be monosulfated. In other instances, sulfated esters of fucose saccharide residues may be polysulfated. Likewise, in certain instances, sulfated esters of fucose saccharide residues may be sulfated that the 4-position. On the other hand, sulfated esters of fucose saccharide residues may be sulfated at the 3-position.

In certain embodiments, NASPs of interest contain 40% or more fucose saccharide residues and 20% or more galactose saccharide residues, such as 45% or more fucose saccharide residues and 20% or more galactose residues, such as 50% or more fucose saccharide residues and 20% or more galactose residues, such as 60% or more fucose saccharide residues and 20% or more galactose residues, such as 70% or more fucose saccharide residues and 20% or more galactose residues. In other embodiments, NASPs of interest contain 40% or more fucose saccharide residues and 25% or more galactose saccharide residues, such as 40% or more fucose saccharide residues and 30% or more galactose saccharide residues, and including 40% or more fucose saccharide residues and 40% or more galactose saccharides residues.

As described in detail above, NASPs of the invention may be extracted from a biological source. In some instances NASPs of interest are fucoidans that contain 40% or more fucose saccharide residues. In certain embodiments, fucoidans of interest may include but are not limited to Fucoidan GFS 5508005, *Undaria pinnatifida*, depyrogenated; Fucoidan GFS 5508004, *Undaria pinnatifida*; Fucoidan VG 23, *E. Maxima*; Fucoidan L/FVF1093, *Fucus vesiculosus*, Fucoidan L/FVF1092, *Fucus vesiculosus*; and any combinations thereof.

Compositions of the invention also include one or more blood coagulation factors in addition to a NASP having 40% or more fucose saccharide residues. For example, compositions of the invention may include an amount of one or more NASPs in combination with one or more blood coagulation factors. Blood coagulation factors of interestinclude, but are not limited to factor XI, factor XII, prekallikrein, high molecular weight kininogen (HMWK), factor V, factor VII, factor VIII, factor IX, factor X, factor XIII, factor II, factor VIIa, and von Willebrands factor, factor Xa, factor IXa, factor XIa, factor XIIa, and VIIIa, prekallekrein, and high-molecular weight kininogen, tissue factor, factor VIIa, factor Va, and factor Xa.

The amount (i.e, mass) of each of the NASPs and blood coagulation factor in compositions of the invention may vary, ranging from 0.001 mg to 1000 mg, such as 0.01 mg to 500 mg, such as 0.1 mg to 250 mg, such as 0.5 mg to 100 mg, such as 1 mg to 50 mg, including 1 mg to 10 mg. As such, in compositions of the invention, the mass ratio of the NASP having 40% or more fucose saccharide residues to blood coagulation factor may vary, and in some instances may range between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the mass ratio of the NASP having 40% or more fucose saccharide residues to blood coagulation factor may range between 1:1 and 1:10; 1:5 and 1:25; 1:10 and 1:50; 1:25 and 1:100; 1:50 and 1:500; or 1:100 and 1:1000. In some embodiments, the mass ratio of the blood coagulation factor to the NASP having 40% or more fucose saccharide residues ranges between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the mass ratio of the blood coagulation factor to the composition that contains a NASP having 40% or more fucose saccharide residues may range between 1:1 and 1:10; 1:5 and 1:25; 1:10 and 1:50; 1:25 and 1:100; 1:50 and 1:500; or 1:100 and 1:1000.

In certain embodiments, compositions of the invention include fucoidans. Fucoidans are naturally-occurring complex sulfated polysaccharides compounds which may be extracted from certain edible seaweeds, brown algae and echinoderms (e.g., sea urchins, sea cucumbers). As used herein the term, "fucoidan" refers to a diverse group of moieties extracted from a biological source of low sulfate polymers rather than a single chemical entity. Fucoidan from various species of brown algae and echinoderm differ in the amount of fucose in their backbone, the degree and pattern of sulfation, structure (linear versus branching), and proportions of individual saccharides and uronic acid.

Fucoidans for use in the present invention may be extracted, further purified and/or modified from natural sources (e.g. brown algae). Fucoidans can be isolated from algae by hot water, by acid or ethanol extraction, or by enzymatic digestion, followed by isolation from aqueous solution by precipitation (e.g., by addition of organic solvents) or ultrafiltered.

Fucoidans in the present invention may be extracted from organisms from the genus *Fucus, Laminaria, Cladosiphon, Namacystus, Undaria, Chordaria, Sargassum, Leathesia, Desmarestia, Dictyosiphon, Dictyota, Padina, Spatoglossum, Adenocystis, Pylayella, Ascophyllum, Bifurcaria, Himanthalia, Hizikia, Pelvetia, Alaria, Arthrothamnus, Chorda, Ecklonia, Eisenia, Macrocystis, Nereocystis, Petalonia, Scytosiphon*, and *Saundersella*, among others.

Fucoidans described herein may be heterogeneous mixtures of fucoidans varying in sulfur content, degree of sulfation, saccharide content and molecular weight.

Fucoidans of interest may range in average molecular weight from about 10 daltons to about 500,000 daltons, such as from about 100 daltons to about 300,000 daltons, such as from 1000 daltons to 250,000 daltons, including 1000 daltons to 150,000 daltons. Molecular weights of fucoidan can be determined by any convenient protocol, such as for example, gel permeation chromatography or high-performance size-exclusion chromatography (HPSEC), capillary electrophoresis, PAGE (polyacrylamide gel electrophoresis), agarose gel electrophoresis, among others.

In some embodiments, fucoidans of interest may be heterogeneous mixtures of sulfated polysaccharides having varying molecular weights. For example, in some instances, 5% or more of the fucoidan composition has a molecular weight that ranges from 10 to 30,000 daltons, such as 10% or more, such as 25% or more, such as 50% or more, such as 75% or more, such as 90% or more, including 95% or more of the fucoidan composition has a molecular weight that ranges from 10 to 30,000 daltons. In other embodiments, 5% or more of the fucoidan composition has a molecular weight that ranges from 30,000 daltons to 75,000 daltons, such as 10% or more, such as 25% or more, such as 50% or more, such as 75% or more, such as 90% or more, including 95% or more of the fucoidan composition has a molecular weight that ranges from 30,000 to 75,000 daltons. In yet other embodiments, 5% or more of the fucoidan composition has a molecular weight that are greater than 75,000 daltons, such as 10% or more, such as 25% or more, such as 50% or more, such as 75% or more, such as 90% or more, including 95% or more of the fucoidan composition has a molecular weight that is greater than 75,000 daltons.

In certain embodiments, low molecular weight fucoidans may be employed for enhancing blood coagulation as provided by methods and compositions of the invention. By "low molecular weight fucoidan" is meant a fucoidan having a weight average molecular weight that ranges from about 10 to 30,000 daltons, such as for example 100 to 30,000 daltons, such as 500 to 25,000 daltons, including 1000 to 15,000 daltons. Examples of low molecular weight fucoidans may include, but are not limited to naturally occurring fucoidans having a molecular weight ranging from 10 to 30,000 daltons, fragments of larger molecular weight fucoidans produced by acid or enzyme hydrolysis of the larger molecular weight fucoidan, or may be isolated fractions having molecular weights ranging from 10 to 30,000 daltons from a fractionated fucoidan sample.

In some embodiments, fucoidans extracted from a biological source may be fractionated to isolate low molecular weight fucoidans (i.e., fractions containing fucoidans having molecular weight ranging from 10-30,000 daltons). Any convenient protocol may be used to fractionate fucoidans of interest, including but not limited to size exclusion chromotagraphy, gel permeation chromatography, capillary electrophoresis, among others.

In certain instances, low molecular weight fucoidans obtained by fractionating a fucoidan sample may be employed for enhancing blood coagulation as provided by the methods and compositions of the invention. For example, fucoidans extracted from a biological source may be fractionated to isolate fucoidans having molecular weights that range from 10 to 30,000 daltons, such as 10 to 5000 daltons, such as 5000 to 10,000 daltons, such as 10,000 to 15,000 daltons, and including 15,000 to 30,000 daltons. In certain embodiments, one or more of these fractions may be administered for enhancing blood coagulation in a subject, such as by the methods described above.

In certain embodiments, different molecular weight fractions may be prepared by acid-hydrolysis or radical depolymerization of high molecular weight fucoidan. The molecular weight ranges of the resulting products may be adjusted based upon the stringency of the hydrolysis or depolymerization conditions employed. Fractions may then be further purified using ion exchange chromatography. For instance, to obtain middle and low molecular weight fractions of fucoidan, high molecular weight fucoidan may be hydrolyzed using an acid such as HCl (or any other suitable acid) at concentrations ranging from 0.02 to 1.5 M and at temperatures ranging from 25° C. to 80° C. Hydrolysis reaction times will typically range from 15 minutes to several hours. The resulting hydrolyzed reaction mixture is then neutralized by addition of base (e.g., sodium hydroxide). Salts are subsequently removed, for example, by electrodialysis, and the hydrolysis products are analyzed to determine weight average molecular weight, saccharide content, and sulfur content, using conventional analytical techniques for carbohydrate analysis. Alternatively, enzymatic methods may be employed to degrade fucoidans using, e.g., glycosidases such as fucan sulfate hydrolase (fucoidanase EC 3.2.1.44) and α-L-fucosidase EC 3.2.1.51. Fucoidans for use in the invention may be heterogeneous or homogeneous, depending upon the degree of separation employed.

In certain embodiments, compositions of the invention include a blood coagulation factor in combination with a fucoidan extracted from a biological source, such as for example, Fucoidan 5307002, *Fucus vesiculosus*, max. MW peak 126.7 kD; Fucoidan VG49, *Fucus vesiculosus*, hydrolyzed sample of 5307002 of lower MW, max. MW peak 22.5 kD; Fucoidan VG57, *Undaria pinnatifida*, high charge (high sulfation, deacetylated); Fucoidan GFS (5508005), *Undaria pinnatifida*, depyrogenated; Fucoidan GFS (L/FVF-01091), *Fucus vesiculosus*, depyrogenated, max. MW peak 125 kD; Fucoidan GFS (L/FVF-01092), *Fucus vesiculosus*, depyrogenated, max. MW peak 260 kD; Fucoidan GFS (L/FVF-01093), *Fucus vesiculosus*, hydrolyzed depyrogenated, max. MW peak 36 kD; Maritech® *Ecklonia radiata* extract; Maritech® *Ecklonia maxima* extract; Maritech® *Macrocystis pyrifera* extract; Maritech® Immune trial Fucoidan Blend; and any combinations thereof.

As described above, fucoidans of interest may be extracted from a biological source. In some instances, crude fucoidan compositions extracted from a biological source may also contain impurities. By "impurities" is meant any component of the crude fucoidan composition which may be undesirable or is detrimental to the fucoidan composition. For example, impurities may interfere (i.e., diminish) or inhibit a particular desirable property of fucoidans of the invention, such as for example procoagulant activity. In other embodiments, impurities may not be detrimental to the function of the fucoidan composition, but may result in the fucoidan composition being unsuitable for administration to a subject, such as for example containing elevated levels of toxins, bacteria content or high levels of trace metal ions (e.g., arsenic, lead, cadmium or mercury) as described below. Impurities may include, but are not limited to residual moisture, protein, endotoxins, alginate, uronic acids, trace elements and metal ions.

The amount of protein impurities present in extracted fucoidan compositions of the invention may vary, ranging from 0.2% to 6% by weight, such as 0.25% to 5% by weight, such as 0.5% to 2.5% by weight, including 1.0% to 2.0% by weight. Further, endotoxin levels in extracted fucoidan compositions may also vary, ranging from 0.1 EU/mg to 75 EU/mg, such as 0.5 EU/mg to 50 EU/mg, such as 1 EU/mg to 25 EU/mg, including 5 EU/mg to 10 EU/mg. The residual moisture content of extracted fucoidan compositions of the invention may also vary, ranging from 5% to 20%, such as 5% to 15%, including 5% to 10%.

In some embodiments, impurities may include uronic acids. Uronic acids may be present in extracted fucoidan compositions of the invention in an amount that varies, ranging from 1% to 60% by weight, such as 5% to 50% by weight, such as 10% to 40% by weight, and including 15% to 25% by weight. Uronic acid impurities may be detected and quantified using any convenient protocol, such as for example, Carbazole Assay or nuclear magnetic resonance spectroscopy.

In some embodiments, impurities may include trace elements and metal ions. Trace elements and metal ions may include, but are not limited to aluminum, arsenic, bromine, cadmium, cerium, chromium, cobalt, iodine, lead, lithium, manganese, mercury, molybdenum, nickel, phosphorus, rubidium, tin, tungsten, uranium, vanadium. Trace elements and metal ions (e.g., As, Cd Hg, Pb) may be present in extracted fucoidan compositions of the invention in an amount that varies, ranging from 0.05 µg/g to 3.0 µg/g, such as 0.1 µg/g to 2.5 µg/g, such as 0.25 µg/g to 2.0 µg/g, and including 0.5 µg/g to 1.5 µg/g. Trace elements and metal ions may be detected using any convenient protocol, such as for example mass spectrometry, inductively coupled plasma, ion chromatography, gas chromatography, atomic absorption, graphite furnace atomic absorption spectrometry, inductively coupled plasma mass spectrometry, inductively coupled plasma atomic emission spectrometry, flame atomic absorption spectrometry, acidimetric titration, or any combination thereof.

In some embodiments, fucoidan compositions extracted from a biological source may be purified prior to administering to a subject. Impurities in fucoidan compositions may be purified using any convenient protocol. Methods for removing impurities and purifying a fucoidan composition extracted from a biological source is described in detail in co-pending U.S. patent application Ser. No. 12/449,712, filed Feb. 25, 2010, the disclosure of which is herein incorporated by reference.

Blood coagulation factors which are administered in combination with NASPs of interest may include, but are not limited to factor XI, factor XII, prekallikrein, high molecular weight kininogen (HMWK), factor V, factor VII, factor VIII, factor IX, factor X, factor XIII, factor II, factor VIIa, and von Willebrands factor, factor Xa, factor IXa, factor XIa, factor XIIa, and VIIIa, prekallekrein, and high-molecular weight kininogen, tissue factor, factor VIIa, factor Va, and factor Xa.

The amount (i.e., mass) of each of the fucoidan and blood coagulation factor in compositions of the invention may vary, ranging from 0.001 mg to 1000 mg, such as 0.01 mg to 500 mg, such as 0.1 mg to 250 mg, such as 0.5 mg to 100 mg, such as 1 mg to 50 mg, including 1 mg to 10 mg. As such, in compositions of the invention, the mass ratio of the fucoidan to blood coagulation factor may vary, and in some instances may range between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the mass ratio of the fucoidan to blood coagulation factor may range between 1:1 and 1:10; 1:5 and 1:25; 1:10 and 1:50; 1:25 and 1:100; 1:50 and 1:500; or 1:100 and 1:1000. In some embodiments, the mass ratio of the blood coagulation factor to the fucoidan ranges between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the mass ratio of the blood coagulation factor to the fucoidan may range between 1:1 and 1:10; 1:5 and 1:25; 1:10 and 1:50; 1:25 and 1:100; 1:50 and 1:500; or 1:100 and 1:1000.

Compositions of the invention may be homogeneous, containing only a single type of NASP. In other embodiments, compositions of interest are heterogenous mixtures of two or more NASPs. For example, heterogenous mixtures may contain two or more NASPs that vary with respect to monosaccharide content, sulfur content, degree of sulfation as well as NASPs having heterogenous or homogeneous distributions of molecular weight. In some instances, compositions of the invention are fucoidans that have low molecular weight. In other instances, compositions of the invention are composed of fucoidans having a broad range of molecular weight.

In certain embodiments, compositions of the invention may further include one or more pharmaceutically acceptable excipients as part of a pharmaceutical composition. Excipients may include, but are not limited to, carbohydrates, inorganic salts, antimicrobial agents, antioxidants, surfactants, buffers, acids, bases, and any combinations thereof. Excipients suitable for injectable compositions may include water, alcohols, polyols, glycerine, vegetable oils, phospholipids, and surfactants. A carbohydrate such as a sugar, a derivatized sugar such as an alditol, aldonic acid, an esterified sugar, and/or a sugar polymer may also be employed. Some carbohydrate excipients of interest include, for example, monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like. Inorganic salts may include, but are not limited to citric acid, sodium chloride, potassium chloride, sodium sulfate, potassium nitrate, sodium phosphate monobasic, sodium phosphate dibasic, and any combinations thereof.

In certain embodiments, compositions of the invention may also include an antimicrobial agent for preventing or deterring microbial growth, such as for example benzalkonium chloride, benzethonium chloride, benzyl alcohol, cetylpyridinium chloride, chlorobutanol, phenol, phenylethyl alcohol, phenylmercuric nitrate, thimersol, and any combinations thereof.

One or more antioxidants may also be employed. Antioxidants, which can reduce or prevent oxidation and thus deterioration of the composition, may include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and any combinations thereof.

One or more surfactants may also be included in compositions of the invention. For example, suitable surfactants may include, but are not limited to polysorbates, such as "Tween 20" and "Tween 80," and pluronics such as F68 and F88 (BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; chelating agents, such as EDTA; and zinc and other cations.

Acids or bases may also be present in compositions of the invention. For example, acids may include but are not limited to hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and any combinations thereof. Examples bases include, but are not limited to sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and any combinations thereof.

The amount of any individual excipient in the composition will vary depending on the nature and function of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects. Generally, however, the excipient(s) will be present in the composition in an amount of about 1% to about 99% by weight, such as from about 5% to about 98% by weight, such as from about 15 to about 95% by weight of the excipient, including less than 30% by weight. Pharmaceutical excipients along with other excipients that may be employed in compositions of the invention are described in "Remington: The Science & Practice of Pharmacy", 19th ed., Williams & Williams, (1995), the "Physician's Desk Reference", 52nd ed., Medical Economics, Montvale, N.J. (1998), and Kibbe, A. H., Handbook of Pharmaceutical Excipients, 3rd Edition, American Pharmaceutical Association, Washington, D.C., 2000, the disclosure of which is herein incorporated by reference.

As described above, compositions of the invention may be administered by any convenient mode of administration. As such, the formulation may vary. For example, compositions of the invention may be an injection, e.g., powders or lyophilates that can be reconstituted with a solvent prior to use, as well as ready for injection solutions or suspensions, dry insoluble compositions for combination with a vehicle prior to use, and emulsions and liquid concentrates for dilution prior to administration. In embodiments where compositions of the invention are employed for injections, diluents for reconstituting solid compositions prior to injection may include, but is not limited to bacteriostatic water for injection, dextrose 5% in water, phosphate buffered saline, Ringer's solution, saline, sterile water, deionized water, and any combinations thereof. In some embodiments, pharmaceutical compositions of the invention may be in the form of a liquid solution or suspension, syrup, cream, ointment, tablet, capsule, powder, gel, matrix, suppository, or any combination thereof.

Compositions of the invention may be pre-loaded into a syringe, an implantation device, or the like, depending upon the intended mode of delivery and use. In certain embodiments, the compositions are in unit dosage form, such that an amount of the composition is ready in a single dose, in a premeasured or pre-packaged form.

Utility

The subject methods and compositions find use in any situation where there is a desire to enhance blood coagulation in a subject and the subject is responsive to treatment with a NASP. In certain embodiments, the subject methods and compositions may be employed to treat bleeding disorders, such as a chronic or acute bleeding disorder, a congenital coagulation disorder caused by a blood factor deficiency, an acquired coagulation disorder and administration of an anticoagulant. For example, bleeding disorders may include, but are not limited to hemophilia A, hemophilia B, von Willebrand disease, idiopathic thrombocytopenia, a deficiency of one or more contact factors, such as Factor XI, Factor XII, prekallikrein, and high molecular weight kininogen (HMWK), a deficiency of one or more factors associated with clinically significant bleeding, such as Factor V, Factor VII, Factor VIII, Factor IX, Factor X, Factor XIII, Factor II (hypoprothrombinemia), and von Willebrands factor, a vitamin K deficiency, a disorder of fibrinogen, including afibrinogenemia, hypofibrinogenemia, and dysfibrinogenemia, an alpha$_2$-antiplasmin deficiency, and excessive bleeding such as caused by liver disease, renal disease, thrombocytopenia, platelet dysfunction, hematomas, internal hemorrhage, hemarthroses, surgery, trauma, hypothermia, menstruation, and pregnancy.

The subject methods and compositions also find use in enhancing blood coagulation to treat a congenital coagulation disorder or an acquired coagulation disorder caused by a blood factor deficiency. The blood factor deficiency may be caused by deficiencies of one or more factors, including but not limited to, factor V, factor VII, factor VIII, factor IX, factor XI, factor XII, factor XIII, and von Willebrand factor.

The subject methods and compositions also find use in enhancing blood coagulation in order to improve hemostasis in treating bleeding disorders, such as those associated with deficiencies of coagulation factors or for reversing the effects of anticoagulants in a subject. For example, enhancing blood coagulation by methods and compositions of the invention may be employed to to treat bleeding disorders such as congenital coagulation disorders, acquired coagulation disorders, and hemorrhagic conditions induced by trauma. Examples of bleeding disorders that may be treated with NASPs include, but are not limited to, hemophilia A, hemophilia B, von Willebrand disease, idiopathic thrombocytopenia, a deficiency of one or more contact factors, such as Factor XI, Factor XII, prekallikrein, and high molecular weight kininogen (HMWK), a deficiency of one or more factors associated with clinically significant bleeding, such as Factor V, Factor VII, Factor VIII, Factor IX, Factor X, Factor XIII, Factor II (hypoprothrombinemia), and von Willebrands factor, a vitamin K deficiency, a disorder of fibrinogen, including afibrinogenemia, hypofibrinogenemia, and dysfibrinogenemia, an alpha$_2$-antiplasmin deficiency, and excessive bleeding such as caused by liver disease, renal disease, thrombocytopenia, platelet dysfunction, hematomas, internal hemorrhage, hemarthroses, surgery, trauma, hypothermia, menstruation, and pregnancy. In certain embodiments, methods and compositions of the invention are used to treat congenital coagulation disorders including hemophilia A, hemophilia B, and von Willebrands disease. In other embodiments, NASPs are used to treat acquired coagulation disorders, including deficiencies of factor VIII, von Willebrand factor, factor IX, factor V, factor XI, factor XII and factor XIII, particularly disorders caused by inhibitors or autoimmunity against blood coagulation factors, or haemostatic disorders caused by a disease or condition that results in reduced synthesis of coagulation factors.

In some embodiments, the bleeding disorder may be a chronic condition (e.g., a congenital or acquired coagulation factor deficiency) requiring the subject methods and compositions in multiple doses over an extended period. Alternatively, methods and compositions of the invention may be administered to treat an acute condition (e.g., bleeding caused by surgery or trauma, or factor inhibitor/autoimmune episodes in subjects receiving coagulation replacement therapy) in single or multiple doses for a relatively short period, for example one to two weeks.

The subject methods and compositions also find use in enhancing blood coagulation in a subject undergoing a surgical or invasive procedure.

The subject methods and compositions also find use in enhancing blood coagulation in order to reverse the effects of an anticoagulant in a subject, the method comprising administering a therapeutically effective amount of a composition comprising a NASP to the subject. In certain embodiments, the subject may have been treated with an anticoagulant including, but not limited to, heparin, a coumarin derivative, such as warfarin or dicumarol, TFPI, AT III, lupus anticoagulant, nematode anticoagulant peptide (NAPc2), active-site blocked factor VIIa (factor VIIai), factor IXa inhibitors, factor Xa inhibitors, including fondaparinux, idraparinux, DX-9065a, and razaxaban (DPC906), inhibitors of factors Va and VIIIa, including activated protein C (APC) and soluble thrombomodulin, thrombin inhibitors, including hirudin, bivalirudin, argatroban, and ximelagatran. In certain embodiments, the anticoagulant in the subject may be an antibody that binds a clotting factor, including but not limited to, an antibody that binds to Factor V, Factor VII, Factor VIII, Factor IX, Factor X, Factor XIII, Factor II, Factor XI, Factor XII, von Willebrands factor, prekallikrein, or high molecular weight kininogen (HMWK).

In another aspect, the invention provides a method for treating a subject undergoing a surgical or invasive procedure wherein improved blood clotting would be desirable, comprising administering a therapeutically effective amount of a composition comprising a NASP as detailed herein to the subject. In certain embodiments, the NASP can be coadministered with one or more different NASPs and/or in combination with one or more other therapeutic agents to the subject undergoing a surgical or invasive procedure. For example, the subject may be administered a therapeutically effective amount of one or more factors selected from the group consisting of factor XI, factor XII, prekallikrein, high molecular weight kininogen (HMWK), factor V, factor VII, factor VIII, factor IX, factor X, factor XIII, factor II, factor VIIa, and von Willebrands factor. Treatment may further comprise administering a procoagulant, such as an activator of the intrinsic coagulation pathway, including factor Xa, factor IXa, factor XIa, factor XIIa, and VIIIa, prekallekrein, and high-molecular weight kininogen; or an activator of the extrinsic coagulation pathway, including tissue factor, factor VIIa, factor Va, and factor Xa. Therapeutic agents used to treat a subject undergoing a surgical or invasive procedure can be administered in the same or different compositions and concurrently, before, or after administration of the NASP.

In another aspect, the invention provides a method of measuring acceleration of clotting by a NASP as detailed herein in a biological sample, the method including: combining the biological sample with compositions of the invention; measuring the clotting time of the biological sample; comparing the clotting time of the biological sample to the clotting time of a corresponding biological sample not exposed to compositions of the invention, wherein a decrease in the clotting time of the biological sample exposed to the NASP, if observed, is indicative of a NASP that accelerates clotting.

As disclosed above, hemostatic agents, blood factors, and medications may also be employed. For example, the subject may be administered one or more blood coagulation factors such as factor XI, factor XII, prekallikrein, high molecular weight kininogen (HMWK), factor V, factor VII, factor VIII, factor IX, factor X, factor XIII, factor II, factor VIIa, von Willebrands factor, factor Xa, factor IXa, factor XIa, factor XIIa, and VIIIa, prekallekrein, and high-molecular weight kininogen, tissue factor, factor VIIa, factor Va, and factor Xa.

Kits

Also provided are kits for use in practicing the subject methods, where the kits may include one or more of the above compositions, e.g., an NASP composition and/or blood coagulation factor, as described above. The kit may further include other components, e.g., administration devices, fluid sources, syringes, needles etc., which may find use in practicing the subject methods. Various components may be packaged as desired, e.g., together or separately.

In addition to above mentioned components, the subject kits may further include instructions for using the components of the kit to practice the subject methods. The instructions for practicing the subject methods are generally recorded on a suitable recording medium. For example, the instructions may be printed, such as on paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

EXPERIMENTAL

The following examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Clotting Assays

The ability of NASPs to promote clotting and reduce bleeding is determined using various in vitro clotting assays (e.g., dPT and aPTT assays) and in vivo bleeding models (e.g. tail snip or cuticle bleeding time determination in hemophilic mice or dogs). Clotting assays may be performed in the presence of compositions of the invention, including NASPs of interest and one or more blood factors, procoagulants, or other reagents. For example, one or more factors can be added, include but are not limited to, factor XI, factor XII, prekallikrein, high molecular weight kininogen (HMWK), factor V, factor VII, factor VIII, factor IX, factor X, factor XIII, factor II, and von Willebrands factor, tissue factor, factor VIIa, factor Va, and factor Xa, factor IXa, factor XIa, factor XIIa, and VIIIa; and/or one or more reagents, including but not limited to, APTT reagent, thromboplastin, fibrin, TFPI, Russell's viper venom, micronized silica particles, ellagic acid, sulfatides, and kaolin.

Compositions of the present invention show anticoagulant activity only at concentrations significantly above the concentration at which they exhibit procoagulant activity. The ratio of the concentration at which undesired anticoagulant properties occur to the concentration at which desired procoagulant activities occur is referred to as the procoagulant index. The procoagulant index for compositions of the present invention may be 5 or more, such as 10 or more, such as 30 or more, such as 100 or more, such as 300 or more, and including 1000 or more.

Calibrated Automated Thrombography (CAT) Assay

In the CAT studies, the procoagulant activity of sulfated polysaccharides was examined in several plasmas from patients with congenital coagulation factor deficiencies and FVIII-inhibited normal plasma, in order to study the procoagulant window. Pooled normal plasma or plasmas from patients with congenital coagulation factor deficiencies were obtained from George King, Bio-Medical Inc. Kansas USA. According to the supplier, the residual coagulation factor activity for each of the coagulation factor deficient plasmas was lower than 1%. As a model for antibody mediated FVIII deficiency fresh frozen pooled normal plasma (George King, Bio-Medical Inc., Kansas, USA) was incubated with high titer heat inactivated anti-human FVIII plasma raised in goat (4490 BU/ml; Baxter BioScience, Vienna, Austria) giving rise to 50 BU/mL. In some experiments, tissue factor pathway inhibitor (TFPI) activity was blocked in presence or absence of the fucoidan by either a polyclonal goat anti-human TFPI antibodies (R&D Systems, AF2974, Minneapolis, US) or a monoclonal anti-TFPI antibody directed against the positively charged C-terminus of TFPI (Sanquin White Label Products, MW1848, clone CLB/TFPI C-terminus, Amsterdam, The Netherlands) at plasma concentration of 25 nM or 100 nM, respectively. If not indicated otherwise, the plasmas were mixed with corn trypsin inhibitor (CTI) (Hematologic Technologies, Inc., Essex Junction, Vt., USA), providing a final concentration of 40 μg/mL, for specific inhibition of factor XIIa.

Test samples were prepared by dissolving quantities of NASPs of interest in Hepes buffered saline and adding human serum albumin (Sigma-Aldrich Corporation, St. Louis, Mo., USA) to a concentration of 5 mg/mL. Reference samples were prepared from reference proteins FVIII Immunate® reference standard (Baxter BioScience, Vienna, Austria); Factor eight inhibitor by-passing activity (FEIBA) reference standard (Baxter BioScience, Vienna, Austria); NovoSeven® recombinant activated FVII (Novo Nordisk A/S, Denmark) and purified human plasma FIX (Enzyme Research Laboratories, South Bend, Ill., USA). A thrombin calibrator compound was obtained from Thrombinoscope BV, Maastricht, The Netherlands.

Activated Partial Thromboplastin Time (aPTT) Assay

Figure 3:
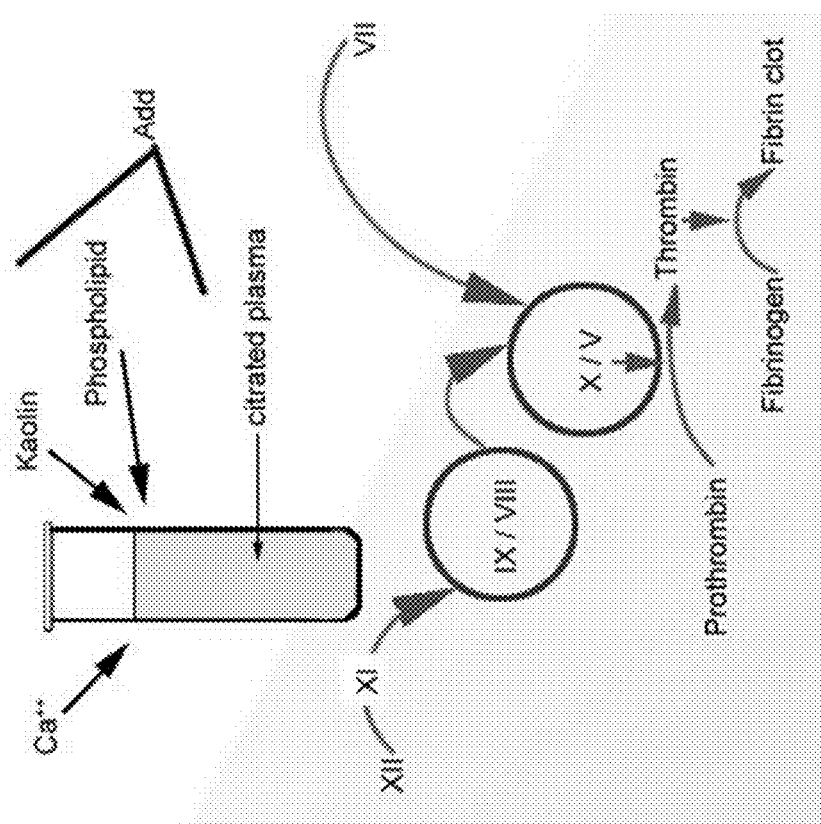
FIG. 3 shows the experimental setup and mechanism as measured by Activated Partial Thromboplastin Time (aPTT) Assay.

The aPTT assay is performed as described previously with modifications. Detailed methods for the aPTT assay may be found in the PDR Staff. Physicians' Desk Reference. 2004, which is herein incorporated by reference. Briefly, 50 μL of thawed human plasma (normal or hemophilic) is added to test tubes. 5 μl of saline (e.g. Sigma) or 5 μl of test agent (e.g., NASP) dissolved in saline is mixed with 50 μl of plasma. aPTT reagent (e.g. STA APTT, Roche) is reconstituted in 5 ml distilled water and 50 μL of the reconstituted solution containing the APTT reagent is added to each test tube and incubated for 2-3 minutes at 37° C. Afterwards 50 μL of 25 mM $CaCl_2$ is added to initiate clotting. All pipetting steps and plasma clotting time measurements are carried out with an ACL Elite Pro (Beckman Coulter) instrument. The experimental setup and mechanism of aPTT assay as presented herein is shown in FIG. 3.

Dilute Prothrombin Time (dPT) Assay

One dPT assay for use herein is a modified standard clinical PT assay. Details methods for the dPT assay can be found in Nordfang et al. (1991) Thromb Haemost 66:464-467; Welsch et al. (1991) Thrombosis Research 64: 213-222, which is herein incorporated by reference. A dilute prothrombin time assay with added tissue factor pathway inhibitor (TFPI-dPT) is used to demonstrate the TFPI-inhibiting effect of fucoidan BAX513 in hemophilic patient plasma (George King Biomedical). Plasma samples are pre-incubated with 0.3 μg/mL full-length TFPI (aa 1-276, constitutively produced by SKHep1) and BAX513 (0.03-1 μg/mL) for 15 mM at RT. TF reagent TriniClot PT Excel S (Trinity Biotech), diluted in Hepes-buffered saline 1:400 with 0.5% BSA is added to the plasma samples on an ACL Pro Elite hemostasis analyzer (Instrumentation Laboratory). Clotting is initiated with 0.25 mM $CaCl_2$. The volume ratio of plasma:TF:$CaCl_2$ was 1:1:1. The time for plasma clotting is measured with a ACL ProElite Hemostasis Analyzer.

Animal Bleeding Time Assays

The bleeding time assay can be used to measure changes in hemostasis function in normal or hemophilic (FVIII or FIX or vWF deficient) rodents following administration of a test agent (e.g., vehicle control or NASP). A test agent (e.g., vehicle control or NASP) is administered to a rodent once or twice daily orally, parenterally, or by continuous infusion. For example, 0.1 ml/10 g body weight (subscapular) of a test agent at a dose ranging from 0.1 to 10 mg/kg can be administered with small gauge needles twice a day for at least one day and preferably more than 3 days. On the day bleeding time is assayed, rodents are anesthetized with ketamine/xylazine (or isoflurane). Rodents are lined up on a sterile pad with a petri dish of saline for tail immersion. EMLA creme is applied to the tail of rodents at an intended cut site. For mice, the very tip of the tail is snipped, and the tail is placed into the saline dish and a counter is started. For rats, an 8 mm long by 1 mm deep incision is made on the dorsal part of the rat tail, which is then transferred into saline. The time for cessation of visible bleeding into the saline is recorded. For rodents, bleeding times are approximately 10 minutes for normal control mice and 6 minutes for normal control rats. After completion of the bleeding time assay, the rodent's tail is dried with sterile gauze, verified for hemostasis, and the rodent is returned to the cage. Silver nitrate can be applied to the cut site if necessary.

Alternatively, bleeding times can be measured in mice (Broze et al. (2001) Thromb. Haemost. 85:747-748) or in dogs (Scallan et al. (2003) Blood 102:2031-2037; Pijnappels et al. (1986) Thromb. Haemost. 55:70-73) by other methods. Alternative or additional pharmacodynamic endpoints may include sampling of blood from NASP-treated subjects for direct analysis or for plasma isolation, and measurement of ex vivo clotting times (e.g., Whole Blood Clotting Time and/or PT and/or APTT) or coagulation factor levels.

Whole Blood Clotting Time (WBCT) Assay

The WBCT assay is performed as follows. Mice are briefly anesthetized in an isoflurane chamber. The mice are then bled (e.g. 150 µl) from the retro orbital plexus into plastic blood collection tubes. The tubes are placed in a 37° C. water bath and a stop watch is used to measure clotting time. During this period, the tubes are inverted at 1 minute intervals. The time required for blood clotting (full/not partial clot) is measured.

Example 2

Extraction and Purification of a Fucoidan Crude Composition

Methods for extracting and isolating fucoidans from edible seaweeds, brown algae and echinoderms (e.g., sea urchins, sea cucumbers) have been described in detail in co-pending U.S. patent application Ser. No. 12/449,712, filed Feb. 25, 2010, the disclosure of which is herein incorporated by reference. Examples of NASPs and fucoidans of interest are listed in Table 1, below.

Crude fucoidan *Laminaria japonica* fucoidan extract (SIGMA) was purified as follows in order to reduce levels of heavy metals and proteins. Water was added to the crude fucoidan material at 40°-45° C. EDTA was then added to remove heavy metals and the pH was adjusted to 6.0. The mixture was stirred for one hour and NaCl was added, the pH was adjusted to 6.0 and the mixture stirred for 30 minutes. Absolute ethanol was added slowly over 75 minutes at 20°-25° C. and the mixture was centrifuged at room temperature to precipitate fucoidan. The supernatant was discarded and the precipitant dissolved with water at 40°-45° C. The NaCl addition, ethanol addition, centrifugation and precipitation steps were carried out two more times (three times total). The pH of the final solution in water was adjusted to 6.0±0.2 and the solution cooled to 20°-25° C. The solution was filtered through a 2 µm filter twice and once through a 0.2 µm Posidyne filter into a sterile polyethylene bag. The filtrate was assayed for total neutral sugar content, a measure of the concentration of active fucoidan. This solution may be held at 2°-8° C. for up to a week. In order to lyophilize fucoidan, the purified solution was filtered through a 0.2 µm filter into lyophilizer bags and placed in the lyophilizer. The temperature was dropped to –40° C. and after a vacuum was applied (≤200 microns), the temperature was raised and held at 10° C. for 4 hours, 20° C. for 20 hours, 25° C. for 24 hours, and 40° C. for 24 hours. After the vacuum was released, the bags containing the lyophilized material were transferred to a tared 30-gallon drum lined with a doubled polyethylene bag and sealed with a lid and locking ring. The container was transferred to a weighing room where the lyophilization bags were cut open and the contents emptied into the double-bag-lined drum. After the drum was weighed, the drum bags were sealed, desiccant was placed around the bags, and the drum was resealed.

In the final packaging step, the lyophilized drug substance was transferred from the drum to doubled polyethylene bags containing 1-500 grams per bag. The bags were closed and packaged with desiccant into containers fixed with tamper-evident seals. The sealed containers were stored at 2-8° C.

TABLE 1

List of Compounds

1. Fucoidan 5307002, *Fucus vesiculosus*, max. MW peak 126.7 kD
2. Fucoidan VG49, *Fucus vesiculosus*, hydrolyzed sample of 5307002 of lower MW, max. MW peak 22.5 kD
3. Fucoidan VG50, *Ascophyllum nodosum*, max. MW peak 149.7 kD
4. Fucoidan VG56, *Undaria pinnatifida*, low charge (low sulphation)

TABLE 1-continued

List of Compounds

5. Fucoidan VG57, *Undaria pinnatifida*, high charge (high sulphation, deacetylated)Fucoidan GFS (5508005), *Undaria pinnatifida*, depyrogenated
6. Fucoidan GFS (L/UPF-1008), *Undaria pinnatifida*, hydrolyzed depyrogenated, max. MW peak 54 kD
7. Fucoidan GFS + Ca (L/UPF-1108), *Undaria pinnatifida*, hydrolyzed depyrogenated, max. MW peak 32 kD
8. Fucoidan GFS (L/FVF-01091), *Fucus vesiculosus*, depyrogenated, max. MW peak 125 kD
9. Fucoidan GFS (L/FVF-01092), *Fucus vesiculosus*, depyrogenated, max. MW peak 260 kD
10. Fucoidan GFS (L/FVF-01093), *Fucus vesiculosus*, hydrolyzed depyrogenated, max. MW peak 36 kD
11. Maritech ® *Ecklonia radiata* extract
12. Maritech ® *Ecklonia maxima* extract
13. Maritech ® *Alaria esculenta* extract
14. Maritech ® *Macrocystis pyrifera* extract
15. Maritech ® *Sargassum fusifome* extract
16. Maritech ® *Cladosiphon* sp extract
17. Maritech ® *Durivellea potatorum* extract
18. Maritech ® *Laminaria digitata* extract
19. Maritech ® *Fucus* polyphenol complex extract
20. Maritech ® *Ascophyllum nodosum* extract
21. Maritech ® Immune trial Fucoidan Blend
22. Maritech ® Capsules
23. Depyrogenated *Ecklonia radiata*
24. Depyrogenated *Alaria esculenta*
25. Depyrogenated *Cladosiphon* sp
26. Depyrogenated *Sargassum fusiformis*
27. Depyrogenated *Ecklonia maxima*
28. Depyrogenated *Macrocystis pyrifera*
29. *Fucus evanescens*
30. *Fucus distichus*
31. *Phyllospora comosa*
32. *Harmosira banksii*
33. *Lessonia nigescencs*

Example 3

Procoagulant Mechanism of Fucoidans

The following experiments were performed and demonstrate a previously unknown procoagulant mechanism of fucoidan. The procoagulant activity of several fucoidans was characterized by calibrated automated thrombography in tissue factor (TF)-dependent experiments and by using coagulation factor-deficient plasmas. Spiking experiments with purified coagulation factors or inhibitory antibodies verified the mechanism identified. Fucoidan-improved thrombin generation (TG) was TF-dependent. Stimulatory activity was most pronounced without TF. Improvement of TG in FXII-deficient plasma excluded the contact system as a target for the procoagulant activity. TG experiments without TF using plasmas deficient in proteins of all three coagulation pathways identified FXI as the most upstream factor responsible for fucoidan-mediated TG. Spiking FXI (30 nM) to FXI-deficient plasma restored fucoidan-mediated TG but adding FXI inhibitory antibodies to normal plasma abrogated TG, verifying FXI as a target for fucoidan. Fucoidan-dependent TG did not improve when FXIa (60 pM) was added to FXI-deficient plasma, suggesting FXI activation by fucoidan.

The relevance of this mechanism in hemophilia plasma was studied by addition of low levels of FVIII (0.2-10%) resulting in a FVIII concentration-dependent increase in fucoidan-mediated TG.

As explained above, in vitro characterization of fucoidans suggests that inhibiting TFPI and accelerating thrombin-dependent FVa formation improves hemostasis in animal models. These studies describe another procoagulant activity of fucoidans. In particular, FXI activation at low TF concentrations is a possible mechanism for fucoidan. Identification of this new mechanism contributes to the understanding of the procoagulant activities of fucoidans and assists in developing safe and efficient alternatives for treating bleeding disorders.

Example 4

Characterization of Fucoidans

Fucoidans are complex in structure with a high degree of polydispersity and heterogeneity and vary depending on the biological source. A broad range of analytical tools are applied to understand in depth the biological activities and structural properties of six different fucoidan preparations.

The following experiments were performed and demonstrate that coagulation properties of NASPs are a function of saccharide content and degree of sulfation. PPS and fucoidans purified from several brown algae (molecular weight 6-1000 kD) were studied.

Calibrated Automated Thrombography (CAT) Assay

The procoagulant activity was characterized by calibrated automated thrombography (CAT) in FVIII- and FIX-deficient and FVIII-inhibited plasma and in combination with hemophilia therapeutics. The mechanism of thrombin formation as presented herein is shown in FIG. 1.

In the CAT studies, the procoagulant activity of sulfated polysaccharides was examined in several plasmas from patients with congenital coagulation factor deficiencies and FVIII-inhibited normal plasma, in order to study the procoagulant window. Pooled normal plasma or plasmas from patients with congenital coagulation factor deficiencies were obtained from George King, Bio-Medical Inc. Kansas USA. According to the supplier, the residual coagulation factor activity for each of the coagulation factor deficient plasmas was lower than 1%. As a model for antibody mediated FVIII deficiency fresh frozen pooled normal plasma (George King, Bio-Medical Inc., Kansas, USA) was incubated with high titer heat inactivated anti-human FVIII plasma raised in goat (4490 BU/ml; Baxter BioScience, Vienna, Austria) giving rise to 50 BU/mL. In some experiments, tissue factor pathway inhibitor (TFPI) activity was blocked in presence or absence of the fucoidan by either a polyclonal goat anti-human TFPI antibodies (R&D Systems, AF2974, Minneapolis, US) or a monoclonal anti-TFPI antibody directed against the positively charged C-terminus of TFPI (Sanquin White Label Products, MW1848, clone CLB/TFPI C-terminus, Amsterdam, The Netherlands) at plasma concentration of 25 nM or 100 nM, respectively. If not indicated otherwise, the plasmas were mixed with corn trypsin inhibitor (CTI) (Hematologic Technologies, Inc., Essex Junction, Vt., USA), providing a final concentration of 40 µg/mL, for specific inhibition of factor XIIa.

Test samples were prepared by dissolving quantities of NASPs of interest in Hepes buffered saline and adding human serum albumin (Sigma-Aldrich Corporation, St. Louis, Mo., USA) to a concentration of 5 mg/mL. Reference samples were prepared from reference proteins FVIII Immunate® reference standard (Baxter BioScience, Vienna, Austria); Factor eight inhibitor by-passing activity (FEIBA) reference standard (Baxter BioScience, Vienna, Austria); NovoSeven® recombinant activated FVII (Novo Nordisk A/S, Denmark) and purified human plasma FIX (Enzyme Research Laboratories, South Bend, Ill., USA). A thrombin calibrator compound was obtained from Thrombinoscope BV, Maastricht, The Netherlands.

In particular, the influence of each NASP of interest on thrombin generation was measured in duplicate via calibrated automated thrombography in a Fluoroskan Ascent® reader (Thermo Labsystems, Helsinki, Finland; filters 390 nm excitation and 460 nm emission) following the slow cleavage of the fluorogenic substrate Z-Gly-Gly-Arg-AMC (Hemker H C., *Pathophysiol Haemost Thromb* (2003) 33:4-15). To each well of a 96 well micro-plate (Immulon 2HB, clear U-bottom; Thermo Electron), 80 µL of pre-warmed (37° C.) plasma was added. For triggering thrombin generation by tissue factor, 10 µL of PPP reagent containing an amount of recombinant human tissue factor (rTF) and phospholipid vesicles composed of phosphatidylserine, phosphatidylcholine and phosphatidylethanolamine (48 µM) (Thrombinoscope BV, Maastricht, The Netherlands) was added. For studying the procoagulant activity of NASPs, a final TF concentration of 1 pM was used to provide FVIII and TFPI sensitivity of the test system. Alternatively, a mix of rTF (Innovin®, Siemens Healthcare Diagnostics Inc., Tarrytown, N.Y., USA) and a phospholipid emulsion composed of phosphatidylcholine, phosphatidylserine and sphingomyelin (Phospholipid-TGT, Rossix, Mölndal, Sweden) was used, which allowed to adjust the TF concentrations from 0 to 20 pM. Just prior to putting the plate into the pre-warmed (37° C.) reader, 10 µL of test or reference sample or calibrator compound was added. Thrombin generation was started by dispensing 20 µL of FluCa reagent (Thrombinoscope BV, Maastricht, The Netherlands) containing fluorogenic substrate and Hepes buffered $CaCl_2$ (100 mM) into each well and fluorescence intensity was recorded at 37° C.

The parameters of the resulting thrombin generation curves were calculated using the Thrombinoscope™ software (Thrombinoscope BV, Maastricht, The Netherlands) and thrombin calibrator to correct for inner filter and substrate consumption effects. With the thrombin calibrator as a reference, the molar concentration of thrombin in the test wells was calculated by the software. The thrombin amounts at the peak of each thrombin generation curve (peak thrombin, nM) were plotted against the peak thrombin obtained from standard concentrations of a reference protein (FVIII Immunate® reference standard, FEIBA reference standard) and fitted by a non-linear algorithm. Based on this calibration, FVIII Immunate®, FEIBA and FIX equivalent activities were calculated. Other parameters recorded were lag time (time interval between starting measurement and start of thrombin generation), peak time (time interval between starting measurement and peak thrombin) and endogenous thrombin potential (area under curve of thrombin concentration versus time).

By CAT, the procoagulant window of sulfated polysaccharides in hemophilic plasma spanned more than two orders of magnitude with maximum effects being equivalent to (mU/mL) 730-940 FVIII, 32-80 FIX and 590-1230 FEIBA. As such, NASPs of interest combined with FVIII, FEIBA, FIX or FVIIa had an additive procoagulant effect.

Figure 2:
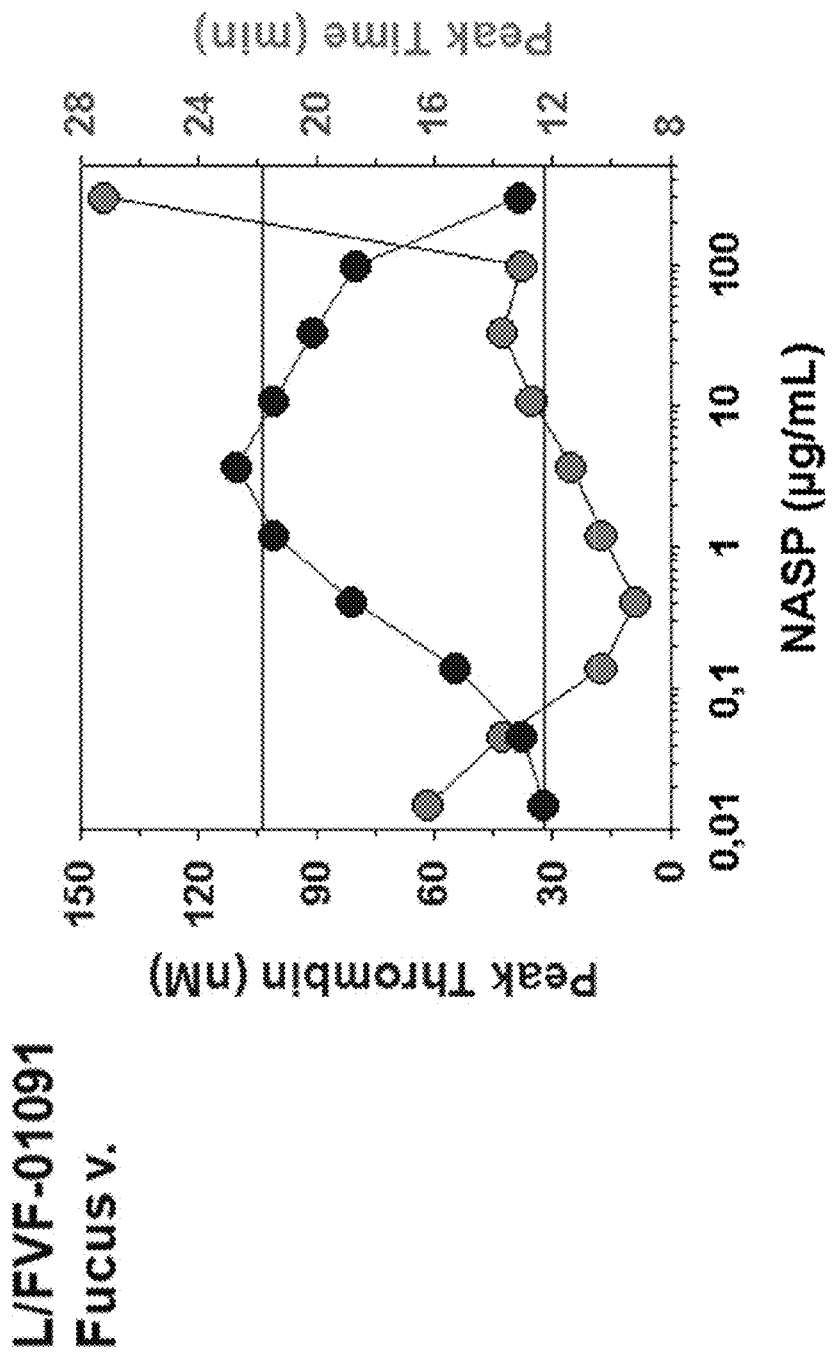
FIG. 2 show an example of data acquired for the procoagulant activity of fucoidan *Fucus vesiculosus* L/FVF-1091 as measured using calibrated automated thrombography (CAT) in FVIII-inhibited plasma.

An example of data acquired by calibrated automated thrombagraphy assay is illustrated in FIG. 2. Results from CAT assays as well as a comparison with hemophilia therapeutics by CAT are summarized in Tables 2-4, below. As demonstrated in these results, some NASPs of interest increase thrombin generation in the absence of CTI at higher concentrations.

TABLE 2

CAT Evaluation of Compounds (1)

| NASP | Pro-coagulant window (μg/mL) | Optimal Conc (μg/mL) | FEIBA Equi activity (mU/mL) |
|---|---|---|---|
| 5307002 | 0.1-150* | 1.9 | 399 (54-186) |
| VG49 | 0.2-150* | 5.6 | 369 (70-134) |
| VG50 | 0.1-150* | 1.9 | 352 (20-99) |
| VG56 | 16.7-150* | 150 | 162 (58-162) |
| VG57 | 0.1-50 | 1.9 | 357 (41-297) |
| 5508005 | 0.05-100 | 3.7 | 460 (35-182) |
| L/UPF-1008 | 0.14-100 | 3.7 | 290 (33-242) |
| L/UPF-1108 | 0.14-100 | 3.7 | 296 (36-214) |
| L/FVF-01091 | 0.05-100 | 3.7 | 601 (29-298) |
| L/FVF-01092 | 0.14-100 | 11.1 | 476 (56-336) |
| L/FVF-01093 | 0.14-300 | 11.1 | 441 (32-143) |
| Maritech® Ecklonia radiata extract | 0.05-100 | 11.1 | 657 (51-354) |
| Maritech® Ecklonia maxima extract | 0.14-100 | 11.1 | 896 (78-629) |
| Maritech® Alaria esculenta extract | 0.14-300* | 11.1 | 375 (55-155) |
| Maritech® Macrocystis pyrifera extract | 0.05-100 | 1.2 | 551 (29-58) |
| Maritech® Sargassum fusifome extract | 0.41-300 | 33.3 | 474 (58-440) |
| Maritech® Clados sp. extract | 3.7-300* | 300* | 173 (21-173) |
| Maritech® Durivellea potatorum extract | 0.41-300 | 33.3 | 569 (65-400) |
| Maritech® Laminaria digitata extract | 0.05-33.3 | 3.7 | 676 (62-253) |
| Maritech® Fucus polyphenol complex extract | 0.41-300* | 11.1 | 538 (87-248) |
| Maritech® Ascophyllum nodosum extract | 0.41-300* | 33.3 | 675 (51-119) |
| Maritech® Immune trial Fucodian Blend | 0.05-100 | 3.7 | 551 (25-391) |
| Maritech® Capsules 100 | 0.41-300* | 11.1 | 491 (84-372) |
| Maritech® Capsules 200 | 0.14-300* | 3.7 | 534 (40-429) |
| Depyrogenated Ecklonia radiata | 0.05-33.3 | 3.7 | 465 (49-480) |
| Depyrogenated Alaria esculenta | 0.14-100 | 3.7 | 391 (96-291) |
| Depyrogenated Cladosiphon sp. | — | — | — |
| Depyrogenated Sargassum fusiformis | 0.14-300* | 33.3 | 416 (22-236) |
| Depyrogenated Ecklonia maxima | 0.14-100 | 11.1 | 674 (62-482) |
| Depyrogenated Macrocystis pyrifera | 0.05-33.3 | 33.3 | 707 (61-707) |
| Fucus evanescens | 0.14-100 | 3.7 | 523 (70-346) |
| Fucus distichus | 0.14-300* | 3.7 | 422 (49-23) |
| Phyllospora comosa | 0.41-300* | 11.1 | 294 (62-145) |
| Hamosira banksii | 0.14-300* | 33.3 | 585 (39-308) |
| Lessonia nigescencs | 0.41-300* | 100 | 429 (43-157) |

TABLE 3

CAT Evaluation of Compounds (2)

| NASP | Procoagulant window (μg/mL) | Optimal Conc. (μg/mL) | Thrombin Peak (%) | $EC_{50}$ (μg/mL) |
|---|---|---|---|---|
| BAX513 | 0.05-100 | 1.23 | 113.0 | 0.25 |
| F.v. 5307002 | 0.41-100 | 1.23 | 143.5 | 0.36 |
| F.v. 5308004 | 0.41-100 | 1.23 | 135.5 | 0.46 |
| F.v. 5308005 | 0.41-100 | 1.23 | 138.6 | 0.40 |
| F.v. VG201094A | 0.41-300 | 11.10 | 79.8 | 1.64 |
| F.v. VG201094B | 0.41-300 | 3.70 | 77.7 | 1.42 |
| F.v. VG201095 | 0.41-300 | 3.70 | 89.8 | 0.95 |
| F.v. VG201097 | 1.23-300 | 11.10 | 85.2 | 2.50 |
| F.v. L/FVF1091 | 0.05-100 | 1.23 | 128.8 | 0.16 |
| F.v. VG201096A | 0.14-100 | 1.23 | 111.1 | 0.29 |
| F.v. VG201096B | 0.14-100 | 1.23 | 110.8 | 0.23 |
| F.v. DS100110A | 0.14-100 | 1.23 | 113.8 | 0.26 |
| F.v. L/FVF1092 | 0.05-300 | 1.23 | 121.0 | 0.50 |
| F.v. VG201098A | 0.05-300 | 1.23 | 131.9 | 0.54 |
| F.v. VG201098B | 0.14-300 | 1.23 | 121.8 | 0.47 |
| F.v. L/FVF1093 | 0.14-300 | 3.70 | 116.1 | 0.82 |
| F.v. DS100111C | 0.14-300 | 3.70 | 147.0 | 0.52 |
| U.p. 5508005 | 0.14-100 | 1.23 | 107.2 | 0.36 |
| U.p. 5508004 | 0.14-100 | 1.23 | 111.5 | 0.22 |
| U.p. DPGFS03 | 0.14-100 | 1.23 | 101.2 | 0.27 |
| U.p. UPF200911032 | 0.41-100 | 3.7 | 104.9 | 1.24 |
| E.m. DS100109C | 0.05-100 | 3.7 | 211.8 | 1.36 |
| E.m. dep DS100112A | 0.05-100 | 3.7 | 183.7 | 0.82 |
| M.p. MPF12008002 | 0.14-100 | 1.23 | 103.4 | 0.29 |
| M.p. dep VG201099A | 0.14-100 | 1.23 | 104.7 | 0.27 |
| M.p. dep VG201099B | 0.14-100 | 1.23 | 112.0 | 0.40 |

TABLE 4

CAT Evaluation of Compounds (3)

| NASP | Advate Equiv. at opt. concentration (mU/mL) | FEIBA Equiv. at opt. concentration (mU/mL) |
|---|---|---|
| F.v. 5307002 | 1430 | 456 |
| F.v. L/FVF 1091 | 1540 | 458 |
| F.v. L/FVF 1092 | 1080 | 520 |
| F.v. L/FVF 1093 | 670 | 324 |
| U.p. 5508005 | 1260 | 445 |
| E.m. DS100112A | >2000 | 833 |
| Normal Plasma | 880 | 322 |

Activated Partial Thromboplastin Time (aPTT) Assay

The anti-coagulant activity was characterized Activated Partial Thromboplastin Time (aPTT) Assay. The aPTT assay is performed as described above. Briefly, 50 μL of thawed human plasma (normal or hemophilic) is added to test tubes. 5 μl of saline (e.g. Sigma) or 5 μl of test agent (e.g., NASP) dissolved in saline is mixed with 50 μl of plasma. aPTT reagent (e.g. STA APTT, Roche) is reconstituted in 5 ml distilled water and 50 μL of the reconstituted solution containing the APTT reagent is added to each test tube and incubated for 2-3 minutes at 37° C. Afterwards 50 μL of 25 mM $CaCl_2$ is added to initiate clotting. All pipetting steps and plasma clotting time measurements are carried out with an ACL Elite Pro (Beckman Coulter) instrument. The experimental setup and mechanism of aPTT assay as presented herein is shown in FIG. 3.

Figure 4:
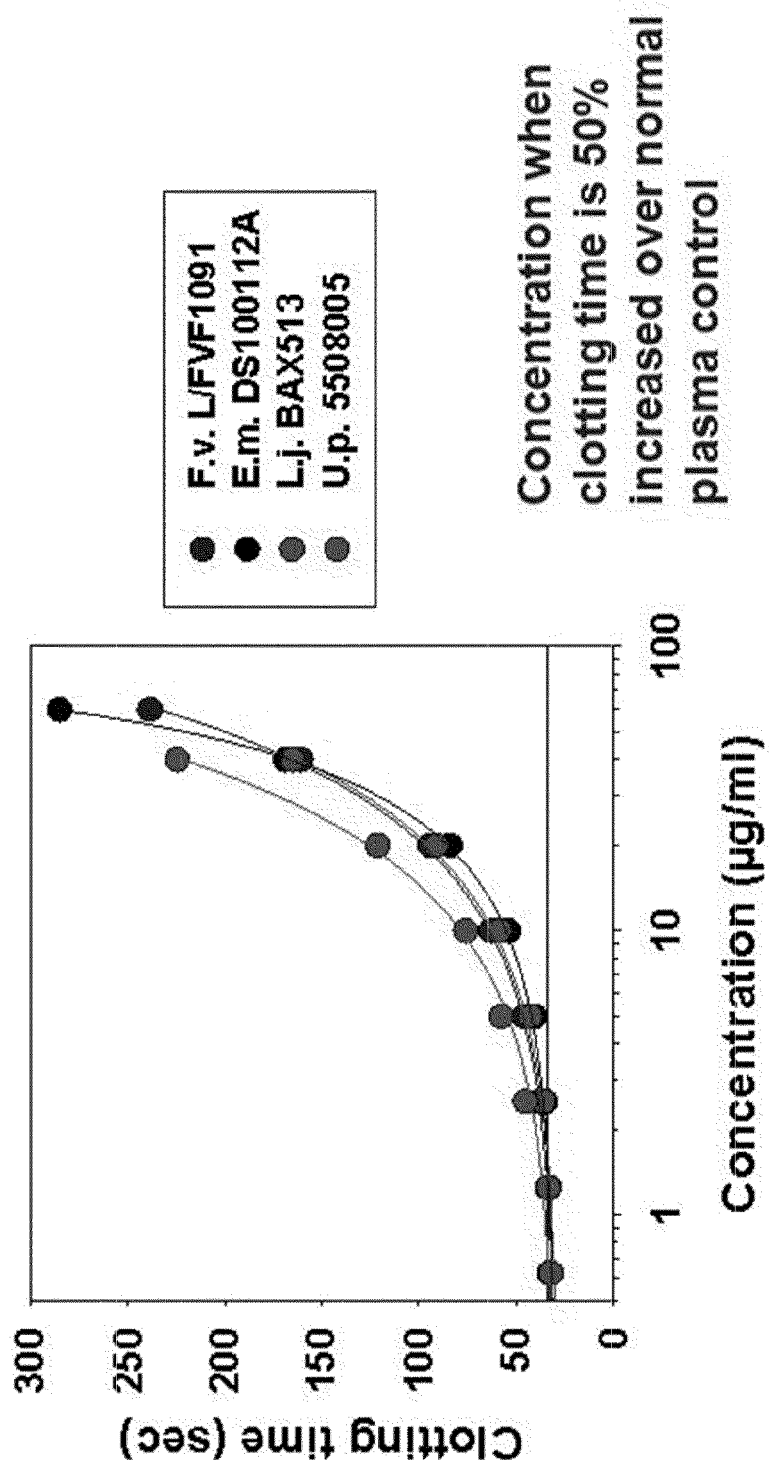
FIG. 4 show an example of data acquired for the pro- and anti-coagulant activity as measured using the Activated Partial Thromboplastin Time (aPTT) Assay.

An example of data acquired by activated partial thromboplastin time assay is illustrated in FIG. 4. Results from aPTT assays as well as the evaluation of pro- and anti-coagulant activity as compared with results obtained by CAT are summarized in Table 5, below.

TABLE 5 aPTT Assay: Pro- and Anti-coagulant Activity Evaluation

| NASP | 50% Increase Clotting Time (μg/mL) aPTT | $EC_{50}$ (μg/mL) CAT | Ratio aPTT/CAT |
|---|---|---|---|
| BAX513 | 7.0 | 0.3 | 23.3 |
| F.v. 5307002 | 7.0 | 0.4 | 17.5 |
| F.v. 5308004 | 6.0 | 0.5 | 12.0 |
| F.v. 5308005 | 6.5 | 0.4 | 16.3 |
| U.p. 5508005 | 4.5 | 0.4 | 11.3 |

TABLE 5-continued aPTT Assay: Pro- and Anti-coagulant Activity Evaluation

| NASP | 50% Increase Clotting Time (µg/mL) aPTT | EC$_{50}$ (µg/mL) CAT | Ratio aPTT/CAT |
|---|---|---|---|
| U.p. 5508004 | 2.3 | 0.2 | 11.5 |
| U.p. DPGFS03 | 3.6 | 0.3 | 12.0 |
| U.p. UPF200911032 | 6.55 | 1.24 | 5.3 |
| E.m. DS100109C | 9.8 | 1.36 | 7.2 |
| E.m. DS100112A | 8.7 | 0.8 | 10.9 |
| E.m. DS100155A | 4.3 | 1.1 | 3.9 |
| E.m. DS100155B | 5.5 | 1.0 | 5.5 |
| E.m. DS100155C | 5.0 | 0.9 | 5.6 |
| F.v. L/FVF1091 | 6.5 | 0.2 | 32.5 |
| F.v. L/FVF1092 | 9.9 | 0.5 | 19.8 |
| F.v. VG201094A | 25.21 | 1.64 | 15.4 |
| F.v. VG201094B | 23.36 | 1.42 | 16.5 |
| F.v. VG201095 | 19.41 | 0.95 | 20.4 |
| F.v. VG201096A | 6.3 | 0.3 | 21.0 |
| F.v. VG201096B | 6.2 | 0.2 | 31.0 |
| F.v. VG201097 | 30.09 | 2.50 | 12.0 |
| F.v. VG201098A | 14.8 | 0.5 | 29.6 |
| F.v. VG201098B | 16.2 | 0.5 | 32.4 |
| F.v. VG2010100A | 5.0 | 0.6 | 8.3 |
| F.v. VG2010100B | 5.0 | 0.6 | 8.3 |
| F.v. VG2010100C | 5.3 | 0.8 | 6.6 |
| F.v. L/FVF1093 | 11.9 | 0.8 | 14.9 |
| F.v. DS100161A | 7.7 | 0.5 | 15.4 |
| F.v. DS100161B | 7.8 | 0.5 | 15.6 |
| F.v. DS100161C | 8.4 | n/d | n/a |
| F.v. DS100161D | 8.2 | n/d | n/a |
| F.v. DS100161E | 6.9 | n/d | n/a |
| F.v. DS100110A | 6.1 | 0.26 | 23.5 |
| F.v. DS100111C | 8.9 | 0.5 | 17.8 |
| F.v. DS100159A | 6.6 | 0.5 | 13.2 |
| F.v. DS100159B | 6.5 | 0.4 | 16.3 |
| F.v. DS100160A | 6.7 | 0.4 | 16.8 |
| M.p. MPF12008002 | 6.34 | 0.29 | 21.9 |
| M.p. dep VG201099A | 5.66 | 0.27 | 21.0 |
| M.p. dep VG201099B | 4.97 | 0.4 | 12.4 |

CAT Assay and aPTT Assay—Activity of Low Molecular Weight Fucoidans

Low molecular weight fucoidans were obtained by fractionation using size exclusion chromotagraphy as described in detail in Example 5, below. Size exclusion chromotagraphy was used to obtain fucoidans (*Fucus vesiculosus*) having a molecular weight which ranged from less than 1 to 30 kilodaltons. Fractions obtained from size exclusion chromotagraphy had molecular weight ranges of: a) less than 1 kilodalton; b) 1 to 30 kilodaltons; c) less than 30 kilodaltons; d) 10 to 30 kilodaltons; e) 1 to 10 kilodaltons and f) 5 to 30 kilodaltons. Each fraction was studied by CAT assay and aPTT assay, the method as described in detail above, and compared to the corresponding unfractionated fucoidan sample. Results for the pro- and anticoagulant activity is shown in Table 6, below.

As can be seen from the results, low molecular weight fucoidans possess similar activities as compared to unfractionated fucoidan and are at least as effective in enhancing coagulation.

TABLE 6

Activity of Low Molecular Weight Fucoidans

| Lot # | MW Range Defined by filter cutoff (kD) | MW by SEC-MALLS (kD) | 50% Increase aPTT µg/mL | EC$_{50}$ CAT µg/mL | Ratio aPTT/CAT |
|---|---|---|---|---|---|
| DS1001104A | >1 kD | 156 | 5.6 | 0.21 | 26.7 |
| DS1001104D | 1-30 kD | 51 | >60 | 2.92 | >20.6 |
| DS1001106A | <30 kD | 91 | 6.4 | 0.20 | 32.0 |
| DS1001106B | 10-30 kD | 28 | 10.1 | 0.30 | 33.7 |
| DS1001106C | 1-10 kD | 6.7 | 43.9 | 2.46 | 17.8 |
| DS1001108B | 5-30 kD | 18 | 15.1 | 0.45 | 33.6 |
| F.v. VG201096 B | Ø 110 kD | 110 | 6.2 | 0.17 | 36.5 |

CAT Assay and aPTT Assay—Activity and SEC Chromatography of F.v. L/FVF-1091

Size exclusion chromatography was used to fractionate a sample of F.v. L/FVF-1091 fucoidan. Five fractions were collected and structural characteristics were studied by NMR, ion-exchange chromotagraphy and elemental analysis, the methods described in greater detail in Example 5, below. Structural characteristics for the fractions are shown in Table 7, below.

TABLE 7

Structural Characteristics of Fractions from SEC chromatography of F.v. L/FVF-1091

| Fraction # | MW (kDa) | Sulfur (wt %) | Sulfate (wt %) |
|---|---|---|---|
| S1 | 436.1 | 9.3 | 30.0 |
| S2 | 135.0 | 10.3 | 33.2 |
| S3 | 54.1 | 10.0 | 32.2 |
| S4 | 30.2 | 11.1 | 35.6 |
| S5 | 10.6 | 9.9 | 31.7 |

Each fraction was studied by CAT assay and aPTT assay, the method as described in detail above, and compared to the corresponding unfractionated fucoidan sample. Results for the pro- and anticoagulant activity is shown in Table 8, below.

As can be seen from the results, low molecular weight fractions possess better activities as compared to unfractionated fucoidan and are at least as effective in for enhancing coagulation.

TABLE 8

Activity of Fractions from from SEC chromatography of F.v. L/FVF-1091

| Fraction # | 50% Increase Clotting Time (aPTT) µg/mL | EC$_{50}$ (CAT) µg/mL | Ratio aPTT/CAT |
|---|---|---|---|
| Starting Material | 3.6 | 0.47 | 8 |
| S1 | 6.1 | 0.29 | 21 |
| S2 | 6.1 | 0.3 | 20 |
| S3 | 7.4 | 0.35 | 21 |
| S4 | 15.7 | 0.78 | 20 |
| S5 | 7.2 | 0.21 | 34 |

Thromboelastography Rotation Thromboelastometry (TEG-ROTEM) Assay

For the TEG studies, blood samples from a healthy individual were drawn into citrated Venoject® tubes (Terumo Europe, Leuven, Belgium (127 mmol/L)) mixing one part of citrate with nine parts of blood by a 21-G butterfly needle. The first tube aspirated was discarded. A proportion of these blood samples were incubated with high titer heat inactivated anti-human FVIII antiserum raised in goat (3876 BU/ml; Baxter BioScience, Vienna, Austria) resulting in 51 or 150 BU/mL. Test samples were prepared by dissolving quantities of sulfated polysaccharide in Hepes buffered saline and adding human serum albumin (Sigma-Aldrich Corporation, St. Louis, Mo., USA) to a concentration of 5 mg/mL. A control sample was prepared in which no sulfated polysaccharide was included.

Continuous visco-elastic assessment of human whole blood clot formation and firmness was performed by rotation thromboelastography with whole blood preparations in the presence or absence of sulfated polysaccharides. Briefly, blood was added into a disposable cuvette in a heated cuvette holder. A disposable pin (sensor) was fixed on the tip of a rotating axis. The axis was guided by a high precision ball bearing system and rotates back and forth. The axis was connected with a spring for the measurement of elasticity. The exact position of the axis was detected by the reflection of light on a small mirror on the axis. The loss of elasticity when the sample clots lead to a change in the rotation of the axis. The data obtained were analyzed on a computer and visualized in a thromboelastogram. The thromboelastogram shows elasticity (mm) versus time (s). An elasticity of close to zero was observed before clot formation begins. Mirror image traces above and below the zero line indicated the effect of clot formation on the rotation of the axis.

Recordings were made using a ROTEM thromboelastography coagulation analyzer (Pentapharm, Munich, Germany) at 37° C. Before starting each experiment, the citrated whole blood was mixed with corn trypsin inhibitor (CTI) (Hematologic Technologies, Inc., Essex Junction, Vt., USA) providing a final concentrations of 37 to 62 µg/mL for specific inhibition of FXIIa, in order to inhibit FXIIa-mediated contact activation. The analytical set-up was as follows: To 20 µL of test sample or control, 300 µL of pre-warmed (37° C.) CTI treated citrated whole blood was added, followed by 20 µL of a 1:15 dilution of TF PRP reagent containing recombinant human tissue factor (rTF, 3 pM) (TS40, Thrombinoscope BV, Maastricht, The Netherlands). Coagulation was initiated by the addition of 20 µL 200 mM CaCl$_2$ (star-TEM®, Pentapharm, Munich, Germany) and recordings were allowed to proceed for at least 120 min. The final concentration of rTF in the assay was 11 or 44 fM.

The thromboelastographic parameters of clotting time (CT), clot formation time (CFT) and maximum clot firmness (MCF) were recorded in accordance with the manufacturer's instructions. CT is defined as the time from the start of measurement to the start of clot formation. CFT is defined as the time from the start of clot formation until an amplitude of 20 mm is reached. MCF is the maximum difference in amplitude between the two traces during the assay. The first derivative of the data of the thromboelastogram were plotted to obtain a graph of velocity (mm/s) against time (s). From this graph, the maximum velocity (maxV) was determined. The time at which the maximum velocity was obtained (maxV-t) was also determined.

Figure 5:
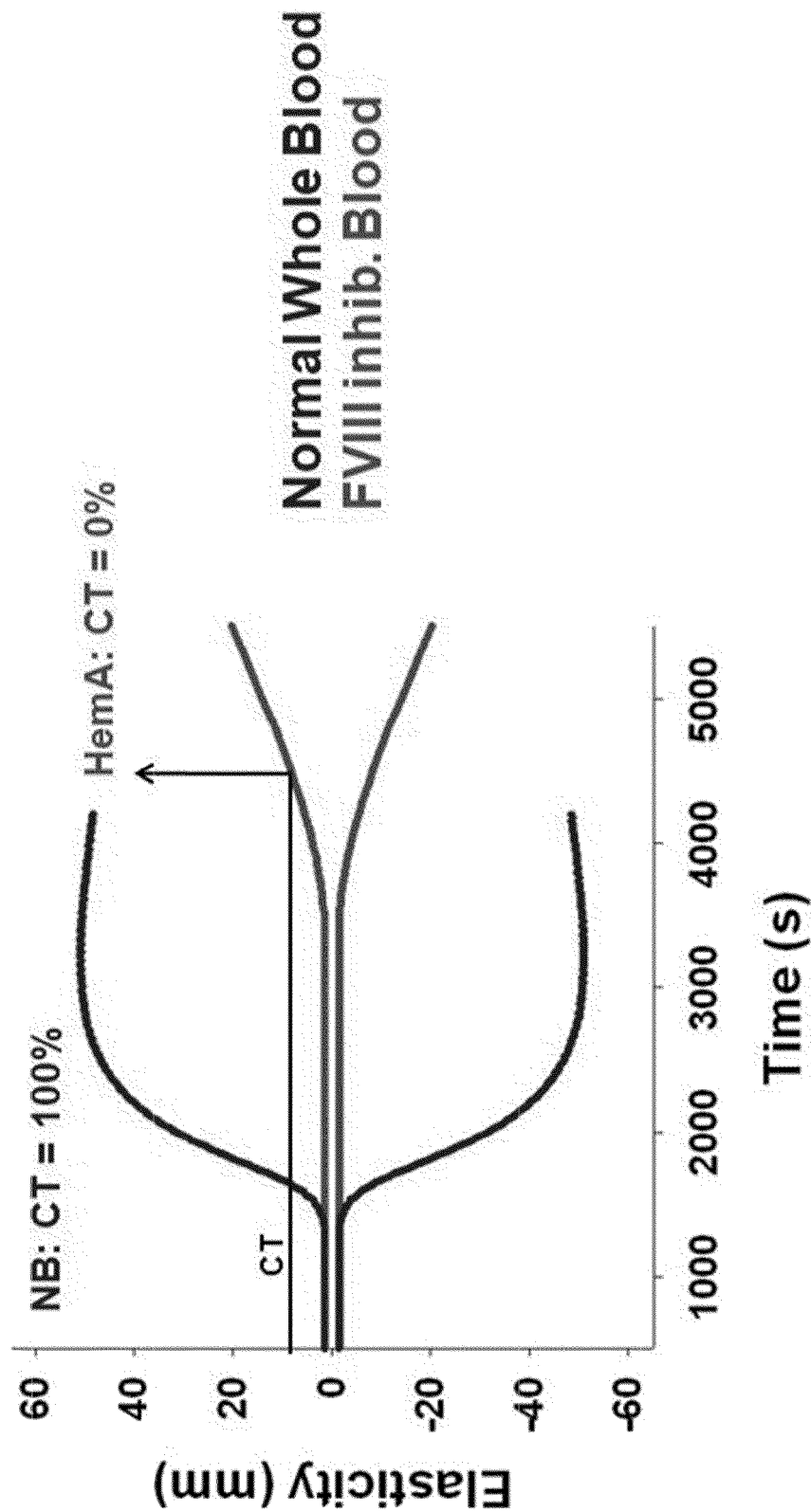
FIG. 5 shows an example of data acquisition in determining clotting time, clot formation time and mean clot formation as measured using Rotation Thromboelastometry.

As explained above, the effect of various NASPs on thromboelastographic parameters was tested in FVIII-inhibited blood at two and four concentrations, respectively. Two controls were performed in which no fucoidan was present. One used FVIII-inhibited blood and the other used normal blood. An example of data results from an ROTEM thromboelastography coagulation analyzer is shown in FIG. 5.

Results from data obtained from a first ROTEM thromboelastography coagulation analyzer are summarized in Table 9. The FVIII-inhibited blood had a characteristically long clotting time and clot formation time. The clotting time and clot formation time were both shorter in the FVIII-inhibited blood containing fucoidan, with the fucoidan exerting a concentration dependent effect on both parameters. Fucoidan also reduced CT and CFT in normal blood.

Figure 6:
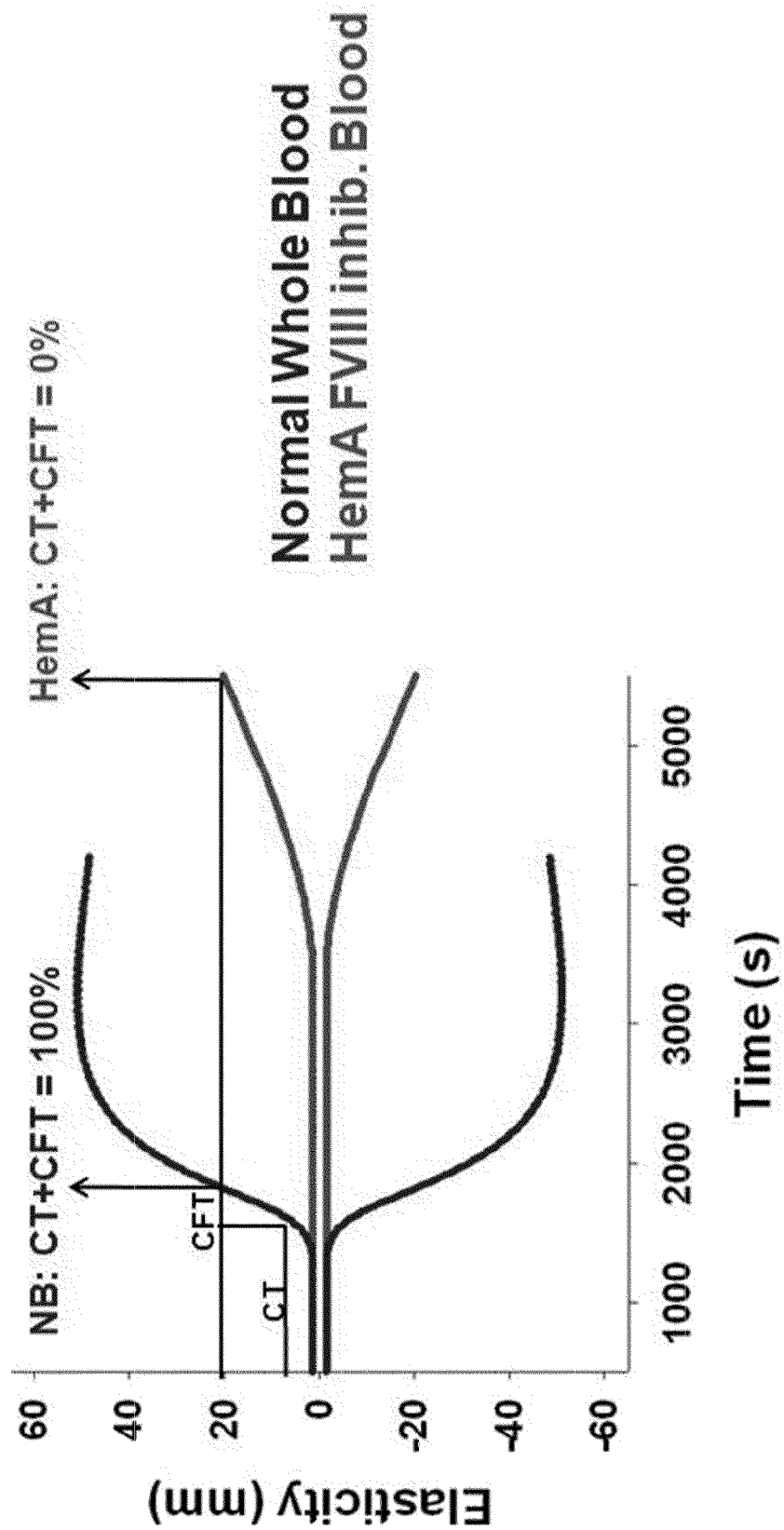
FIG. 6 shows a second example of data acquisition in determining clotting time, clot formation time and mean clot formation as measured using Rotation Thromboelastometry.

Data from a second set of experiments using ROTEM thromboelastography coagulation analyzer such as those illustrated in FIG. 6 are summarized in Table 10. As demonstrated by the data presented in Table 10, Fucoidan Smart City and fucoidan derived from *Laminaria japonica* enhances coagulation parameters of FVIII inhibited blood and normal blood.

TABLE 9

Thromboelastography Rotation Thromboelastometry (TEG- ROTEM) Assay (1)

| Fucoidan/Type of Blood | CT (s) | CFT (s) | MCF (mm) | Activity (%) |
|---|---|---|---|---|
| Control - FVIII-inhibited blood | 2447 | 881 | 55 | — |
| *Undaria pinnatifida* 10 nM - FVIII inhibited blood | 1163 | 419 | 55 | — |
| *Undaria pinnatifida* 100 nM - FVIII inhibited blood | 956 | 330 | 50 | — |
| Control - Normal blood | 869 | 274 | 45 | — |
| *Undaria pinnatifida* 10 nM - Normal blood | 767 | 225 | 46 | — |
| *Undaria pinnatifida* 100 nM - Normal blood | 382 | 105 | 54 | — |
| Control - FVIII-inhibited blood | 4829 | 2054 | — | 0 |
| *Laminaria japonica* 0.4 µg/mL - FVIII inhibited blood | 2917 | 1431 | — | 68 |
| *Laminaria japonica* 1.2 µg/mL - FVIII inhibited blood | 2069 | 798 | 63 | 98 |
| *Laminaria japonica* 3.7 µg/mL - FVIII inhibited blood | 1656 | 525 | 63.5 | 113 |
| *Laminaria japonica* 11.1 µg/mL - FVIII inhibited blood | 1650 | 421 | 60 | 113 |
| Control - Normal blood | 1557 | 373 | 52 | 100 |
| *Laminaria japonica* 0.4 µg/mL - Normal blood | 1458 | 271 | 55 | — |
| *Laminaria japonica* 1.2 µg/mL - Normal blood | 1121 | 244 | 54 | — |
| *Laminaria japonica* 3.7 µg/mL - Normal blood | 651 | 224 | 52 | — |
| *Laminaria japonica* 11.1 µg/mL - Normal blood | 744 | 317 | 52 | — |
| Control - FVIII-inhibited blood | 3474 | 1978 | — | 0 |
| *F. vesiculosus* L/FVF1091 0.4 µg/mL - FVIII inhibited blood | 1970 | 1074 | 58 | 72 |
| *F. vesiculosus* L/FVF1091 1.2 µg/mL - FVIII inhibited blood | 1417 | 606 | 61 | 99 |
| *F. vesiculosus* L/FVF1091 3.7 µg/mL - FVIII inhibited blood | 1299 | 421 | 60.5 | 104 |
| *F. vesiculosus* L/FVF1091 11.1 µg/mL - FVIII inhibited blood | 1450 | 418 | 60.5 | 97 |
| Control - Normal blood | 1390 | 313 | 50.5 | 100 |
| Control - FVIII-inhibited blood | 3789 | 2073 | — | 0 |
| *F. vesiculosus* 5307002 0.4 µg/mL - FVIII inhibited blood | 2284 | 1302 | — | 79 |
| *F. vesiculosus* 5307002 1.2 µg/mL - FVIII inhibited blood | 1729 | 811 | 61.5 | 109 |
| *F. vesiculosus* 5307002 3.7 µg/mL - FVIII inhibited blood | 1364 | 484 | 62 | 128 |
| *F. vesiculosus* 5307002 11.1 µg/mL - FVIII inhibited blood | 1530 | 357 | 60 | 119 |
| Control - Normal blood | 1892 | 388 | 50 | 100 |
| Control - FVIII-inhibited blood | 4150 | 1820 | — | 0 |
| *F. vesiculosus* L/FVF1092 0.4 µg/mL - FVIII inhibited blood | 2363 | 1125 | — | 72 |
| *F. vesiculosus* L/FVF1092 1.2 µg/mL - FVIII inhibited blood | 1587 | 662 | 61.5 | 103 |
| *F. vesiculosus* L/FVF1092 3.7 µg/mL - FVIII inhibited blood | 1428 | 464 | 62 | 109 |

TABLE 9-continued

Thromboelastography Rotation Thromboelastometry (TEG- ROTEM) Assay (1)

| Fucoidan/Type of Blood | Clotting parameters | | | |
|---|---|---|---|---|
| | CT (s) | CFT (s) | MCF (mm) | Activity (%) |
| F. vesiculosus L/FVF1092 11.1 µg/mL - FVIII inhibited blood | 1184 | 240 | 60 | 119 |
| Control - Normal blood | 1659 | 358 | 51 | 100 |
| Control - FVIII-inhibited blood | 3262 | 2103 | — | 0 |
| F. vesiculosus L/FVF1093 0.4 µg/mL - FVIII inhibited blood | 2362 | 1054 | — | 51 |
| F. vesiculosus L/FVF1093 1.2 µg/mL - FVIII inhibited blood | 1970 | 1015 | — | 74 |
| F. vesiculosus L/FVF1093 3.7 µg/mL - FVIII inhibited blood | 1669 | 828 | 60 | 91 |
| F. vesiculosus L/FVF1093 11.1 µg/mL - FVIII inhibited blood | 1316 | 459 | 60 | 111 |
| Control - Normal blood | 1510 | 291 | 53 | 100 |
| Control - FVIII-inhibited blood | 4339 | — | — | 0 |
| Undaria pinnatifida 5508005 0.4 µg/mL - FVIII inhibited blood | 2891 | 1362 | — | 52 |
| Undaria pinnatifida 5508005 1.2 µg/mL - FVIII inhibited blood | 1534 | 524 | 62.5 | 101 |
| Undaria pinnatifida 5508005 3.7 µg/mL - FVIII inhibited blood | 1215 | 284 | 62 | 113 |
| Undaria pinnatifida 5508005 11.1 µg/mL - FVIII inhibited blood | 1197 | 272 | 57 | 114 |
| Control - Normal blood | 1574 | 343 | 52 | 100 |
| Control - FVIII-inhibited blood | 3943 | — | — | 0 |
| Ecklonia maxima DS100112A 0.4 µg/mL - FVIII inhibited blood | 2334 | 1192 | — | 80 |
| Ecklonia maxima DS100112A 1.2 µg/mL - FVIII inhibited blood | 1285 | 338 | 66 | 132 |
| Ecklonia maxima DS100112A 3.7 µg/mL - FVIII inhibited blood | 833 | 141 | 63 | 154 |
| Ecklonia maxima DS100112A 11.1 µg/mL - FVIII inhibited blood | 919 | 160 | 59 | 150 |
| Control - Normal blood | 1926 | 398 | 56.5 | 100 |

TABLE 10

Thromboelastography Rotation Thromboelastometry (TEG- ROTEM) Assay (2)

| Fucoidan/Type of Blood | Clotting parameters | | |
|---|---|---|---|
| | CT (s) | CFT (s) | MCF (mm) |
| Fucoidan Smart City in Normal Blood | | | |
| Hem A Blood | 5033 | 2025 | — |
| Smart City 2 µg/ml | 3061 | 1102 | — |
| Smart City 10 µg/ml | 2074 | 1039 | 57 |
| Human Blood | 931 | 255 | 52 |
| Fucoidan Smart City in FVIII Inhibited Blood | | | |
| Hem A Blood | 4594 | 2894 | 27 |
| Smart City 2 µg/ml | 2493 | 888 | 55 |
| Smart City 10 µg/ml | 1651 | 613 | 51 |
| Human Blood | 1104 | 283 | 45 |
| Fucoidan Laminaria japonica in FVIII Inhibited Blood | | | |
| FVIII i. blood | 3367 | 2275 | — |
| HemA + Laminaria japonica | 2313 | 1018 | 53 |
| Normal Blood | 1374 | 346 | 43 |
| NB + Laminaria japonica | 939 | 432 | 46 |

Example 5

Structural Characterization of Fucoidan

Fucoidan preparations were characterized based on various structural characteristics.

Degree of Sulfation

The degree of sulfation was determined by elemental analysis using a PE 2400 CHN Analyzer and sulfur content was determined by colorimetric a titration. Sulfur content was also verified using inductively coupled plasma mass spectrometry. The results of analysis are summarized in Table 11.

TABLE 11

Degree of Sulfation

| NASP | Sulfur (Colorimetric) w % | Sulfate - $SO_3$ (Derived) w % |
|---|---|---|
| L. japonica BAX513 | 5.8 | 14.5 |
| E.m. DS100112A | 6.0 | 15.0 |
| E.m. DS100155A | 6.7 | 21.6 |
| E.m. DS100155B | 6.7 | 21.6 |
| E.m. DS100155C | 6.1 | 19.6 |
| E.m. VG23 | 6.6 | 16.5 |
| U.p. 5508005 | 10.0 | 25.0 |
| U.p. 5508004 | 10.0 | 25.0 |
| U.p. DPGFS03 | 10.0 | 25.0 |
| U.p. VG56 | 5.3 | 16.0 |
| U.p. VG57 | 10.6 | 32.1 |
| F.v. 5307002 | 8.7 | 21.8 |
| F.v. 5308004 | 9.5 | 23.4 |
| F.v. 5308005 | 8.4 | 21.0 |
| F.v. L/FVF 1091 | 8.7 | 21.8 |
| F.v. L/FVF1092 | 7.7 | 19.3 |
| F.v. L/FVF1093 | 6.6 | 16.5 |
| F.v. VG49 | 8.6 | 26 |
| F.v. VG50 | 8.6 | 26 |
| F.v. VG2010100A | 8.6 | 27.7 |
| F.v. VG2010100B | 9.1 | 29.2 |
| F.v. VG2010100C | 9.6 | 31.0 |
| F.v. VG201096A | 9.1 | 22.8 |
| F.v. VG201096B | 9.9 | 24.8 |
| F.v. VG201098A | 5.7 | 14.3 |
| F.v. VG201098B | 5.2 | 13.0 |
| F.v. DS100111C | 6.7 | 16.8 |
| F.v. DS100159A | 6.8 | 21.9 |
| F.v. DS100159B | 7.3 | 23.4 |
| F.v. DS100160A | 7.2 | 23.2 |

Monosaccharide Content

The monosaccharide content of various NASPs was analyzed by ion chromatography and by nuclear magnetic resonance spectroscopy.

Ion Chromatography

Figure 7:
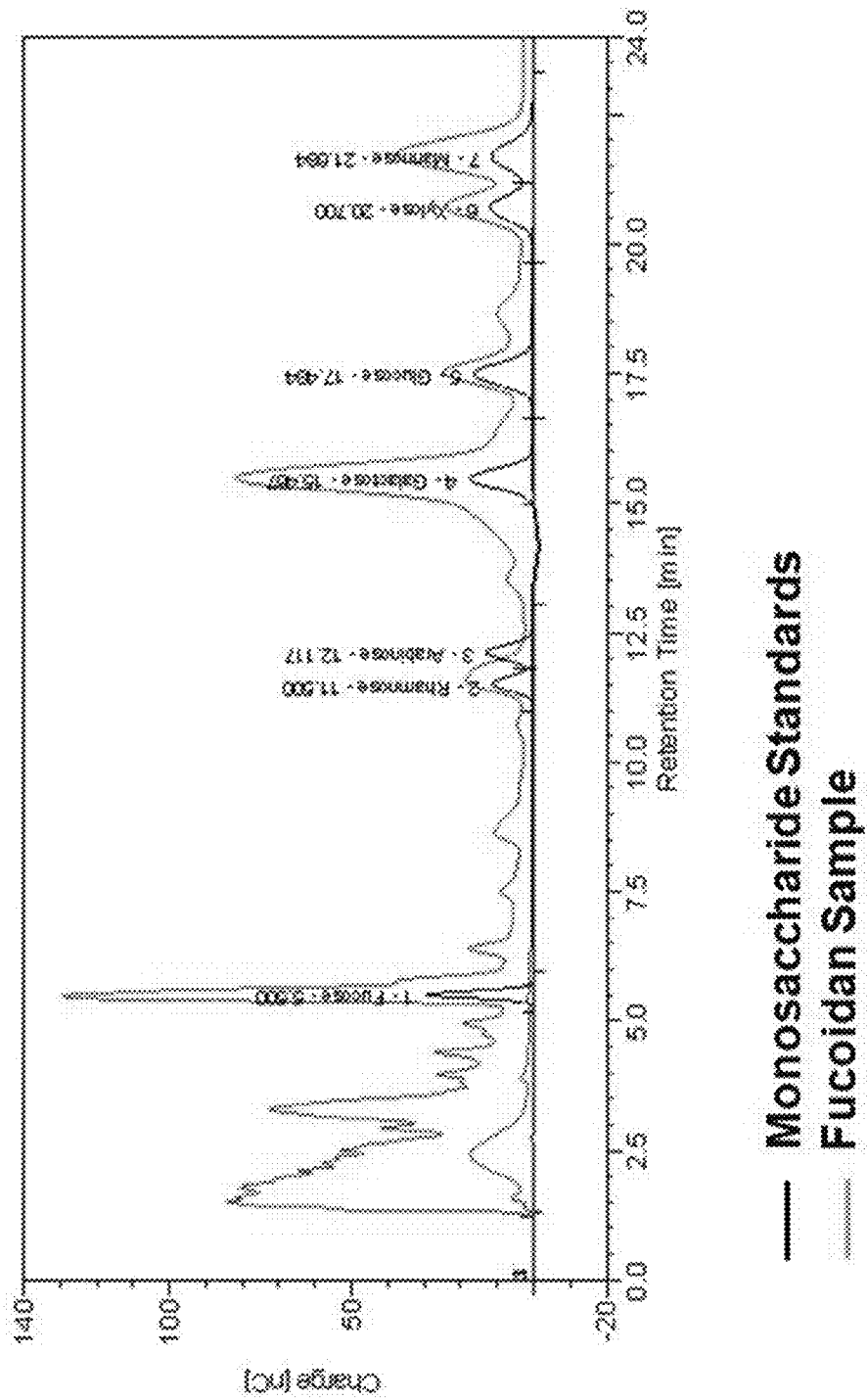
FIG. 7 shows an Ion Chromatogram (IC) for determining monosaccharide composition of a fucoidan sample.
Figure 8:
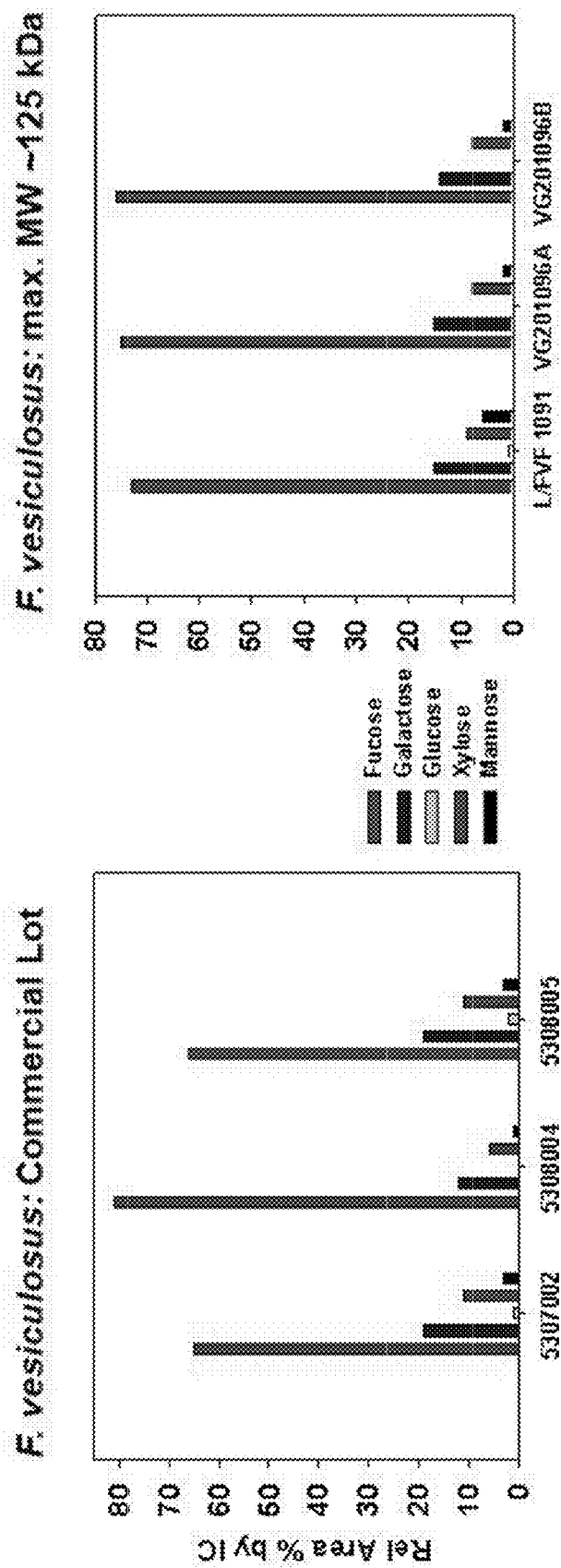
FIG. 8 shows monosaccharide composition for several NASPs as measured by Ion Chromatography.
Figure 9:
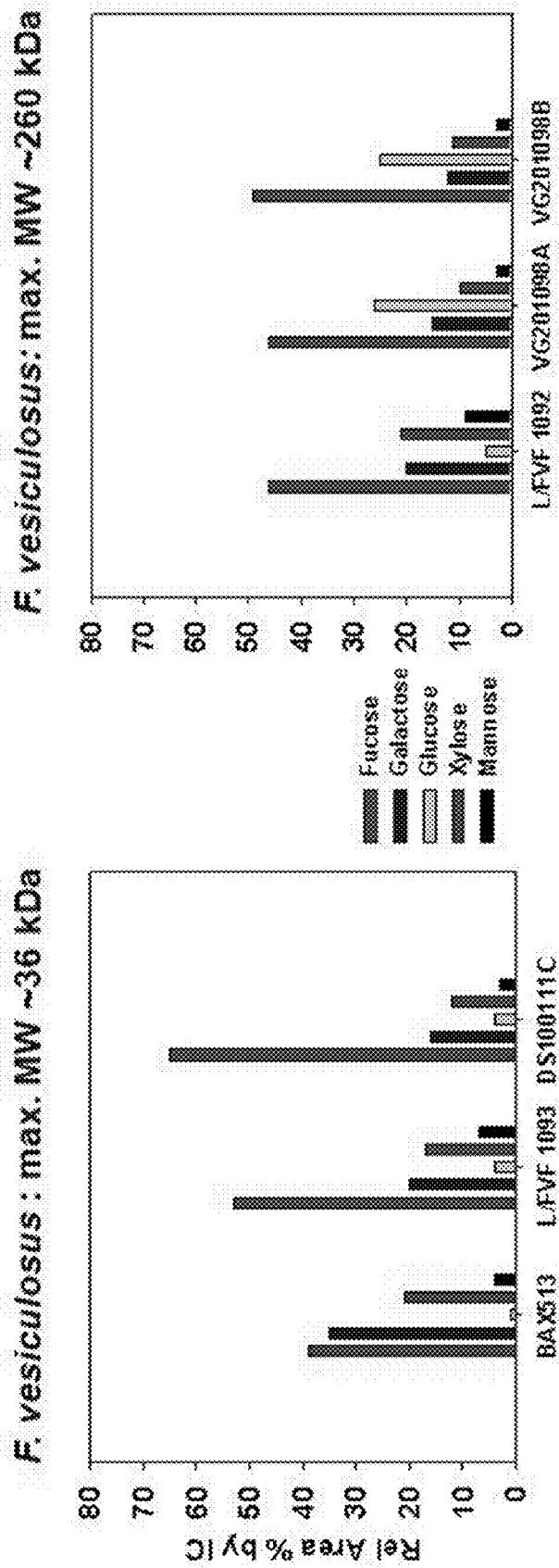
FIG. 9 shows monosaccharide composition for several NASPs as measured by Ion Chromatography.
Figure 10:
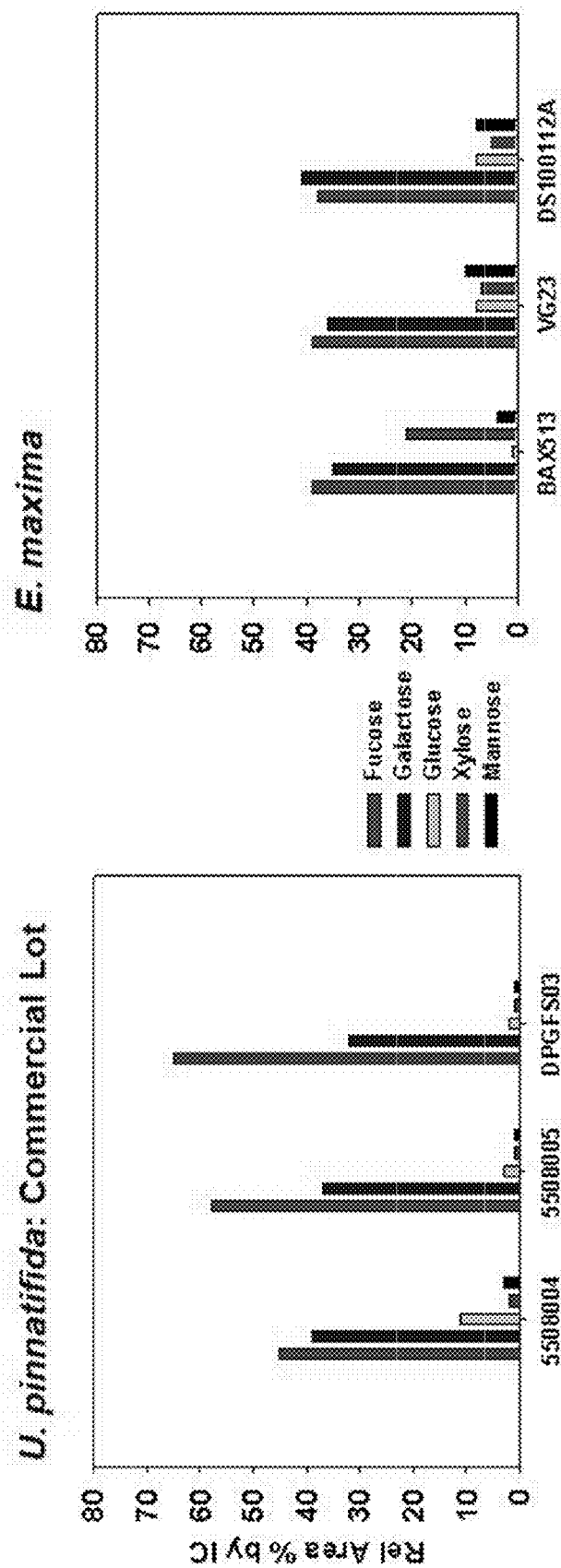
FIG. 10 shows monosaccharide composition for several NASPs as measured by Ion Chromatography.

Monosaccharide compositions of various NASPs were analyzed using ion chromatography. A Dionex ICS 3000 system was used to analyze the hydrolysates coupled with a PAD detector. Seven neutral sugars were applied in this method as standards. They were Fucose, Rhamnose, Arabinose, Galactose, Glucose, Xylose and Mannose. An example of a chromatogram to determine monosaccharide composition is illustrated in FIG. 7. Monosaccharide contents as determined by ion-exchange chromatagraphy of several NASPs of interest are depicted in FIGS. 8-10 and summarized in Table 12, below.

IC condition:

| Column: | Dionex guard column CarboPac ® PA10, 2 × 50 mm, and Dionex analytical column CarboPac ® PA1, 4 × 250 mm. |
|---|---|
| Mobile phase: | 2 mM NaOH |
| Flow rate: | 1 mL/min |
| Column Temp.: | 35° C. |
| Running time: | 30 min |

TABLE 12

Fucose Content by Ion-exchange Chromatography

| NASP | % Fucose |
|---|---|
| L. japonica BAX513 | 39 |
| F.v. 5307002 | 65 |
| F.v. L/FVF 1091 | 73 |
| F.v. L/FVF1092 | 46 |
| F.v. L/FVF1093 | 53 |
| U.p. 5308005 | 58 |
| E.m. DS100112A | 38 |

Nuclear Magnetic Resonance Spectroscopy

A Bruker Avance III NMR spectrometer with a dual $^1H/^{13}C$-Cryoprobe was used to analyze the fucoidan starting material and its fractions. Each sample was dissolved in ~0.6 mL $D_2O$. Qualitative NMR experiments were used to characterize their structures. One-dimensional $^1H$ NMR spectra were obtained using 16 scans, a 90° pulse, a relaxation delay of 20 seconds, 32K Data points, and a 2 second acquisition time. The phase sensitive multiplicity edited Heteronuclear Single Quantum Correlation (HSQC), magnitude mode Heteronuclear Multiple Bond Correlation (HMBC) and correlation spectroscopy (COSY) spectra were obtained using 1024 data points in the observe domain and 128 points in the second dimension. Quantitative one-dimensional $^{13}C$ NMR spectra were obtained using 3 k scans, a relaxation delay of 5 seconds. Based on the $^{13}C$ NMR spectra of fucoidan starting material and its fractions, their alginate and fucose contents could be calculated. Based on the degree of complexity of the anomeric and fingerprint ranges in $^{13}C$-NMR, their heterogeneity order could be roughly ranked on a scale from 1-7, 1 being the highest and 7 being the lowest. For example, a ranking of 1 indicates a high heterogeneity sample whereas a 7 indicates a low heterogeneity sample.

Alginate Content (C $\%^{alginate}$ is the % alginate of the total saccharides, and can be calculated from the fact that:
Carbonyl groups are only present in alginate, where there is one per saccharide.
Each sugar residue, from alginate or fucoidan, has one anomeric carbon per saccharide ring.
Therefore:

$$C\ \%^{alginate} = \frac{\int carbonyls}{\int anomerics} \times 100\% \qquad \text{Eq. [1]}$$

where ∫carbonyls=integral of carbonyl groups; ∫anomerics=integral of anomeric region.

The alginate content was calculated and listed in Table 2. Because the value for F.V. VG preparations was so low, they were listed as having less than 10% alginate.

Fucose Content (C $\%^{fucose}$) is the % fucose of the neutral saccharides (total saccharides-alginate), and is based on the fact that there is one methyl group per fucose residue:

$$C\ \%^{fucose} = \frac{\int methyls}{\int anomerics - \int carbonyls} \times 100\% \qquad \text{Eq. [2]}$$

where ∫methyls=integral of methyl groups.

Equation 2 was used for E.M. DS and F.V. DS preparations where the alginate content is substantial. The F.V. VG samples had negligible alginate content, and equation 2 was simplified to:

$$C\ \%^{fucose} = \frac{\int methyls}{\int anomerics} \times 100\% \qquad \text{Eq. [3]}$$

Figure 11:
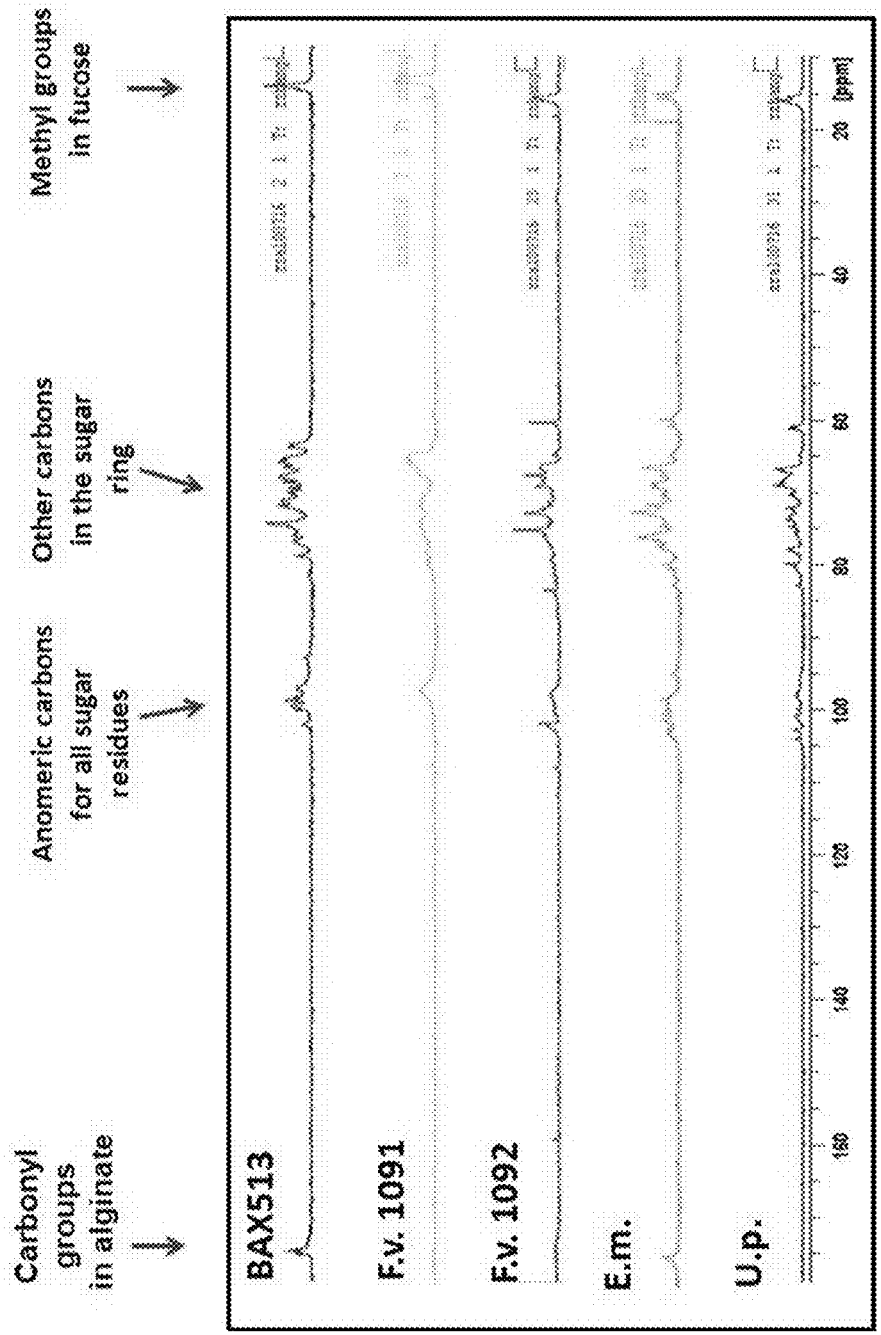
FIG. 11 shows NMR spectra for determining fucose and alginate content and heterogeneity of a fucoidan sample.

Example spectra used to determine monosaccharide composition are illustrated in FIG. 11. The monosaccharide content and heterogeneity of several NASPs of interest as determined by NMR are summarized in Table 13.

TABLE 13

Monosaccharide Content by Nuclear Magnetic Resonance Spectroscopy

| NASP | % Fucose | % Alginate | Heterogeneity Order (Scale 1-7, 1 = highest) |
|---|---|---|---|
| E.m. DS100112A | 46 | 31 | 2 |
| E.m. DS100155A | 55 | 32 | 2 |
| E.m. DS100155B | 51 | 27 | 2 |
| E.m. DS100155C | 51 | 25 | 2 |
| F.v. L/FVF 1091 | 91 | ≤10 | 7 |
| F.v. VG2010100A | 93 | ≤10 | 7 |
| F.v. VG2010100B | 89 | ≤10 | 7 |
| F.v. VG2010100C | 95 | ≤10 | 7 |
| F.v. DS100111C | 52 | Low signal | 5 |
| F.v. DS100159A | 78 | 12 | 5 |
| F.v. DS100159B | 79 | 14 | 5 |
| F.v. DS100160A | 75 | 11 | 5 |
| L. japonica BAX513 | 40 | ~24 | ~1 |
| F.v. 5307002 | 87 | ~≤10 | ~7 |
| F.v. L/FVF1092 | 52 | ~≤10 | ~6 |
| F.v. L/FVF1093 | 54 | Low signal | ~6 |
| U.p. 5508005 | 50 | ≤10 | ~3 |

* Based on degree of the complexity of anomerics and the fingerprint region in $^{13}C$-NMR. The heterogeneity order was roughly ranked from 1 to 7, where the heterogeneity of Bax513 is 1, the highest heterogeneity. Bax513 is not listed in Table 10, but is observed in FIG. 11

Molecular Weight Distribution

The molecular weight distribution of various NASPs (e.g., fucoidans) was analyzed by size exclusion chromatography, anion exchange fractionation, gel electrophoresis.

SEC Chromatography

Size exclusion chromatography (SEC) was conducted as follows. A 10 mg/mL sample solution was prepared and filtered through a 0.45 μm Ultrafree-MC HV Centrifugal Filter, followed by injection of 200 μl into HPLC. An Agilent 1100 HPLC system coupled with Wyatt Technology DAWN HELEOS, Quasi-Elastic Light Scattering (QELS), multi-angle laser light scatter (MALLS) and Optilab rEX differential refractive index (dRI) detectors and a GE Healthcare column, Superdex 200 column, were used to fractionate starting material solution by size. Based on the profile of RI detector, the NASP (e.g., fucoidan) was fractionated by different range of retention time. The molecular weights of fractions were determined by analyzing them with same method with MALLS detector.

LC Conditions:

Analytical Column: GE Healthcare Superdex 200, 10/300GL

Mobile Phase: 10% PBS Buffer, pH 7.4

Flow Rate: 1.0 mL/Minute

Column Temp. Ambient

Sample Temp. Set at 5° C.

Injection Volume: 100 μL

In one example, where two major peaks appeared in a chromatogram of a fucoidan sample, the calculation of the molecular weight of the two peaks is described below.

| Molecular weight calculation | | | | |
|---|---|---|---|---|
| | Ret. Time (min) | $V_e$ (mL) | $K_{av}$ | lg MW (kDa) | MW (Da) |
| Fraction I | 19.843 | 7.9372 | 0.015706 | 5.119959 | >200,000 |
| Fraction II | 22.121 | 8.8484 | 0.106975 | 4.961954 | 90000 |

$V_e$ = volume of eluent collected
$V_o$ = column void volume
$V_t$ = total bed volume
$K_{av} = V_e - V_o/V_t - V_o$
lg MW = Logarithm of Molecular weights Example molecular weight profiles of some NASPs (e.g., fucoidans) of interest are summarized in Table 14, below.

TABLE 14

Molecular Weight Distribution
Molecular weight profiles of some fucoidans of interest. Molecular weights are relative to dextran.

| Sample | Max peak MW (kDa) | MW % >1600k | MW %1100-1600k | MW %200-1100k | MW % 60-200k | MW %20-60k | MW %5-20k | MW % <5k |
|---|---|---|---|---|---|---|---|---|
| U.p. VG57 | — | 10.5 | 4 | 30 | 28 | 15 | 3 | 16.4 |
| U.p. VG56 | — | 10.5 | 2 | 16 | 24 | 26 | 10.5 | 12.7 |
| F.v.5307002 | 126.7 | 7 | 2 | 19 | 21 | 15 | 10 | 11.9 |
| F.v. VG49 | 22.5 | 1 | 0.5 | 5 | 14 | 30 | 28 | 12.0 |
| A.n. VG50 | 149.7 | 22 | 5 | 24 | 18 | 12 | 7.5 | 27.6 |
| U.p. L/UPF-1008 | 54 | 3.1 | 1.6 | 16.4 | 26.0 | 24.3 | 12.2 | 16.4 |
| U.p. L/UPF-1108 | 32 | 5.1 | 0.9 | 10.7 | 22.3 | 30.5 | 17.9 | 12.7 |
| F.v. L/FVF-01091 | 125 | 2.1 | 2.7 | 33.5 | 28.9 | 14.6 | 6.2 | 11.9 |
| F.v. L/FVF-01092 | 260 | 19.9 | 6.9 | 32.7 | 15.8 | 7.7 | 5.0 | 12.0 |
| F.v. L/FVF-01093 | 36 | 0.8 | 0.5 | 9.2 | 20.6 | 22.7 | 18.5 | 27.6 |

Anion Exchange Chromatography

Anion exchange chromatography was conducted using a weak anion exchange GE Healthcare LC system, ÄKTA Purifier 100 system and a DEAE Sepharose fast flow (FF) column (5×22 cm, column volume=431 mL) as follows.

Anion Exchange Chromatography by DEAE FF Column

Two hundred μL of a 10 mg/mL solution of fucoidan sample F.v. V201096B in 20 mM ammonium acetate pH 8.0 was prepared, filtered through 0.45 μm Ultrafree-MC HV centrifugal filter and injected onto DEAE FF column (5 mL). Analytes were detected by Phenol-Sulfuric Acid Assay offline. Separation was effected by a salt gradient using the system shown below.

LC conditions:
Mobile Phase: Solvent A, Milli-Q Water; Solvent B, 2 M NaCl
Flow rate: 49 mL/min
Column Temperature Room Temperature
Injection volume: 1.5 mL, 80 mg/mL
Gradient: 0% B, 1 CV; 0-100% B, 16 CV
Collection: 49 mL/tube
Detection: Phenol-sulfuric acid assay offline
Phenol-Sulfuric Acid Assay The odd-numbered tubes were tested by phenol-sulfuric acid assay. This assay was modified from an original method developed by Dubois, et al (Analytical Chemistry, 28, 1956, 350-356), the method of which is, herein incorporated by reference. To 300 μL sample, 100 μL 5% (w/v) aqueous phenol and subsequent 1 mL concentrated sulfuric acid were added. The reactions were done by incubation at 100° C. in an oven for 10 minutes. After the samples were cooled down to room temperature, they were transferred to 96 well plate (200 μL) and absorbance was measured at 490 nm. The chromatograms were generated by these phenol-sulfuric acid assay data.

Agarose Gel Analysis

Fucoidan starting material and lower molecular weight fractions were analyzed by agarose gel electrophoresis. The purities and charge properties of these highly disperse sulfated polysaccharides were analyzed using this method. A Bio-Rad Mini-Sub cell was used to cast the gel. Samples (10-20 μg of each) were applied to a 0.5% agarose gel in 0.04 M barium acetate and run for 2 h at 100 mA in 0.05 M 1,3-diaminopropane-acetate (pH 9.0). The gel was dyed in 0.2% (w/v) Alcian blue and 2% (v/v) acetic acid aqueous solution for 30 minutes and destained in Milli-Q water for overnight to clean the background.

PAGE Analysis

Fucoidan starting material and lower molecular weight fractions were also analyzed by polyacrylamide gel electrophoresis with a Bio-Rad mini-gel electrophoresis system. The molecular size properties of these highly disperse sulfated polysaccharides were analyzed using this method. Each sample (5-10 μg) was combined with one volume of 50% (w/v) sucrose, and the mixture was loaded into a stacking gel of 5% (total acrylamide) and analyzed with a 15% resolving gel. The upper chamber buffer composed of 0.2 M Tris and 1.25 M glycine at pH 8.3. The lower chamber buffer contained 0.1 M boric acid, 0.1 M Tris and 0.01 M disodium ethylene diamine tetra-acetic acid (EDTA) at pH 8.3. Resolving gel contained 13.6% acrylamide and 1.4% N,N'-methylenebisacrylamide and 15% sucrose and dissolved in lower chamber buffer. Electrophoresis was performed at 150 V for 80-90 min. The gel was dyed with Alcain blue in 2% (v/v) acetic acid.

Hydrolysis and Thin Layer Chromatography (TLC) Monitoring

All blanks (1N methanolic HCl), standard mix (2 mg/mL in 1N methanolic HCl) and samples (2 mg/mL in 1N methanolic HCl) were heated for approximately 24 hours in an 80° C. heating block. The hydrolyzed solutions were then evaporated to dryness under vacuum at 45-55° C. and reconstituted in water.

The hydrolysates were analyzed by TLC to monitor the completeness of hydrolysis. The following materials were used to perform the test:
1. HPTLC silica gel 60 from Merck, Germany
2. Developing solvent, 1-Propanol:$H_2O$=8:3 or Formic acid:1-butanol:$H_2O$=6:4:1.
3. Stain solvent, diphenylamine-aniline-phosphoric acid reagent—1 ml of 37.5% HCl, 2 ml of aniline, 10 ml of 85% $H_3PO_4$, 100 ml of ethyl acetate, and 2 g of diphenylamine The samples (~1.5 µL volumes) were separately loaded onto a TLC plate (~4×5 cm) and developed with the solvent system. The developed plate was dried by a heat plate and stained by dipping in diphenylamine-aniline-phosphoric acid reagent for 2 seconds, followed by heating in a 150° C. oven for approximately 10 minutes.

Elemental Analysis

The PE 2400 CHN Analyzer was used for C, H and N measurements. Sulfur was analyzed by colorimetric titration. These analyses were conducted by Intertek USA, Inc. QTI laboratory.

Lot-to-Lot Variability

The lot-to-lot variability of the NASPs of interest were tested using a Phenol-sulfuric acid depolymerization assay as well as a Toluidine Blue Assay.

Phenol-Sulfuric Acid and Toluidine Blue Assays

The quantitation of carbohydrates in NASPs were tested by phenol-sulfuric acid assay. As fucose is a component of fucoidan, it was used as a standard to help in quantifying the monosaccharide content of fucoidans. Phenol-sulfuric acid assay was performed on both known amounts of fucose and test samples under the sample conditions. Based on the standard curve generated with various amounts of fucose, carbohydrate content was determined.

Toluidine Blue Assays were performed by conventional means by adding an amount of toluidine blue to fractionated and unfractionated NASPs. Toluidine blue is a cationic dye that binds to sulfates, phosphates and carboxylates. Different NASPs will show different binding characteristics depending on sulfate and uronic acid content.

Based on the Phenol-Sulfuric Acid and Toluidine Blude Assays, there was low lot-to-lot variability between samples of NASPs tested, as described above.

Example 6

Bioavailability

Figure 12:
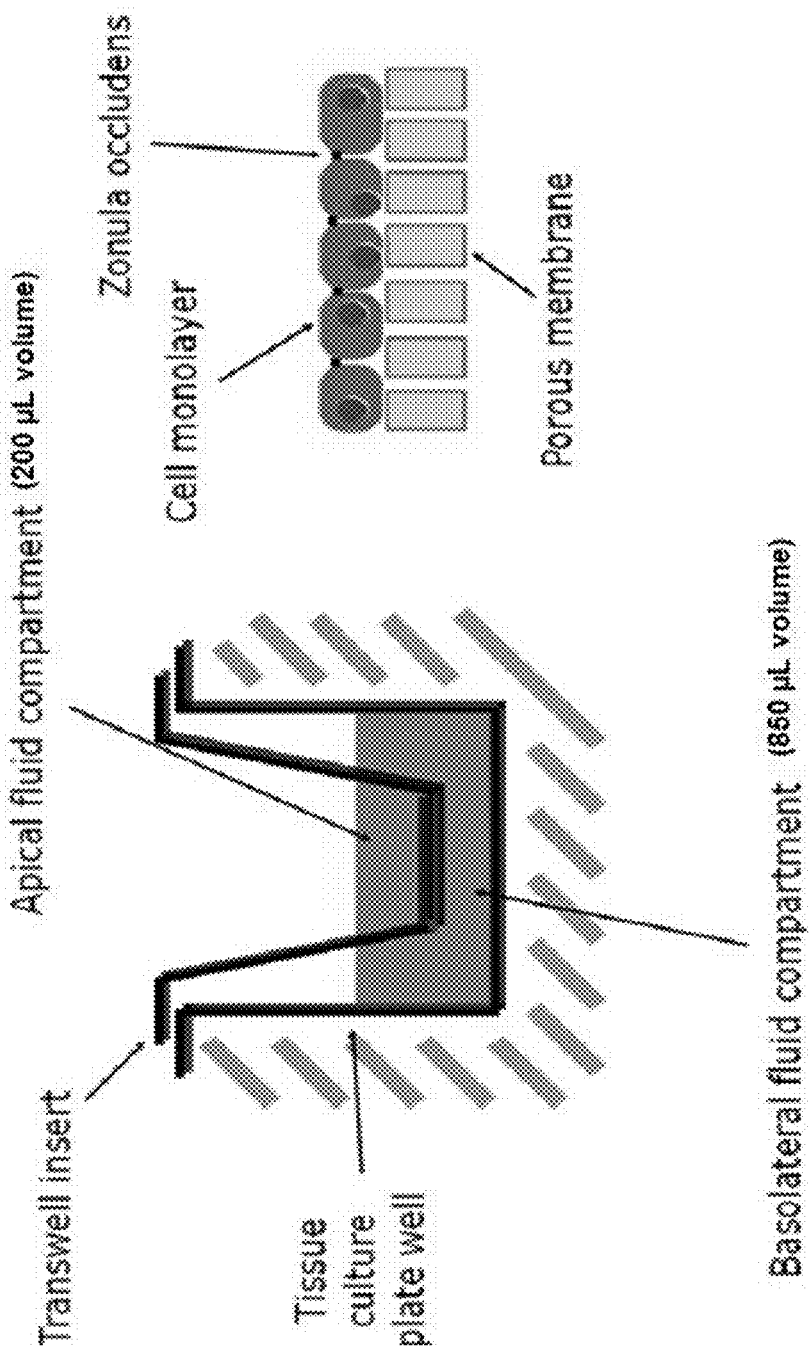
FIG. 12 shows the experimental setup for CaCo2 bioavailability screening to determine the % resorption of fucoidans.
Figure 13:
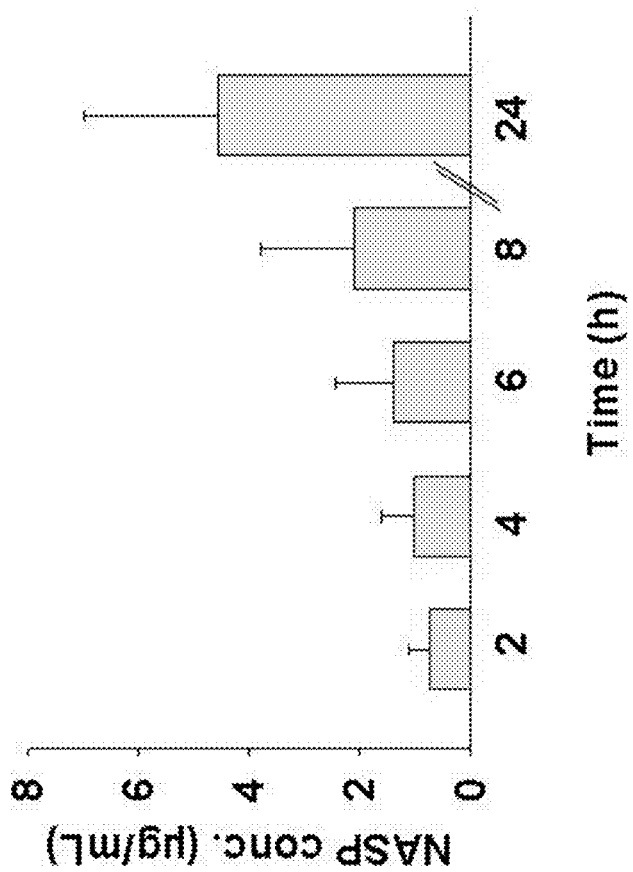
FIG. 13 shows an example of the amount of NASP resorbed in CaCo2 bioavailability screening for fucoidan *Fucus vesiculosus* L/FVF-1091.

The bioavailability of fucoidans of interest were studied using CaCo2 cell model screening. This method utilizes a human colon carcinoma cell line that expresses a wide range of transporter proteins on its cell membranes. Cell layers are grown on a membrane surface that separates two compartments (24-well plate). An example of the experimental setup for these experiments is illustrated in FIG. 12. Selected fucoidan samples were dissolved in RPMI cell medium at a concentration of 1 mg/mL and applied onto the cells in the apical compartment. Cells were incubated at 37° C. in 5% $CO_2$. Medium samples were removed from the basolateral and apical compartment at different time points. The condition of the cell layer was monitored by measurement of the transepithelial electrical resistance (TEER). Samples were analyzed by thrombin generation assay (CAT), as described above in FVIII inhibited human plasma. NASP concentration was calculated based on activity from CAT assay. All fucoidan samples were diluted in such a way that the sample concentration was in the range of increasing procoagulant activity. Based on the initial load concentration values, apical and basolateral concentrations were determined at 2 hour increments (e.g., 2 hours, 4 hours, 6 hours, 8 hours, including 24 hours). Based on the determined basolateral concentrations, the percent resorption was determined for each compound. An example of cell resorption of the fucoidan *Fucus vesiculosus*, L/FVF-1091 as a function of time as determined by the CaCo2 system is illustrated in FIG. 13. The results of bioavailability studies using the CaCo2 cell model screening of NASPs of interest as described herein are summarized below in Table 15, below.

TABLE 15

Bioavailability

| Fucoidan | % Resorption Range (2-8 hours) | % Resorption Range (24 hours) |
|---|---|---|
| F.v. L/FVF 1091 - Set 1 | 0.2-2.8 | 2.0-5.7 |
| F.v. L/FVF 1091 - Set 2 | 0-0.3 | 0-0.9 |
| F.v. L/FVF 1091 - Set 3 | 0-0.6 | 0.2-1.3 |
| F.v. VG 49 | 0.6-0.7 | 0.6-0.7 |
| F.v. L/FVF 1092 | 0.7-1.5 | 1.5-1.8 |
| F.v. 5307002 - Set 1 | 0.4-0.9 | 1.2-3.4 |
| F.v. 5307002 - Set 2 | 0-1.3 | 0.6-3.7 |
| F.v. 5307002 - Set 3 | 0.7-1.0 | 0.7-1.0 |
| U.p. 5508005 - Set 1 | 0.2-6.1 | 0.6-18.4 |
| U.p. 5508005 - Set 2 | 0.5-2.0 | 2.0-7.0 |
| U.p. 5508005 - Set 3 | 0.3-3 | 2.0-23.0 |
| U.p. 5508005 - Set 4 | 0-1.5 | 0.4-5.0 |
| F.v. L/FVF 1093 - Set 1 | 0.4-12.1 | 15.2-47.6 |
| F.v. L/FVF 1093 - Set 2 | 0.2-0.7 | 0.4-0.6 |
| F.v. L/FVF 1093 - Set 3 | 0-0.5 | 1.4-21.5 |
| E.m. DS100112A - Set 1 | 0.2-10.9 | 4.4-16.3 |
| E.m. DS100112A - Set 2 | 0-0.4 | 0.3-0.4 |
| E.m. DS100112A - Set 3 | 0 | 28.4-63.5 |
| L. japonica BAX513 - Set 1 | 0.5-1.7 | 2.0-4.7 |
| L. japonica BAX513 - Set 2 | 0.4-3.9 | 7.0-10.3 |
| L. japonica BAX513 - Set 3 | 0.2-0.6 | 0.5-2.6 |
| L. japonica BAX513 - Set 4 | 0-0.3 | 0-0.6 |
| L. japonica BAX513 - Set 4 | 0.2 | 7.9-14.8 |

Example 7

Effect of Fucoidan on TFPI Function

Figure 14:
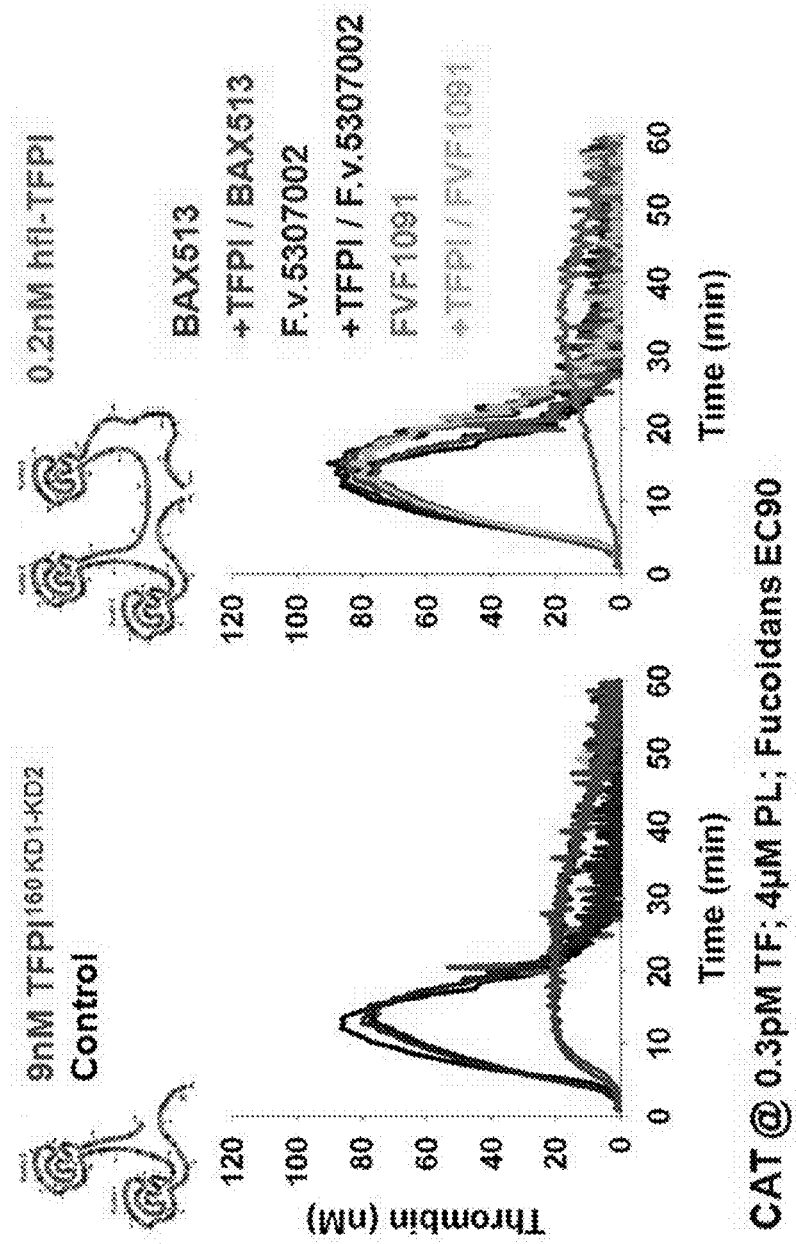
FIG. 14 shows an example of data acquired for the procoagulant activity of some fucoidans as measured using calibrated automated thrombography (CAT) to determine the mode of TFPI inhibition by fucoidans in FVIII-inhibited plasma.

The effect of fucoidan on TFPI function was tested using the various fucoidan compositions. In particular, the effect of fucoidan on the function of TFPI was tested by calibrated automated thrombography at low TF concentration (1 pM) in pooled normal plasma in the presence and absence of antibodies which inhibit the activities of TFPI. Controls were performed in which no fucoidan was present. Results from studies on the mode of action on TFPI with various fucoidans in TFPI depleted and FVIII inhibited plasma or normal plasma are shown in Tables 16-17, below. An example of CAT assay results is shown in FIG. 14.

Figure 15:
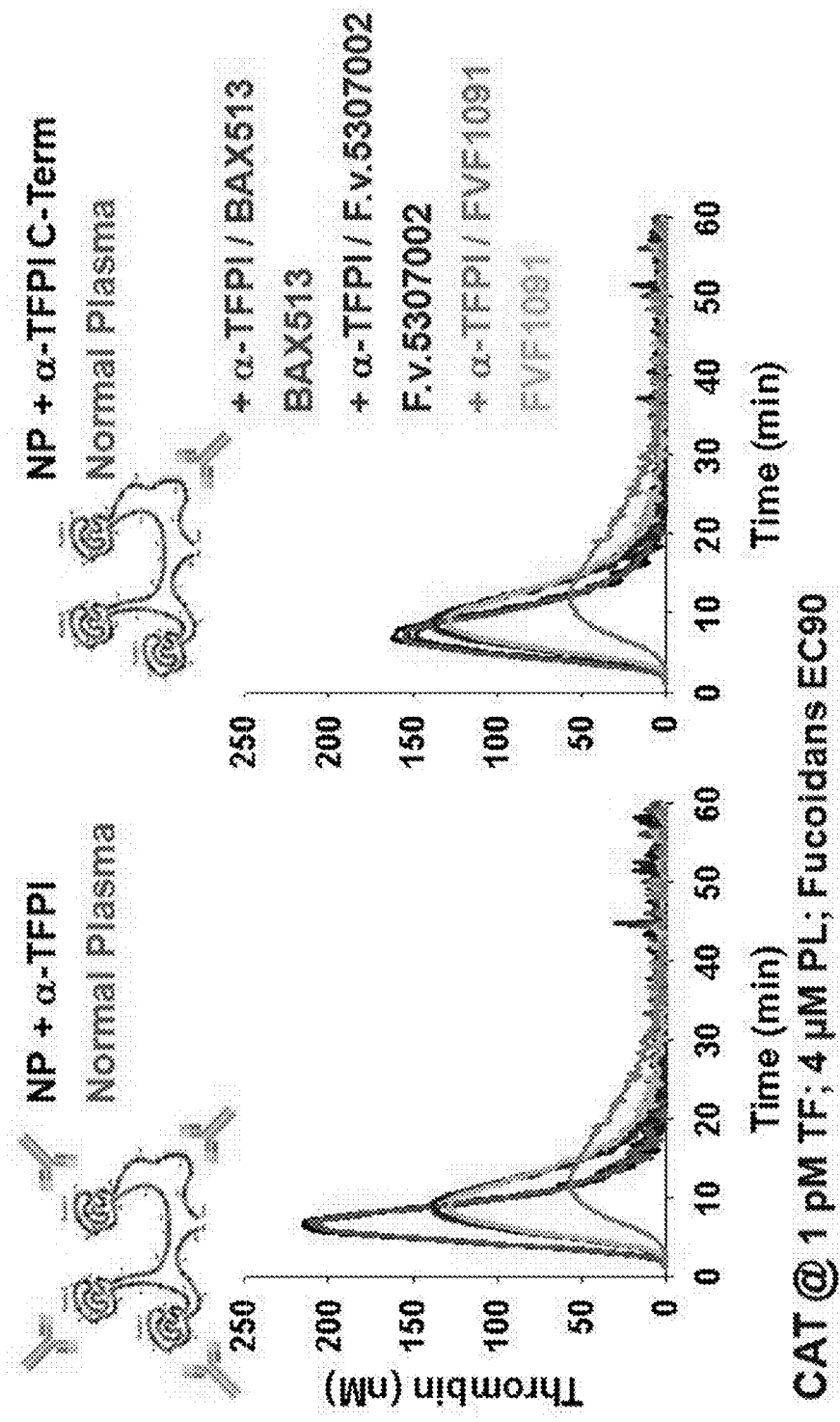
FIG. 15 shows an example of data acquired for the procoagulant activity of some fucoidans as measured using calibrated automated thrombography (CAT) to determine the mode of TFPI inhibition by fucoidans in normal plasma.

Results from studies on the mode of action on TFPI with some fucoidans of interest in normal plasma are shown in Table 18, below. An example of CAT assay results from these studies is shown in FIG. 15.

Figure 16:
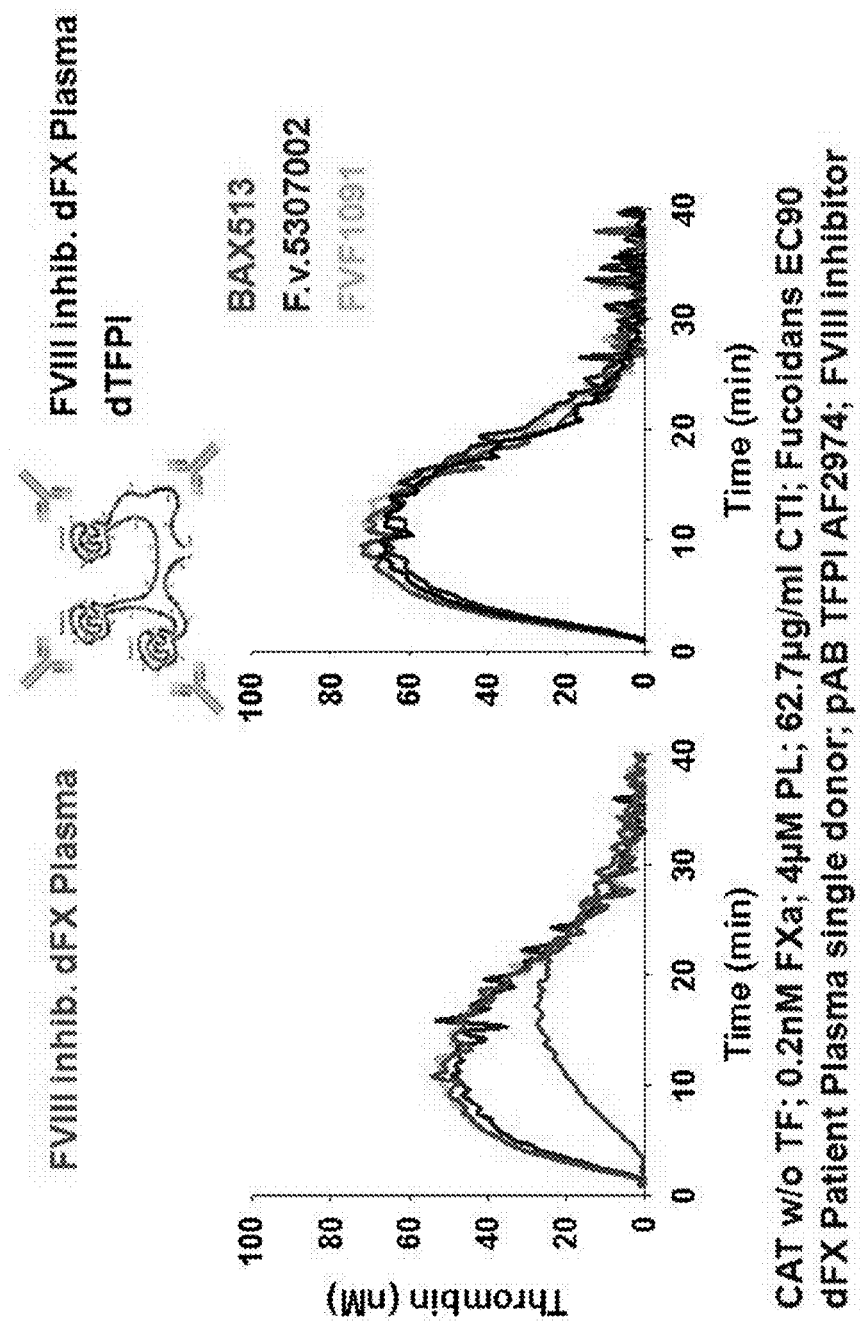
FIG. 16 shows an example of data acquired for the procoagulant activity of some fucoidans as measured using calibrated automated thrombography (CAT) to determine the mode of TFPI inhibition by fucoidans in FVIII-inhibited dFX plasma.

Results from studies on the mode of inhibition of TFPI with some fucoidans of interest in FVIII-inhibited dFX Plasma are shown in Table 19 below. An example of CAT assay results from these studies is shown in FIG. 16.

As can be seen from the results presented herein, fucoidans of the invention increased peak thrombin of pooled normal plasma and shortened the time to peak thrombin when added at optimal concentration which is consistent with its procoagulant activity. By blocking the activities of TFPI with a polyclonal anti-TFPI antibody, fucoidan parameters of thrombin generation did not change which indicated that fucoidan interferes with the function of TFPI.

To further explore the functional site on TFPI which is targeted by fucoidan, a monoclonal antibody directed against the basic C-terminus of TFPI was used. Addition of the antibody improved thrombin generation by increasing peak thrombin to 151 nM and reducing peak time to 7.8 min. When *Laminaria japonica* fucoidan was added to such a test system, it did not change parameters of thrombin generation. This indicates that fucoidan interferes with the C-terminus of TFPI, which is known to be of functional importance.

To further show that *Laminaria japonica* fucoidan interacts with the C-terminus of TFPI, recombinant C-terminally truncated TFPI (TFPI 1-160) was added to a test system in which the activity of full-length TFPI was blocked by an antibody directed against the C-terminus of TFPI. Addition of TFPI 1-160 reduced peak thrombin from 151 nM to 57 nM and increased peak time from 7.8 min to 11.0 min. Addition of *Laminaria japonica* fucoidan to this system did not change the parameters of thrombin generation. This confirms that *Laminaria japonica* fucoidan interacts and interferes with the activity of C-terminal TFPI regions. Additional studies were conducted using fucoidans of interest as described above and gave analogous results. As such, fucoidans or interest may be employed to inhibit activity by TFPI in FVIII inhibited plasma.

TABLE 16

Fucoidan *Laminaria japonica*/TFPI Mode of Action

| Fucoidan/protein | Peak thrombin (nM) | Peak time (min) |
| --- | --- | --- |
| Control | 83 | 11.3 |
| *Laminaria japonica* fucoidan 1.2 µg/mL | 171 | 8.2 |
| Control - polyclonal anti TFPI | 250 | 6.5 |
| *Laminaria japonica* fucoidan 1.2 µg/mL - polyclonal anti TFPI | 247 | 6.7 |
| Control - anti TFPI C-terminus | 151 | 7.8 |
| *Laminaria japonica* fucoidan 1.2 µg/mL - anti TFPI C-terminus | 149 | 8.0 |
| Control - anti TFPI C-terminus + TFPI 1-160 | 57 | 11.0 |
| *Laminaria japonica* fucoidan 1.2 µ/mL - anti TFPI C-terminus + TFPI 1-160 | 59 | 11.3 |

TABLE 17

Fucoidans/Inhibition of TFPI - in ΔTPFI FVIII inhibited Plasma

| nM Peak Thrombin | TFPI160 + Fuc. | hflTFPI + Fuc. | Fuc. |
| --- | --- | --- | --- |
| Buffer - No Fucoidan | 20.5 | 17.9 | 86.23 |
| *Laminaria japonica* | 20.74 | 83.9 | 79.35 |
| F.v. 5307002 | 20.32 | 87.93 | 76.72 |
| F.v. L/FVF1091 | 21.13 | 80.06 | 76.13 |
| F.v. L/FVF 1092 | 21.11 | 89.53 | 78.12 |
| F.v. L/FVF 1093 | 19.82 | 89.18 | 79.9 |
| F.v. 5508005 | 19.71 | 88.6 | 79.95 |
| E.m. DS100112A | 37.86 | 104.24 | 96.32 |

TABLE 18

Fucoidans/Inhibition of TFPI - in Normal Plasma

| nM Peak Thrombin | NP + Fuc | dTFPI- NP + Fuc | dTFPI C-Term + Fuc | dTFPI C-Term + TFPI160 + Fuc |
| --- | --- | --- | --- | --- |
| Buffer - No Fucoidan | 57.02 | 216.6 | 162.59 | 75.2 |
| *Laminaria japonica* | 139.52 | 210.85 | 148.99 | 71.13 |
| F.v. 5307002 | 138.01 | 213 | 153.81 | 74.66 |
| F.v. L/FVF1091 | 129.39 | 210.74 | 155.91 | 73.75 |
| F.v. L/FVF 1092 | 142.44 | 192.07 | 134.93 | 72.03 |
| F.v. L/FVF 1093 | 138.84 | 205.23 | 140.87 | 71.49 |
| F.v. 5508005 | 134.81 | 201.38 | 135.75 | 69.38 |
| E.m. DS100112A | 213.29 | 224.45 | 181.84 | 164.14 |

TABLE 19

Fucoidans/Inhibition of TFPI - in FVIII inhibited dFX Plasma

| nM Peak Thrombin | dFX + Fuc (EC50) | dFX/ dTFPI + Fuc (EC50) | dFX + Fuc (EC90) | dFX/ dTFPI + Fuc (EC90) |
| --- | --- | --- | --- | --- |
| Buffer - No Fucoidan | 27.15 | 66.28 | 27.15 | 66.28 |
| *Laminaria japonica* | 33.37 | 65.72 | 51.38 | 69.3 |
| F.v. 5307002 | 39.43 | 60.88 | 46.84 | 63.9 |
| F.v. L/FVF1091 | 36.06 | 67.22 | 51.64 | 69.27 |
| F.v. L/FVF 1092 | 37.57 | 71.94 | 57.94 | 79.19 |
| F.v. L/FVF 1093 | 38.95 | 73.85 | 59.18 | 81.54 |
| F.v. 5508005 | 49.6 | 100.01 | 75.22 | 96.29 |
| E.m. DS100112A | 46.44 | 91.04 | 82.4 | 87.68 |

Surface plasmon resonance experiments (Biacore 3000, G.E. Healthcare) were also used to study the interaction of fucoidan with human TFPI proteins. The proteins used were full-length TFPI (aa 1-276) and C-terminally truncated TFPI (aa 1-160). The C-terminally truncated TFPI 1-160 lacks the negatively charged C-terminus and the Kunitz domain 3. Full-length TFPI (flTFPI) was constitutively expressed by SKHep1 cells and purified by a multistep purification protocol using conventional purification devices and columns. TFPI 1-160 was expressed by *E. coli* in inclusion bodies and was refolded and purified by a multistep purification protocol using conventional purification devices and columns. The proteins were covalently coupled to a CM5 chip (GE Healthcare) using conventional amine coupling chemistry at pH 4.5 (10 mM NaAcetate) resulting in immobilization of 900 RU for flTFPI and 500 RU for TFPI 1-160, respectively.

For the binding assays the surfaces were equilibrated at a flow rate of 30 µL/min with HBS-P buffer (0.01M Hepes pH 7.4; 0.15M NaCl; 0.005% Surfactant P20) (GE Healthcare) to which 1% Tween 80 (Merck) was added. After 75 seconds, the *Laminaria japonica* fucoidan dissolved in HBS-P, 1% Tween 80 was injected for 450 seconds at concentrations ranging from 0.02 µg/mL to 250 µg/mL followed by a dissociation time of 475 seconds. The chip was regenerated by injecting 10 µL of 2.5 M NaCl followed by 10 mM NaOH, 1 M NaCl. HBS-P buffer plus 1% Tween 80 was used throughout the binding assays. Each sensorgram was referenced against buffer and the blank cell, respectively.

Figure 17:
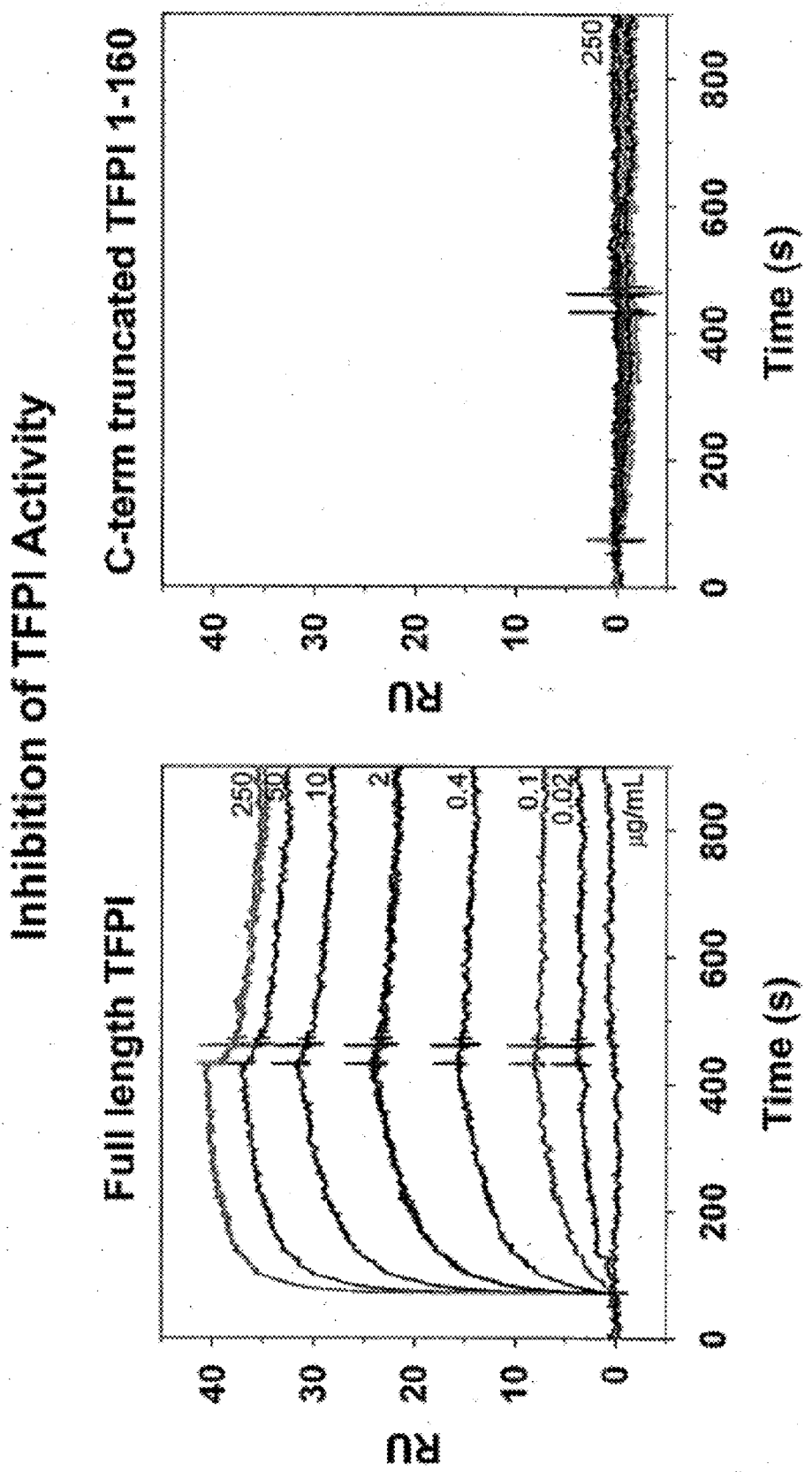
FIG. 17 shows results from studies to probe the interaction of fucoidan with human TFPI proteins as measured by surface plasmon resonance experiments (Biacore 3000, G.E. Healthcare).

Results are shown in FIG. 17. Fucoidan reacted with flTFPI in a concentration dependent manner, whereas no binding was observed with C-terminally truncated TFPI 1-160. This indicates that fucoidan (e.g., *Laminaria japonica*) binds in the C-terminal region of TFPI, which is known to be of functional importance.

Example 8

In Vitro Studies in Animal Plasma

Studies of fucoidans of interest were conducted in animal plasma in order to identify one or more animal species for future in vivo studies in which fucoidan response can be observed. CAT assays were conducted by titration of fucoidan in a wide concentration range (0.02-300 µg/mL) in normal and if possible, FVIII-inhibited animal plasma. Animal plasmas from human, cynomolgus monkey, guinea pig, rat, dog, rabbit, mouse and minipig were tested. CAT conditions were optimized for each animal species, in accordance with the concentration of FVIII inhibitor, concentration of tissue factor and plasma dilution. Assay conditions for each animal species are shown in Table 20, below. Coagulant effects were measured in a therapeutic window of up to about 300 g/mL.

Based on animal plasma studies, cynomolgus monkey, guinea pig and rat were determined to be suitable candidates for possible in vivo studies to determine fucoidan response. Plasma from dog, rabbit, mouse and minipig were determined to be less suitable candidates for in vivo studies.

In accordance with in vitro animal plasma test studies, two guinea pig models were developed to evaluate in vivo activity of fucoidans of interest: a carotid occlusion model and ex-vivo TEG analysis of whole blood.

TABLE 20

CAT Assay Conditions for in vitro studies in Animal Plasma

| Species | Plasma Dilution | FVIII Inhibitor Concentration (BU/mL) | TF Concentration (pM) |
|---|---|---|---|
| Human | 1:1.5 | 50 | 1 |
| Rat | 1:3 | n/a | 0.6 |
| Monkey | 1:1.5 | 150 | 0.6 |
| Guinea Pig | 1:3 | 150 | 0.6 |
| Minipig | 1:1.5 | 300 | 0.1 |
| Mouse | 1:3 | 150 | 0.6 |

Example 9

In Vivo Studies in Guinea Pits

Studies to evaluate the activity of fucoidans ex vivo were conducted using guinea pigs as animal models. To inhibit endogenous FVIII in the guinea pig an FVIII inhibitor (Z994; 42 BU/kg) was administered intravenuously 45 minutes prior to blood sampling. Fucoidan preparation F.v. VG201096B at 0.1, 0.4 or 1.6 mg/kg was administered intravenuously 5 minutes prior to blood sampling. Puncture of the vena cava caudalis was performed to sample whole blood. Measurements by thromboelastography were conducted immediately after sampling the citrated whole blood and was observed for a maximal 120 minute period.

Based on studies conducted using: a) inhibitor and NaCl; b) inhibitor and 0.1 mg/kg NASP; c) inhibitor and 0.4 mg/kg NASP; d) inhibitor and 1.6 mg/kg NASP; and e) inhibitor and 300 U/kg FEIBA, the in vivo studies by TEG analysis of whole blood from guinea pigs showed that NASP 0.4 mg/kg and FEIBA 300 U/kg performed better (i.e., more procoagulant activity) than NaCl.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the embodiments shown and described herein. Rather, the scope and spirit of present invention is embodied by the appended claims.

What is claimed is:

1. A method of enhancing blood coagulation in a subject, the method comprising (i) administering to the subject diagnosed as having a blood coagulation disorder a procoagulant amount of a composition comprising a purified non-anticoagulant sulfated polysaccharide (NASP) comprising 70% or more fucose saccharide residues;

the NASP having fucoidan selected from the group consisting of Fucoidan 5307002, *Fucus vesiculosus*, max. MW peak 126.7 kD; Fucoidan VG49, *Fucus vesiculosus*, hydrolyzed sample of 5307002 of lower MW, max. MW peak 22.5 kD; Fucoidan VG57, *Undaria pinnatifida*, high charge high sulphation, deacetylated; Fucoidan 5508005, *Undaria pinnatifida*, depyrogenated; Fucoidan L/FVF-01091, *Fucus vesiculosus*, depyrogenated, max. MW peak 125 kD; Fucoidan L/FVF-01092, *Fucus vesiculosus*, depyrogenated, max. MW peak 260 kD; Fucoidan L/FVF-01093, *Fucus vesiculosus*, hydrolyzed depyrogenated, max. MW peak 36 kD; fucoidan from *Ecklonia radiata*; fucoidan from *Ecklonia maxima*; fucoidan from *Macrocystis pyrifera*; and combinations thereof;

wherein the procoagulant amount is an effective amount of the composition to enhance blood coagulation in the subject.

2. The method according to claim 1, wherein the NASP is extracted from a biological source.

3. The method according to claim 1, wherein at least two of the saccharide residues of the NASP are selected from the group consisting of fucose, galactose, glucose, xylose and mannose.

4. The method according to claim 1, wherein the NASP comprises 70% or more fucose saccharide residues and 20% or more galactose saccharide residues.

5. The method according to claim 1, wherein the NASP is a branched polysaccharide.

6. The method according to claim 1, wherein the NASP is a linear polysaccharide.

7. The method according to claim 1, wherein 75% or more saccharide residues of the NASP are monosulfated.

8. The method according to claim 1, wherein the NASP comprises 40% or more sulfated esters of fucose saccharide residues.

9. The method according to claim 1, further comprising administering a blood coagulation factor to the subject.

10. The method according to claim 9, wherein the blood coagulation factor is selected from the group consisting of factor Xa, factor IXa, factor Xia, factor XIIa, VIIIa, prekallekrein, and high-molecular weight kininogen, tissue factor, factor VIIa, factor Va, factor Xa, factor II, factor V, factor VII, factor VIII, factor IX, factor X, factor XI, factor XII, factor XIII, von Willebrands factor and combinations thereof.

11. The method according to claim 1, wherein the NASP is administered at a dosage ranging from 0.01 mg/kg to 100 mg/kg.

12. The method according to claim 1, wherein the NASP has a molecular weight that ranges from 10 to 30,000 daltons.

13. The method according to claim 1, wherein the subject has been diagnosed as having a bleeding disorder selected from the group consisting of a chronic or acute bleeding disorder, a congenital coagulation disorder caused by a blood factor deficiency, and an acquired coagulation disorder.

* * * * *